(12) United States Patent
Matsuura

(10) Patent No.: US 11,284,845 B2
(45) Date of Patent: Mar. 29, 2022

(54) TOMOSYNTHESIS IMAGING CONTROL DEVICE, METHOD FOR OPERATING TOMOSYNTHESIS IMAGING CONTROL DEVICE, PROGRAM FOR OPERATING TOMOSYNTHESIS IMAGING CONTROL DEVICE, AND RADIATION SOURCE

(71) Applicant: FUJIFILM Corporation, Tokyo (JP)

(72) Inventor: Masayoshi Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/919,461

(22) Filed: Jul. 2, 2020

(65) Prior Publication Data

US 2021/0022690 A1    Jan. 28, 2021

(30) Foreign Application Priority Data

Jul. 26, 2019   (JP) ............................. JP2019-137743

(51) Int. Cl.
    *A61B 6/02*      (2006.01)
    *A61B 6/00*      (2006.01)

(52) U.S. Cl.
     CPC .............. *A61B 6/025* (2013.01); *A61B 6/502* (2013.01)

(58) Field of Classification Search
     CPC ................................ A61B 6/025; A61B 6/502
     See application file for complete search history.

(56) References Cited

U.S. PATENT DOCUMENTS

| | | | | |
|---|---|---|---|---|
| 2003/0076920 A1* | 4/2003 | Shinno | ................... | A61B 6/032 378/4 |
| 2006/0233297 A1* | 10/2006 | Ishiyama | ............... | A61B 6/032 378/9 |
| 2009/0323893 A1* | 12/2009 | Hanke | .................... | A61B 6/025 378/37 |
| 2010/0074503 A1* | 3/2010 | Bruder | ................... | A61B 6/481 382/131 |
| 2013/0107274 A1* | 5/2013 | Vertikov | ............ | G01B 9/02045 356/479 |
| 2014/0204338 A1* | 7/2014 | Murase | ................ | A61B 3/0041 351/206 |
| 2016/0088718 A1* | 3/2016 | Jiang | ........................ | H05G 1/34 378/110 |

(Continued)

FOREIGN PATENT DOCUMENTS

| | | | |
|---|---|---|---|
| DE | 102013202629 A1 * | 8/2014 | ............. A61B 6/586 |
| EP | 2326248 B1 | 11/2017 | |
| JP | 2016135319 A | 7/2016 | |

*Primary Examiner* — Blake C Riddick
(74) *Attorney, Agent, or Firm* — Studebaker & Brackett PC

(57) ABSTRACT

A control device includes a detection unit, a determination unit, a generation unit, and a control unit. The detection unit detects a state of each of the plurality of radiation tubes in a case in which tomosynthesis imaging that continuously irradiates an object with radiation at a plurality of different irradiation angles in order to generate a tomographic image in any tomographic plane of the object is performed using the plurality of radiation tubes. The determination unit determines whether or not to permit the generation of the tomographic image on the basis of the detection result of the detection unit and outputs a determination result. The generation unit generates the tomographic image. The control unit controls the operation of the generation unit on the basis of the determination result.

20 Claims, 43 Drawing Sheets

(56) References Cited

U.S. PATENT DOCUMENTS

| 2016/0183887 A1* | 6/2016 | Toba | A61B 6/12 600/424 |
| 2017/0276621 A1* | 9/2017 | Nagata | G01N 23/223 |
| 2018/0071551 A1* | 3/2018 | Berlinger | A61N 5/1077 |
| 2019/0200948 A1* | 7/2019 | He | A61B 6/5205 |

* cited by examiner

FIG. 12

| TARGET | DETECTION TIMING | ~80 |
|---|---|---|
| TEMPERATURE | BEFORE OPERATION | |
| DISCHARGE | AFTER OPERATION | |
| CATHODE | AFTER OPERATION | |

FIG. 13

| TARGET | DETECTION CONTENT | STATE | REMARKS |
|---|---|---|---|
| TEMPERATURE | TEMPERATURE IS LESS THAN TEMPERATURE THRESHOLD VALUE | NORMAL | TEMPERATURE THRESHOLD VALUE = TEMPERATURE THAT REACHES SERVICE TEMPERATURE OF RADIATION TUBE IN CASE IN WHICH RADIATION IS CONSECUTIVELY EMITTED FIVE TIMES |
| TEMPERATURE | TEMPERATURE IS EQUAL TO OR GREATER THAN TEMPERATURE THRESHOLD VALUE | ABNORMAL | |
| DISCHARGE | NUMBER OF OCCURRENCES OF DISCHARGE IS LESS THAN NUMBER-OF-TIMES THRESHOLD VALUE | NORMAL | NUMBER-OF-TIMES THRESHOLD VALUE = 1 |
| DISCHARGE | NUMBER OF OCCURRENCES OF DISCHARGE IS EQUAL TO OR GREATER THAN NUMBER-OF-TIMES THRESHOLD VALUE | ABNORMAL | |
| CATHODE | FAILURE IS PRESENT | NORMAL | |
| CATHODE | FAILURE IS ABSENT | ABNORMAL | |

DETECTION CONDITIONS

| DETERMINATION CONDITIONS | | | |
|---|---|---|---|
| DETECTION RESULTS | | GENERATION OF TOMOGRAPHIC IMAGE | REMARKS |
| IRRADIATION ESSENTIAL RADIATION TUBE IS IN NORMAL STATE AND NUMBER OF RADIATION TUBES IN NORMAL STATE INCLUDING IRRADIATION ESSENTIAL RADIATION TUBE AND RADIATION TUBES OTHER THAN IRRADIATION ESSENTIAL RADIATION TUBE IS EQUAL TO OR GREATER THAN MINIMUM REQUIRED NUMBER OF RADIATION TUBES | (FIRST PATTERN) | ALLOWED | MINIMUM REQUIRED NUMBER OF RADIATION TUBES = 10 |
| IRRADIATION ESSENTIAL RADIATION TUBE IS IN ABNORMAL STATE OR NUMBER OF RADIATION TUBES IN ABNORMAL STATE EXCEPT IRRADIATION ESSENTIAL RADIATION TUBE IS GREATER THAN MAXIMUM ALLOWABLE NUMBER OF RADIATION TUBES | (SECOND PATTERN) | NOT ALLOWED | MAXIMUM ALLOWABLE NUMBER OF RADIATION TUBES = 5 |

FIG. 16

DETECTION RESULT

| No. (POSITION) | TEMPERATURE | DISCHARGE | CATHODE |
|---|---|---|---|
| 1(SP1) | NORMAL | NORMAL | NORMAL |
| 2(SP2) | NORMAL | ABNORMAL | NORMAL |
| 3(SP3) | NORMAL | NORMAL | NORMAL |
| 4(SP4) | NORMAL | NORMAL | NORMAL |
| 5(SP5) | NORMAL | NORMAL | NORMAL |
| 6(SP6) | NORMAL | NORMAL | NORMAL |
| 7(SP7) | ABNORMAL | - | - |
| 8(SP8) | NORMAL | NORMAL | NORMAL |
| 9(SP9) | NORMAL | NORMAL | NORMAL |
| 10(SP10) | NORMAL | NORMAL | NORMAL |
| 11(SP11) | NORMAL | NORMAL | NORMAL |
| 12(SP12) | ABNORMAL | - | - |
| 13(SP13) | NORMAL | NORMAL | NORMAL |
| 14(SP14) | NORMAL | NORMAL | NORMAL |
| 15(SP15) | NORMAL | NORMAL | NORMAL |

~75

 ··· IRRADIATION ESSENTIAL RADIATION TUBE

FIG. 24

| | | | |
|---|---|---|---|
| | NOTIFICATION SCREEN | | 85 |
| TEMPERATURE AND AMOUNT OF HEAT/HEAT CAPACITY OF EACH RADIATION TUBE ARE SHOWN. | | | |
| No. | TEMPERATURE (°C) | AMOUNT OF HEAT/HEAT CAPACITY (%) | 86 |
| 1 | 42 | 70 | |
| 2 | 48 | 80 | |
| 3 | 49 | 82 | |
| 4 | 49 | 82 | |
| 5 | 50 | 83 | |
| 6 | 51 | 85 | |
| 7 | 51 | 85 | |
| 8 | 51 | 85 | |
| 9 | 52 | 87 | |
| 10 | 50 | 83 | |
| 11 | 49 | 82 | |
| 12 | 49 | 82 | |
| 13 | 46 | 77 | |
| 14 | 43 | 72 | |
| 15 | 40 | 67 | |

CONFIRMATION — 87

| TARGET | DETECTION CONTENT | STATE | REMARKS |
|---|---|---|---|
| TEMPERATURE | TEMPERATURE IS LESS THAN TEMPERATURE THRESHOLD VALUE | NORMAL | TEMPERATURE THRESHOLD VALUE = TEMPERATURE THAT REACHES SERVICE TEMPERATURE OF RADIATION TUBE IN CASE IN WHICH RADIATION IS CONSECUTIVELY EMITTED FIVE TIMES |
| TEMPERATURE | TEMPERATURE IS EQUAL TO OR GREATER THAN TEMPERATURE THRESHOLD VALUE | ABNORMAL | |
| DISCHARGE | NUMBER OF OCCURRENCES OF DISCHARGE IS LESS THAN NUMBER-OF-TIMES THRESHOLD VALUE | NORMAL | NUMBER-OF-TIMES THRESHOLD VALUE = 2 |
| DISCHARGE | NUMBER OF OCCURRENCES OF DISCHARGE IS EQUAL TO OR GREATER THAN NUMBER-OF-TIMES THRESHOLD VALUE | ABNORMAL | |
| CATHODE | FAILURE IS PRESENT | NORMAL | |
| CATHODE | FAILURE IS ABSENT | ABNORMAL | |

DETECTION CONDITIONS

FIG. 38

| IRRADIATION RETRYING OPERATION SUCCESS AND FAILURE INFORMATION ||
|---|---|
| No. (POSITION) | SUCCESS RATE |
| 1(SP1) | 100 |
| 2(SP2) | 75 |
| 3(SP3) | 75 |
| 4(SP4) | 100 |
| 5(SP5) | 100 |
| 6(SP6) | 60 |
| 7(SP7) | 100 |
| 8(SP8) | 75 |
| 9(SP9) | 100 |
| 10(SP10) | 100 |
| 11(SP11) | 60 |
| 12(SP12) | 75 |
| 13(SP13) | 50 |
| 14(SP14) | 100 |
| 15(SP15) | 100 |

DISCHARGE OCCURS IN No. 4 (SUCCESS RATE OF 100%), No. 11 (SUCCESS RATE OF 60%), AND No. 13 (SUCCESS RATE OF 50%) RADIATION TUBES

No. 4 (SUCCESS RATE OF 100%) AND No. 11 (SUCCESS RATE OF 60%) RADIATION TUBES ARE SELECTED AS RADIATION TUBES TO BE SUBJECTED TO IRRADIATION RETRYING OPERATION

FIG. 40

DISCHARGE OCCURRENCE HISTORY INFORMATION ~125

| No.1(SP1) | | No.2(SP2) | | | No.15(SP15) | |
|---|---|---|---|---|---|---|
| IMAGING | DISCHARGE | IMAGING | DISCHARGE | | IMAGING | DISCHARGE |
| CURRENT OPERATION | OCCURRED | CURRENT OPERATION | NOT OCCURRED | | CURRENT OPERATION | OCCURRED |
| PREVIOUS OPERATION | OCCURRED | PREVIOUS OPERATION | NOT OCCURRED | | PREVIOUS OPERATION | NOT OCCURRED |
| TWO OPERATIONS BEFORE | OCCURRED | TWO OPERATIONS BEFORE | NOT OCCURRED | | TWO OPERATIONS BEFORE | NOT OCCURRED |
| THREE OPERATIONS BEFORE | OCCURRED | THREE OPERATIONS BEFORE | NOT OCCURRED | | THREE OPERATIONS BEFORE | OCCURRED |
| FOUR OPERATIONS BEFORE | NOT OCCURRED | FOUR OPERATIONS BEFORE | NOT OCCURRED | ... | FOUR OPERATIONS BEFORE | OCCURRED |
| FIVE OPERATIONS BEFORE | OCCURRED | FIVE OPERATIONS BEFORE | NOT OCCURRED | | FIVE OPERATIONS BEFORE | OCCURRED |
| SIX OPERATIONS BEFORE | NOT OCCURRED | SIX OPERATIONS BEFORE | NOT OCCURRED | | SIX OPERATIONS BEFORE | NOT OCCURRED |
| SEVEN OPERATIONS BEFORE | NOT OCCURRED | SEVEN OPERATIONS BEFORE | NOT OCCURRED | | SEVEN OPERATIONS BEFORE | NOT OCCURRED |
| EIGHT OPERATIONS BEFORE | NOT OCCURRED | EIGHT OPERATIONS BEFORE | OCCURRED | | EIGHT OPERATIONS BEFORE | NOT OCCURRED |
| NINE OPERATIONS BEFORE | NOT OCCURRED | NINE OPERATIONS BEFORE | NOT OCCURRED | | NINE OPERATIONS BEFORE | NOT OCCURRED |

FIG. 43

| No. (POSITION) | TEMPERATURE | DISCHARGE | CATHODE |
|---|---|---|---|
| 1(SP1) | NORMAL | NORMAL | NORMAL |
| 2(SP2) | NORMAL | NORMAL | NORMAL |
| 3(SP3) | ABNORMAL | - | - |
| 4(SP4) | NORMAL | NORMAL | NORMAL |
| 5(SP5) | NORMAL | NORMAL | NORMAL |
| 6(SP6) | NORMAL | NORMAL | NORMAL |
| 7(SP7) | NORMAL | NORMAL | NORMAL |
| 8(SP8) | NORMAL | NORMAL | NORMAL |
| 9(SP9) | NORMAL | NORMAL | NORMAL |
| 10(SP10) | ABNORMAL | - | - |
| 11(SP11) | NORMAL | NORMAL | NORMAL |
| 12(SP12) | NORMAL | NORMAL | NORMAL |
| 13(SP13) | NORMAL | NORMAL | NORMAL |
| 14(SP14) | NORMAL | NORMAL | NORMAL |
| 15(SP15) | NORMAL | NORMAL | NORMAL |

DETECTION RESULT ~75

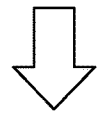

RADIATION TUBE AT SP13 THAT IS SYMMETRIC TO SP3 WITH RESPECT TO LINE AND RADIATION TUBE AT SP6 THAT IS SYMMETRIC TO SP10 WITH RESPECT TO LINE   ARE NOT OPERATED

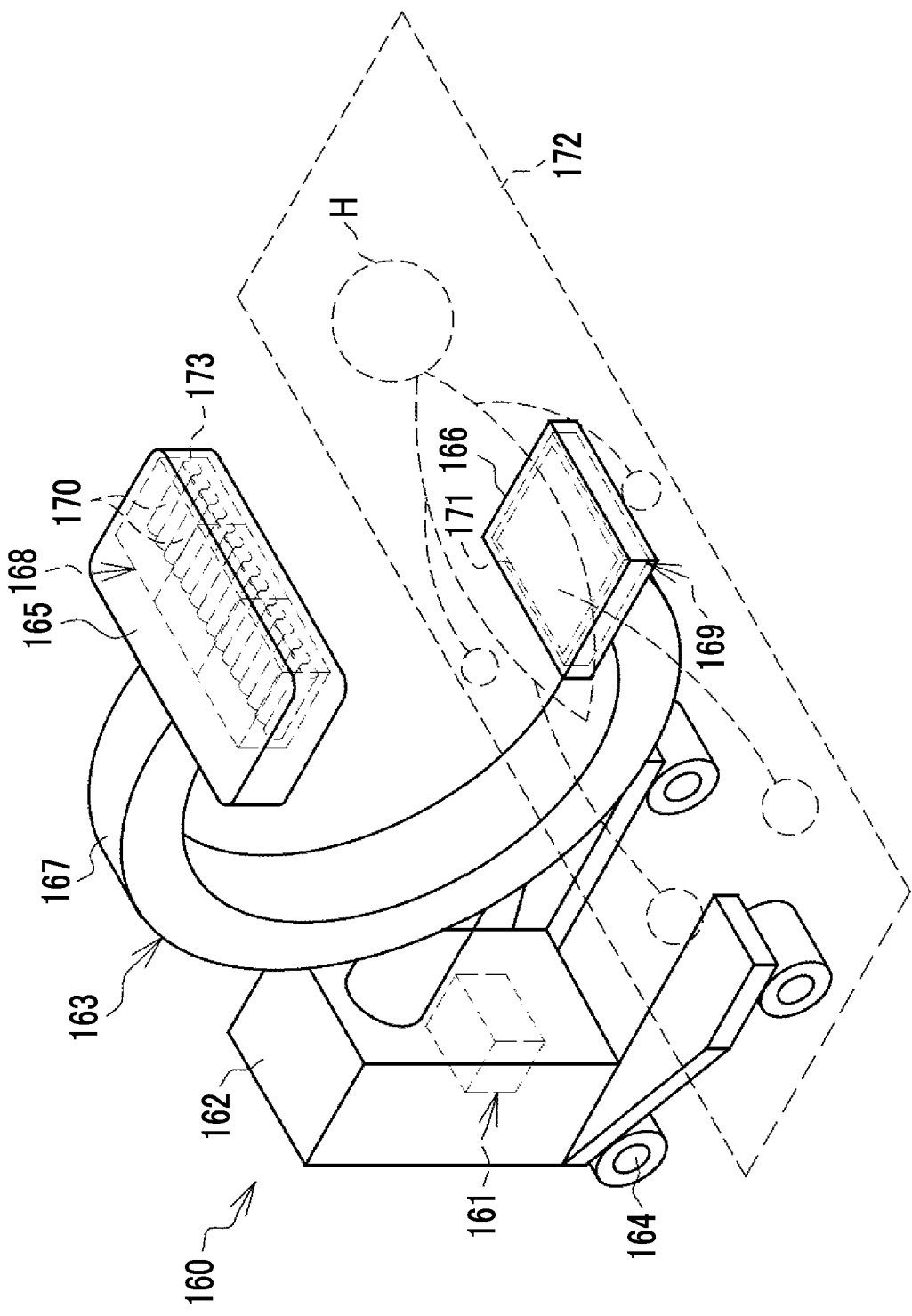

TOMOSYNTHESIS IMAGING CONTROL DEVICE, METHOD FOR OPERATING TOMOSYNTHESIS IMAGING CONTROL DEVICE, PROGRAM FOR OPERATING TOMOSYNTHESIS IMAGING CONTROL DEVICE, AND RADIATION SOURCE

CROSS-REFERENCE TO RELATED APPLICATIONS

The present application claims priority under 35 U.S.C. § 119 to Japanese Patent Application No., 2019-137743 filed on Jul. 26, 2019. The above application is hereby expressly incorporated by reference, in its entirety, into the present application.

BACKGROUND

1. Technical Field

The technology of the present disclosure relates to a tomosynthesis imaging control device, a method for operating a tomosynthesis imaging control device, a program for operating a tomosynthesis imaging control device, and a radiation source.

2. Description of the Related Art

Tomosynthesis imaging is performed which continuously irradiates an object with radiation at a plurality of different irradiation angles in order to generate a tomographic image in any tomographic plane of the object. JP2016-135319A discloses a technique that performs tomosynthesis imaging while moving a radiation source including one radiation tube to a plurality of positions corresponding to a plurality of different irradiation angles.

SUMMARY

In the tomosynthesis imaging apparatus according to the related art, such as the tomosynthesis imaging apparatus disclosed in JP2016-135319A, the radiation source including one radiation tube is moved to each position. Therefore, there is a problem that the imaging time is relatively long and a burden on the subject increases. For this reason, the inventors have examined a tomosynthesis imaging apparatus comprising a radiation source having a plurality of radiation tubes.

The radiation tube is likely to fall into an abnormal state in which it is difficult to emit an appropriate amount of radiation satisfying the set irradiation conditions, for example, in a case in which the temperature of the radiation tube is equal to or greater than a temperature threshold value based on the service temperature, a case in which discharge is repeated due to a decrease in the degree of vacuum, or a case in which a failure occurs in a cathode. In the tomosynthesis imaging apparatus disclosed in JP2016-135319A, one radiation tube is provided. Therefore, in a case in which the one radiation tube falls into an abnormal state, it is difficult to perform tomosynthesis imaging and to generate a tomographic image.

In contrast, in the radiation source including a plurality of radiation tubes examined by the inventors, there may be no problem depending on, for example, the number of radiation tubes in an abnormal state and the positions thereof even in a case in which tomosynthesis imaging is performed using the radiation tubes other than the radiation tube in the abnormal state to generate a tomographic image. Specifically, image quality, such as granularity, deteriorates slightly. However, in some cases, it is possible to generate a tomographic image with a preset resolution level from the projection images obtained by the emission of radiation from the radiation tubes other than the radiation tube in the abnormal state. In the course of the examination, the inventors have found a need for a technique that utilizes the advantage of the radiation source including a plurality of radiation tubes.

An object of the technology of the present disclosure is to provide a tomosynthesis imaging control device, a method for operating a tomosynthesis imaging control device, a program for operating a tomosynthesis imaging control device, and a radiation source that can utilize the advantage in a case in which tomosynthesis imaging is performed using a radiation source including a plurality of radiation tubes.

In order to achieve the above object, according to the present disclosure, there is provided a tomosynthesis imaging control device comprising: a detection unit that, in a case in which tomosynthesis imaging that continuously irradiates an object with radiation at a plurality of different irradiation angles to generate a tomographic image in any tomographic plane of the object is performed using at least three or more radiation tubes, detects whether or not the radiation tubes are in an abnormal state; and a determination unit that determines whether or not to permit the generation of the tomographic image on the basis of projection images captured using at least two or more radiation tubes other than a radiation tube detected to be in the abnormal state by the detection unit among the at least three or more radiation tubes.

Preferably, the tomosynthesis imaging control device further comprises: a generation unit that generates the tomographic image; and a first control unit that controls an operation of the generation unit on the basis of a determination result of the determination unit.

Preferably, in a case in which the radiation tube in the abnormal state is present and the determination unit determines to permit the generation of the tomographic image, the generation unit generates the tomographic image on the basis of the projection images captured using at least two or more radiation tubes other than the radiation tube detected to be in the abnormal state by the detection unit.

Preferably, the generation unit generates the tomographic image without using the projection image captured using the radiation tube detected to be in the abnormal state by the detection unit.

Preferably, in a case in which the detection unit does not detect the radiation tube in the abnormal state, the generation unit generates the tomographic image on the basis of projection images captured using all of the at least three or more radiation tubes.

Preferably, the plurality of radiation tubes include irradiation essential radiation tubes from which the emission of the radiation is essential to generate the tomographic image with a preset resolution level.

Preferably, in a case in which a detection result of the detection unit indicates that the irradiation essential radiation tubes are in a normal state and the number of radiation tubes in the normal state including the irradiation essential radiation tubes and the radiation tubes other than the irradiation essential radiation tubes is equal to or greater than a preset minimum required number of radiation tubes, the determination unit determines to permit the generation of the tomographic image.

Preferably, in a case in which the detection result of the detection unit indicates that the irradiation essential radiation tubes are in the abnormal state or in a case in which the detection result indicates that the number of radiation tubes in the abnormal state except the irradiation essential radiation tubes is greater than a preset maximum allowable number of radiation tubes, the determination unit determines not to permit the generation of the tomographic image.

Preferably, the irradiation essential radiation tubes are outermost radiation tubes in a range of a minimum irradiation angle required to generate the tomographic image with the preset resolution level.

Preferably, the irradiation essential radiation tubes are radiation tubes disposed at both ends among the plurality of radiation tubes.

Preferably, the detection unit detects that the radiation tube is in the abnormal state in at least one of a case in which a temperature of the radiation tube is equal to or greater than a preset temperature threshold value, a case in which the number of occurrences of discharge in the radiation tube has reached a preset number-of-times threshold value, or a case in which a failure has been recognized in a cathode of the radiation tube.

Preferably, the tomosynthesis imaging control device further comprises a second control unit that operates the irradiation essential radiation tube first among the plurality of radiation tubes and directs the detection unit to detect first whether or not the number of occurrences of discharge in the irradiation essential radiation tube has reached the number-of-times threshold value and whether or not a failure has been recognized in the cathode of the irradiation essential radiation tube.

Preferably, the number-of-times threshold value is equal to or greater than 2 and the tomosynthesis imaging control device further comprises a third control unit that directs the radiation tube, in which the number of occurrences of discharge is equal to or greater than 1 and is less than the number-of-times threshold value, to perform an irradiation retrying operation for emitting the radiation again.

Preferably, an upper limit is set for a total number of irradiation retrying operations.

Preferably, the tomosynthesis imaging control device further comprises a first notification unit that notifies that the irradiation retrying operation has been performed.

Preferably, the tomosynthesis imaging control device further comprises a second notification unit that notifies that maintenance is required for the radiation tube in which a frequency of discharge has reached a preset frequency threshold value.

Preferably, the tomosynthesis imaging control device further comprises a third notification unit that notifies at least one of the temperature of the radiation tube or a ratio of an amount of heat applied to a heat capacity of the radiation tube.

Preferably, the tomosynthesis imaging control device further comprises a fourth control unit that does not operate a radiation tube disposed at a position that is symmetric to the radiation tube in the abnormal state in the detection result of the detection unit with respect to a line.

Preferably, the tomosynthesis imaging control device further comprises a fourth notification unit that notifies that the radiation tube which has not emitted the radiation is present in a case in which the detection result of the detection unit indicates that the radiation tube in the abnormal state is present, the determination unit determines to permit the generation of the tomographic image, and the tomographic image has been generated.

According to the present disclosure, there is provided a method for operating a tomosynthesis imaging control device. The method comprises: a detection step of, in a case in which tomosynthesis imaging that continuously irradiates an object with radiation at a plurality of different irradiation angles to generate a tomographic image in any tomographic plane of the object is performed using at least three or more radiation tubes, detecting whether or not the radiation tubes are in an abnormal state; and a determination step of determining whether or not to permit the generation of the tomographic image on the basis of projection images captured using at least two or more radiation tubes other than a radiation tube detected to be in the abnormal state in the detection step among the at least three or more radiation tubes.

According to the present disclosure, there is provided a program for operating a tomosynthesis imaging control device. The program causes a computer to function as: a detection unit that, in a case in which tomosynthesis imaging that continuously irradiates an object with radiation at a plurality of different irradiation angles to generate a tomographic image in any tomographic plane of the object is performed using at least three or more radiation tubes, detects whether or not the radiation tubes are in an abnormal state; and a determination unit that determines whether or not to permit the generation of the tomographic image on the basis of projection images captured using at least two or more radiation tubes other than a radiation tube detected to be in the abnormal state by the detection unit among the at least three or more radiation tubes.

According to the present disclosure, there is provided a radiation source comprising a plurality of the radiation tubes whose operation is controlled by the tomosynthesis imaging control device. The plurality of radiation tubes include irradiation essential radiation tubes from which the emission of the radiation is essential to generate the tomographic image with a preset resolution level. The irradiation essential radiation tube has a higher heat dissipation performance than other radiation tubes and/or has a higher heat capacity than other radiation tubes.

According to the technology of the present disclosure, it is possible to provide a tomosynthesis imaging control device, a method for operating a tomosynthesis imaging control device, a program for operating a tomosynthesis imaging control device, and a radiation source that can utilize the advantage in a case in which tomosynthesis imaging is performed using a radiation source including a plurality of radiation tubes.

BRIEF DESCRIPTION OF THE DRAWINGS

Exemplary embodiments according to the technique of the present disclosure will be described in detail based on the following figures, wherein:

FIG. 12 is a table illustrating the detection timing of each detection target;

FIG. 13 is a diagram illustrating detection conditions;

FIG. 14 is a diagram illustrating determination conditions;

FIG. 16 is a diagram illustrating a detection result;

FIG. 24 is a diagram illustrating a notification screen for notifying the temperature and the amount of heat/heat capacity of each radiation tube;

FIG. 31 is a diagram illustrating detection conditions according to a second embodiment;

FIG. 38 is a diagram illustrating irradiation retrying operation success and failure information;

FIG. 39 is a diagram illustrating an aspect in which a radiation tube performing the irradiation retrying operation is selected on the basis of the irradiation retrying operation success and failure information;

FIG. 40 is a diagram illustrating discharge occurrence history information;

FIG. 43 is a diagram illustrating an aspect in which a radiation tube disposed at a position that is symmetric to the radiation tube in an abnormal state in the detection result with respect to a line is not operated;

FIG. 49 is a diagram illustrating an imaging apparatus for surgery.

DETAILED DESCRIPTION

First Embodiment

Figure 1:
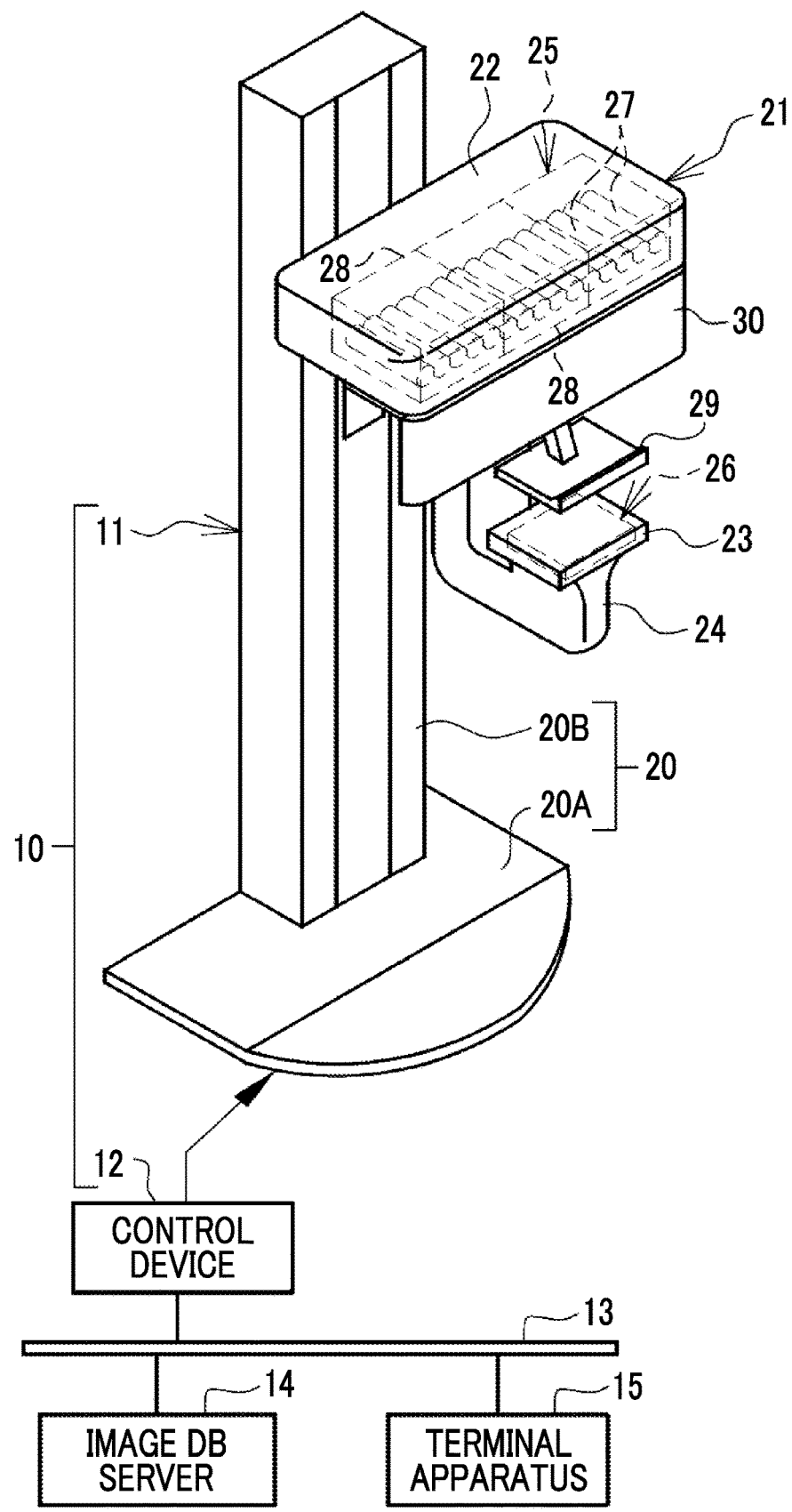
FIG. 1 is a diagram illustrating, for example, a mammography apparatus.
Figure 2:
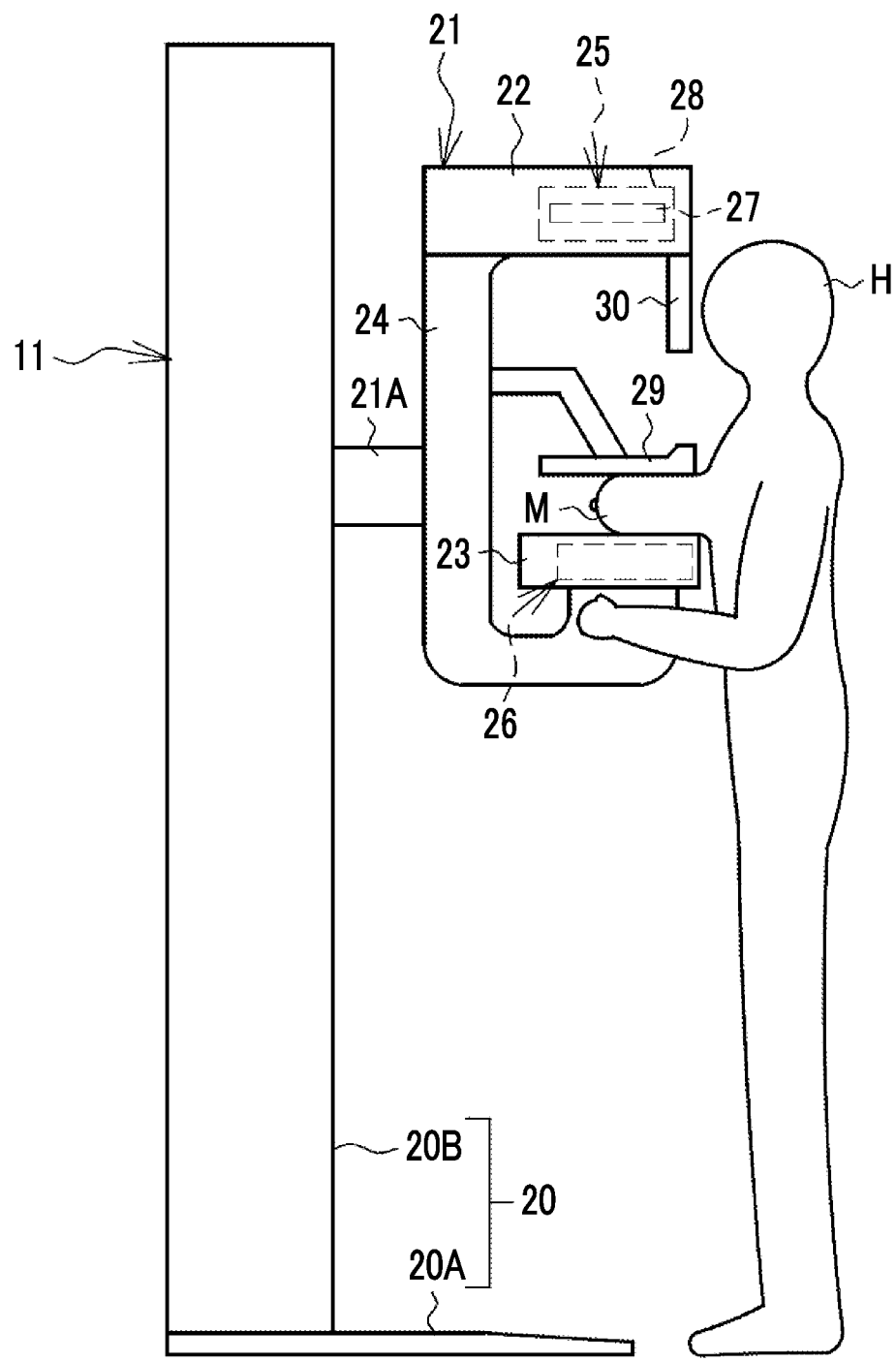
FIG. 2 is a diagram illustrating an apparatus main body of the mammography apparatus.

In FIGS. 1 and 2, a mammography apparatus 10 uses a breast M of a subject H as an object. The mammography apparatus 10 irradiates the breast M with radiation 37 (see, for example, FIG. 3), such as X-rays or y-rays, to capture a radiographic image of the breast M.

The mammography apparatus 10 includes an apparatus main body 11 and a control device 12 which is an example of a "tomosynthesis imaging control device" according to the technology of the present disclosure. The apparatus main body 11 is installed, for example, in a radiography room of a medical facility. The control device 12 is installed, for example, in a control room next to the radiography room. The control device 12 is, for example, a desktop personal computer. The control device 12 is connected to an image database (hereinafter, referred to as a DB) server 14 through a network 13, such as a local area network (LAN), such that it can communicate with the image DB server 14. The image DB server 14 is, for example, a picture archiving and communication system (PACS) server, receives a radiographic image from the mammography apparatus 10, stores the radiographic image, and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes 15 radiation tubes 27 and three housings 28 each of which accommodates five radiation tubes 27. The radiation tubes 27 are used for tomosynthesis imaging which captures a plurality of projection images of the breast M at different irradiation angles as radiographic images. The radiation detector 26 detects the radiation 37 transmitted through the breast M and outputs a radiographic image. In addition, the number of radiation tubes 27 is not limited to 15 in the above example. The number of radiation tubes 27 may be at least three or more.

A compression plate 29 is attached between the radiation source accommodation portion 22 and the detector accommodation portion 23 in the main body portion 24. The compression plate 29 is made of a material that transmits the radiation 37. The compression plate 29 is provided so as to face the detector accommodation portion 23. The compression plate 29 can be moved in a direction toward the detector accommodation portion 23 and a direction away from the detector accommodation portion 23. The compression plate 29 is moved toward the detector accommodation portion 23 and compresses the breast M interposed between the detector accommodation portion 23 and the compression plate 29.

A face guard 30 is attached to a lower part of the front surface of the radiation source accommodation portion 22. The face guard 30 protects the face of the subject H from the radiation 37.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
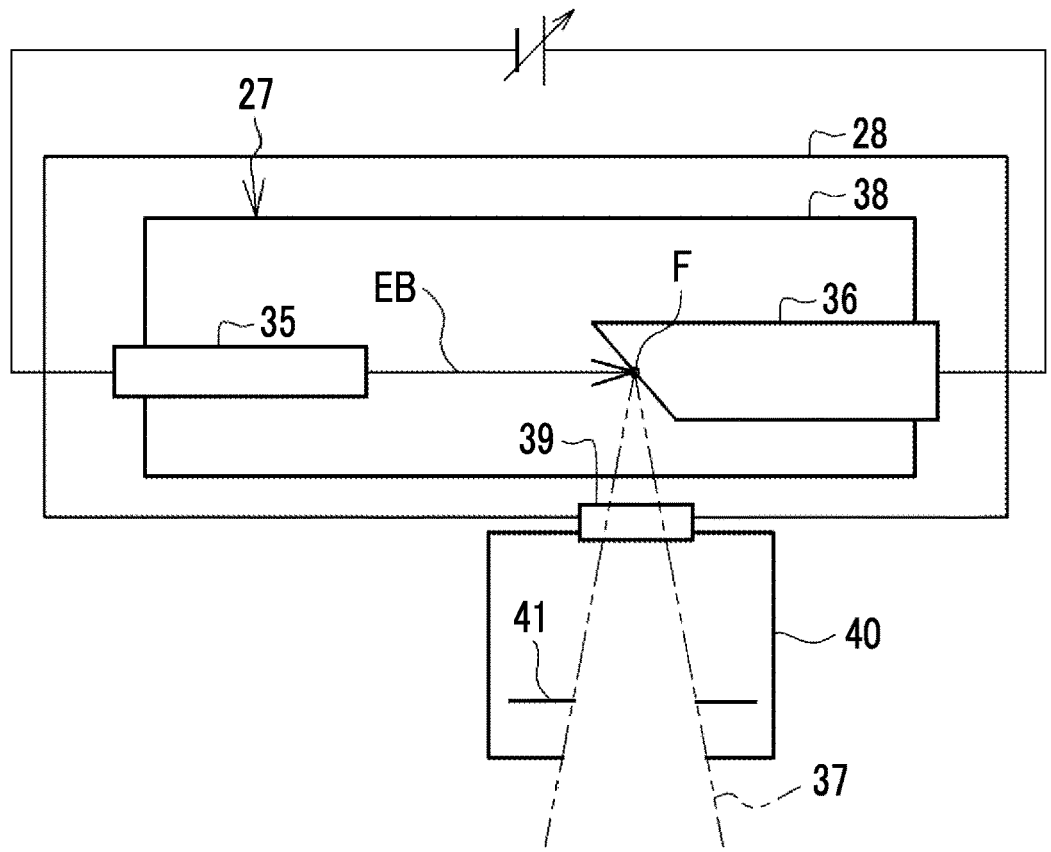
FIG. 3 is a diagram illustrating a radiation tube.

In FIG. 3, the radiation tube 27 includes a cathode 35 and an anode 36. The cathode 35 emits electrons. The electrons collide with the anode 36 and the anode 36 emits the radiation 37. The cathode 35 and the anode 36 are accommodated in a vacuum glass tube 38 with a substantially cylindrical shape. The cathode 35 is a cold cathode. Specifically, the cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides.

The housing 28 is provided with a radiation transmission window 39 that transmits the radiation 37. The radiation 37 emitted from the anode 36 is emitted to the outside of the housing 28 through the radiation transmission window 39. In addition, the housing 28 is filled with insulating oil.

An irradiation field limiter 40 (not illustrated in FIGS. 1 and 2) is provided below the radiation transmission window 39 in the height direction. The irradiation field limiter 40 is also called a collimator and sets the irradiation field of the radiation 37 in an imaging surface 49 (see FIG. 5) of the radiation detector 26. Specifically, the irradiation field limiter 40 includes a plurality of shielding plates 41 which are made of, for example, lead and shield the radiation 37 transmitted through the radiation transmission window 39. The shielding plates 41 are moved to change the size of, for example, a rectangular irradiation opening defined by the shielding plates 41, thereby setting the irradiation field of the radiation 37.

Figure 4:
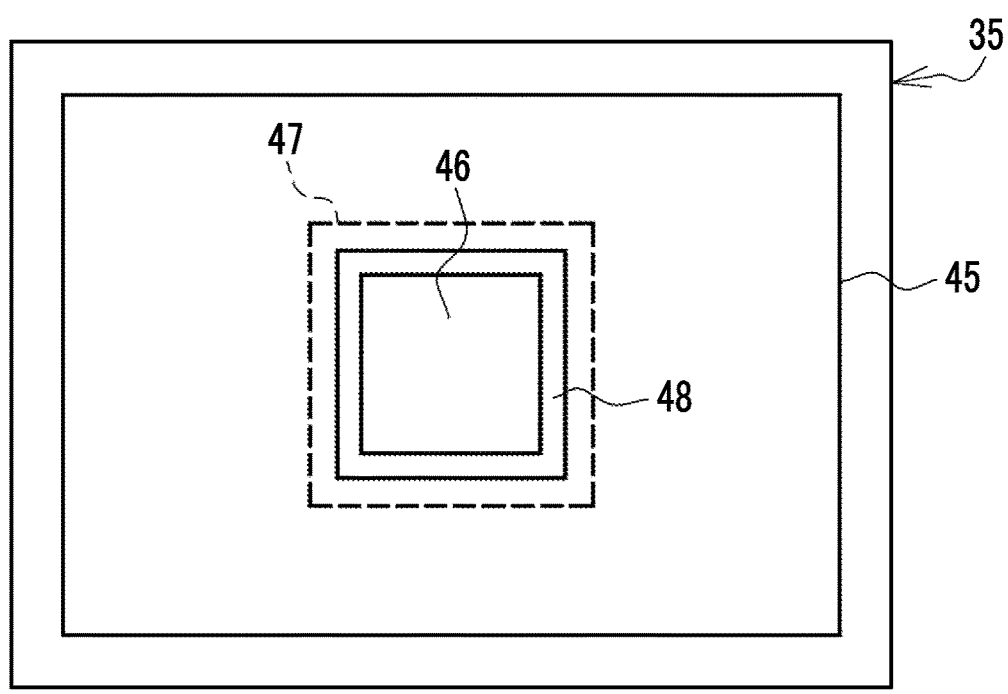
FIG. 4 is a diagram illustrating a cathode.

In FIG. 4, the cathode 35 has a structure in which an emitter electrode 46 and a gate electrode 47 are provided on a semiconductor substrate 45. The semiconductor substrate 45 is made of, for example, crystallized silicon. The emitter electrode 46 is made of, for example, carbon nanotube. The emitter electrode 46 is connected to the gate electrode 47. The emitter electrode 46 functions as an emission area of the electron beam EB.

A focusing electrode 48 is provided around the emitter electrode 46. The electron beam EB emitted from the emitter electrode 46 is accelerated toward the anode 36 and is focused by the application of a focusing voltage to the focusing electrode 48.

Figure 5:
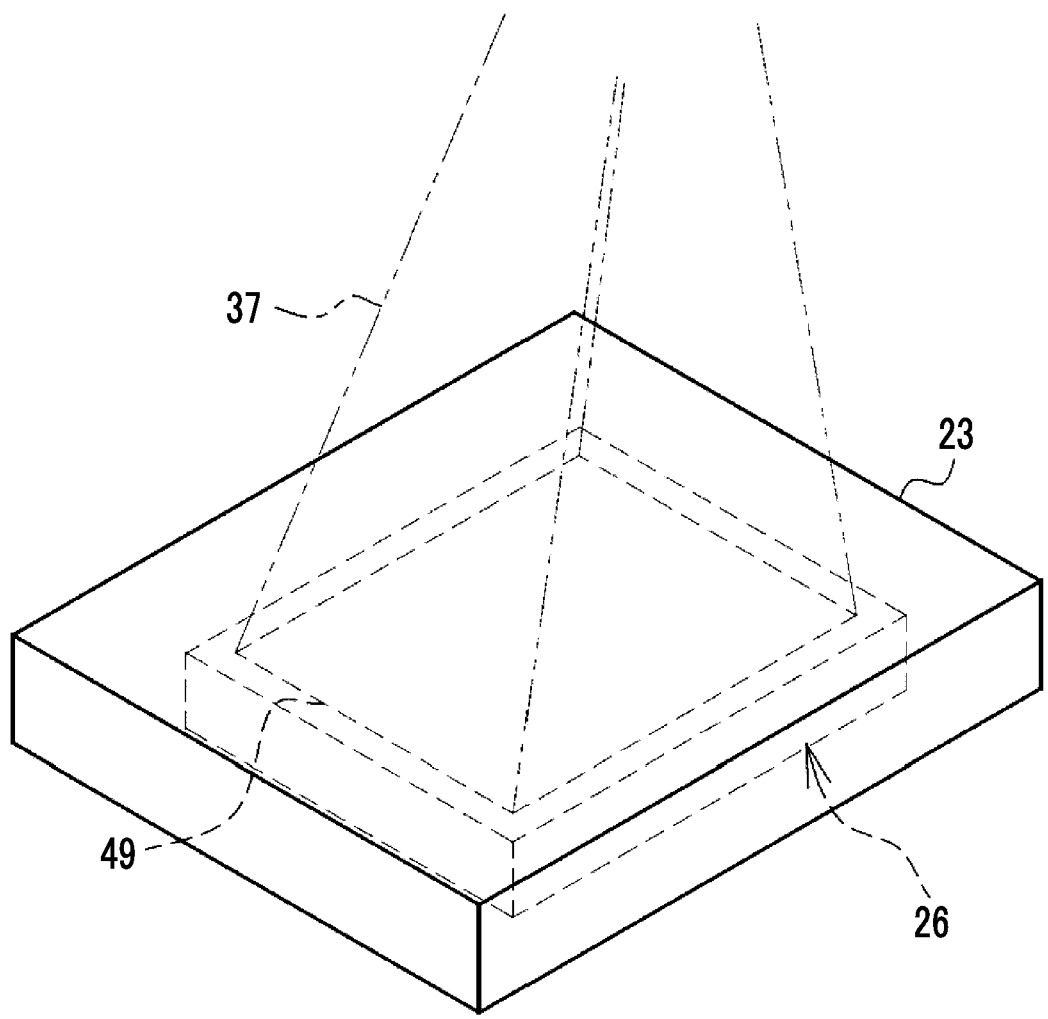
FIG. 5 is a diagram illustrating a detector accommodation portion.

In FIG. 5 illustrating the detector accommodation portion 23, the radiation detector 26 has the imaging surface 49. The imaging surface 49 detects the radiation 37 transmitted through the breast M and captures a projection image of the breast M. Specifically, the imaging surface 49 is a two-dimensional plane in which pixels converting the radiation 37 into an electric signal are two-dimensionally arranged. The radiation detector 26 is called a flat panel detection (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal.

Figure 6:
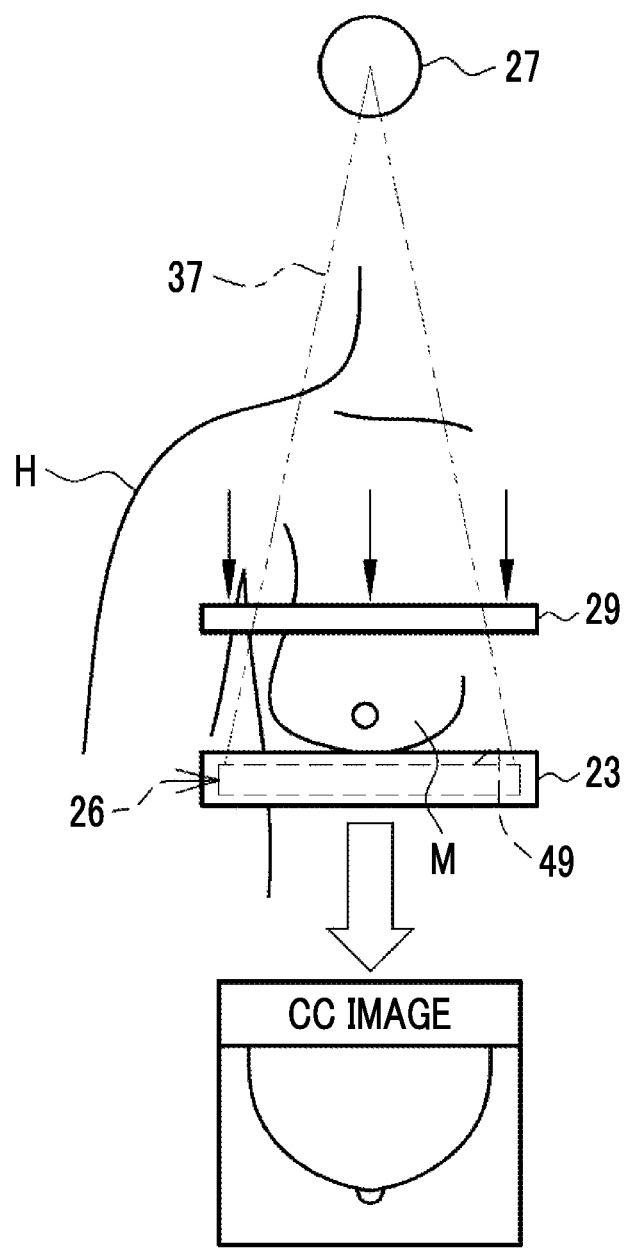
FIG. 6 is a diagram illustrating an aspect of CC imaging.
Figure 7:
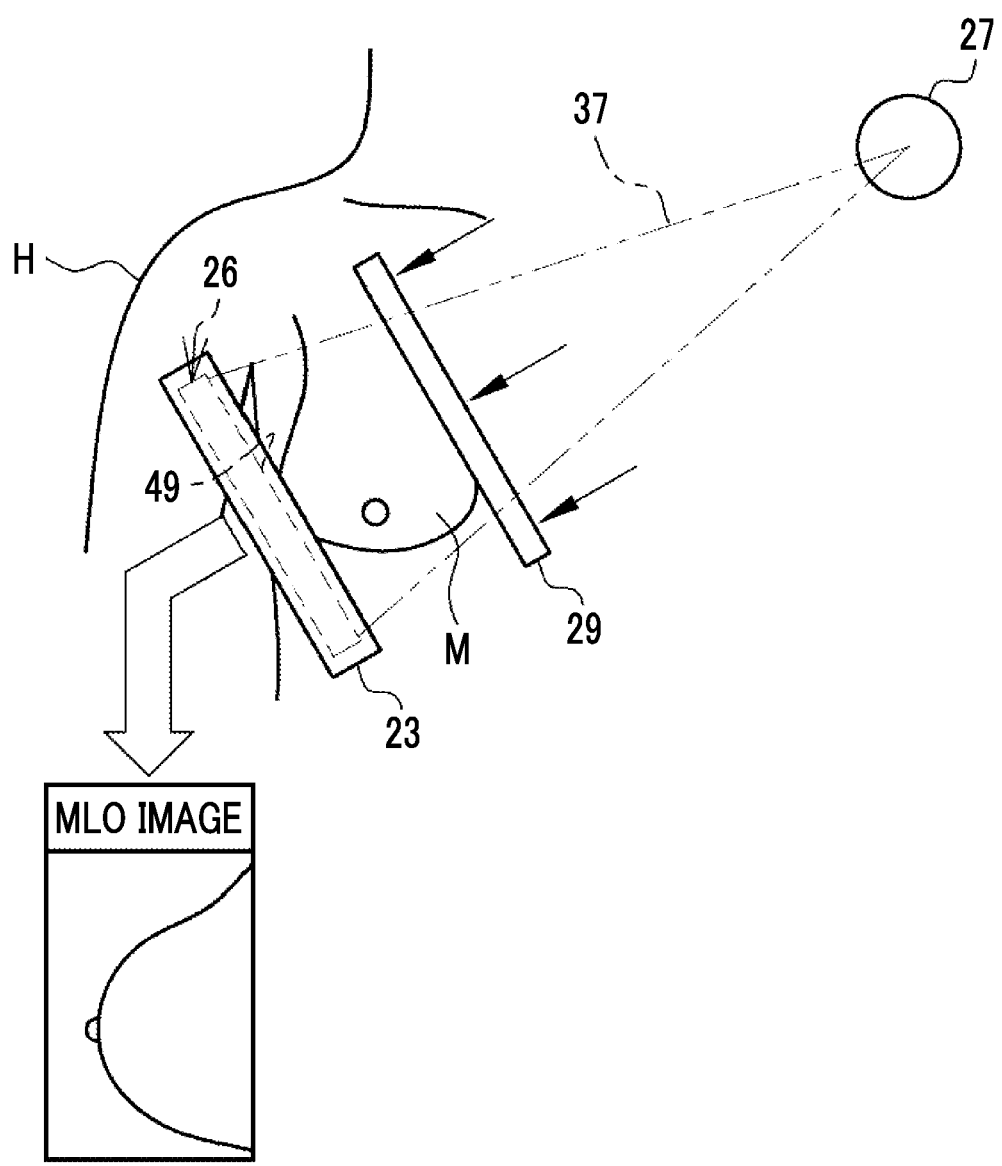
FIG. 7 is a diagram illustrating an aspect of MLO imaging.

FIGS. 6 and 7 illustrate a method for capturing an image of the breast M in the mammography apparatus 10. FIG. 6 illustrates craniocaudal view (CC) imaging and FIG. 7 illustrates mediolateral oblique view (MLO) imaging. The CC imaging is an imaging method which captures an image while compressing the breast M interposed between the detector accommodation portion 23 and the compression plate 29 in the vertical direction. In this case, the radiation detector 26 outputs a CC image as the projection image. In contrast, the MLO imaging is an imaging method which captures an image while compressing the breast M interposed between the detector accommodation portion 23 and the compression plate 29 at an inclination angle of about 60°. In this case, the radiation detector 26 outputs an MLO image as the projection image. In addition, FIGS. 6 and 7 illustrate only one radiation tube 27 for simplicity of illustration. Further, FIGS. 6 and 7 illustrate the right breast M. Of course, the image of the left breast M can be captured.

Figure 8:
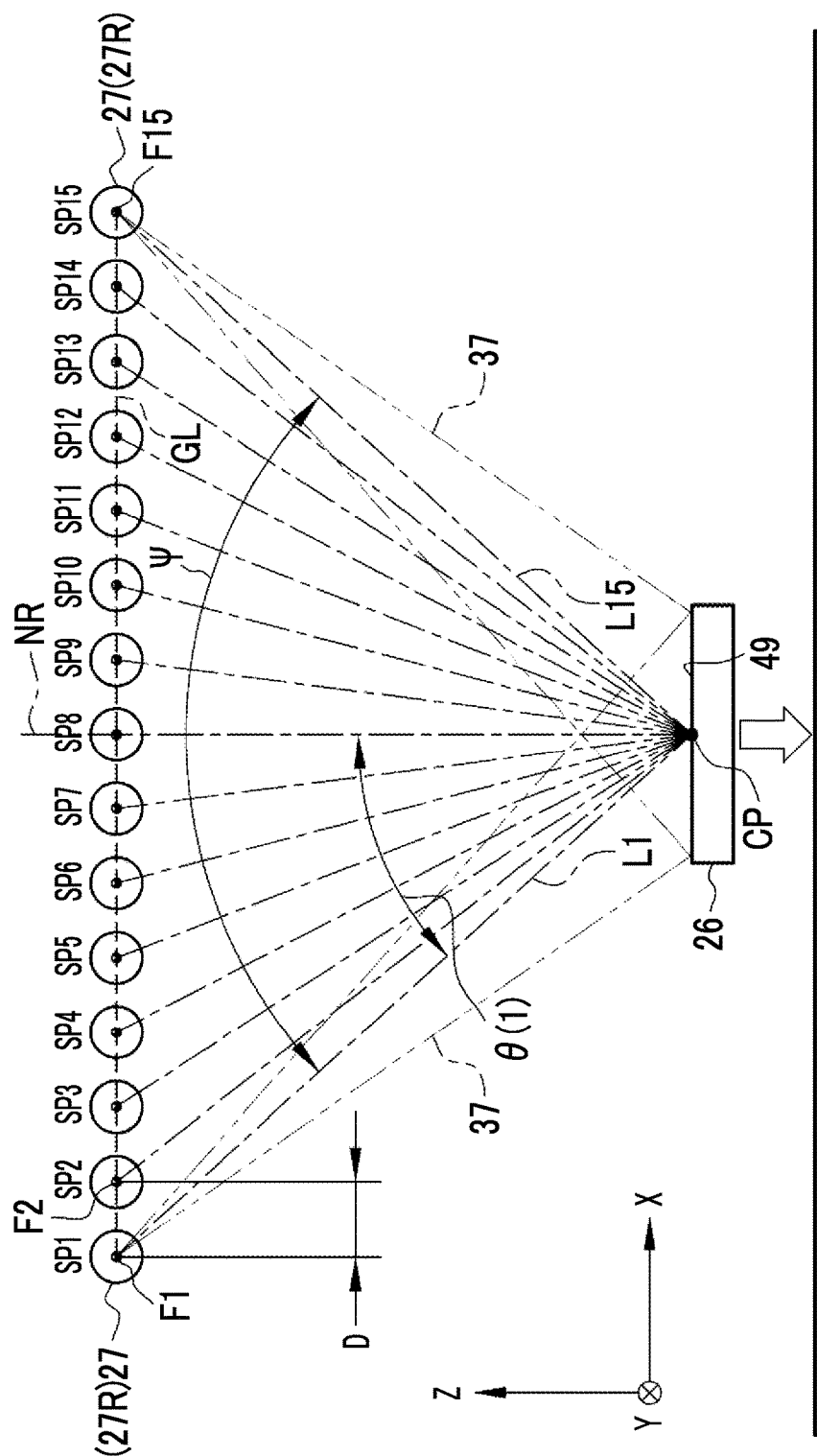
FIG. 8 is a diagram illustrating an aspect of tomosynthesis imaging.

In FIG. 8 which is a plan view illustrating the radiation source 25 and the radiation detector 26 as viewed from the support 20B, it is assumed that the direction of a normal line to the imaging surface 49 is the Z direction, a direction along a side of the imaging surface 49 is the X direction, and a depth direction of the imaging surface 49 which is perpendicular to the Z direction and the X direction is the Y direction. The radiation tubes 27 are provided at a total of 15 positions SP1, SP2, SP14, and SP15 where the radiation 37 is emitted to the imaging surface 49 at different irradiation angles. The focuses F1 to F15 of the radiation 37 in the radiation tubes 27 at the positions SP1 to SP15 are linearly arranged at equal intervals D. Further, the position SP8 is disposed on a normal line NR to the imaging surface 49 which extends from a center point CP of the side of the imaging surface 49 in the X direction. Positions other than the position SP8 are set so as to be bilaterally symmetric with respect to the normal line NR such that the positions SP1 to SP7 are disposed on the left side of the normal line NR and the positions SP9 to SP15 are disposed on the right side of the normal line NR. That is, the radiation tubes 27 at the positions SP1 to SP7 and the radiation tubes 27 at the positions SP9 to SP15 are disposed at positions that are symmetric with respect to a line.

Here, a straight line GL on which the positions SP1 to SP15 are set is parallel to the side of the imaging surface 49 along the X direction in a plan view of the radiation source 25 and the radiation detector 26 from the Z direction. The straight line GL is offset to the front side (a side opposite to the support 20B) in the Y direction. The present disclosure is not limited to a case in which the intervals D between the focuses F1 to F15 are exactly equal to each other. For example, an error of ±5% is allowed in the interval D.

The irradiation angle of the radiation 37 is an angle formed between the normal line NR and a line connecting the center point CP and each of the focuses F1 to F15 of the radiation 37 in the radiation tubes 27 at the positions SP1 to SP15. Therefore, the irradiation angle at the position SP8 aligned with the normal line NR is 0°. FIG. 8 illustrates a line L1 connecting the focus F1 at the position SP1 and the center point CP and an irradiation angle θ(1) formed between the normal line NR and the line L1 as an example.

An angle represented by a symbol Ψ is the maximum scanning angle of tomosynthesis imaging. The maximum scanning angle Ψ is defined by the positions SP1 and SP15 at both ends among the positions SP1 to SP15. Specifically, the maximum scanning angle Ψ is an angle formed between the line L1 connecting the focus F1 at the position SP1 and the center point CP and a line L15 connecting the focus F15 at the position SP15 and the center point CP.

The maximum scanning angle Ψ is the range of the minimum irradiation angle required to generate the tomographic image T (see FIG. 9) with a preset resolution level. At the maximum scanning angle Ψ, the radiation tubes 27 at the outermost positions SP1 and SP15 are irradiation essential radiation tubes 27R from which the emission of the radiation 37 is essential to generate the tomographic image T with a preset resolution level. The radiation tubes 27 at the positions SP1 and SP15 are also the radiation tubes 27 disposed at both ends among the plurality of radiation tubes 27.

In one normal tomosynthesis imaging operation, each of the radiation tubes 27 at the positions SP1 to SP15 is operated to emit the radiation 37 to the breast M at each of the positions SP1 to SP15. The radiation detector 26 detects the radiation 37 emitted at each of the positions SP1 to SP15 whenever the radiation 37 is emitted and outputs projection images at the positions SP1 to SP15. The tomosynthesis imaging can be performed by both the CC imaging method illustrated in FIG. 6 and the MLO imaging method illustrated in FIG. 7. In the case of simple imaging in which the CC imaging illustrated in FIG. 6 and the MLO imaging illustrated in FIG. 7 are independently performed, only the radiation tube 27 disposed at the position SP8 where the irradiation angle is 0° is operated.

Figure 9:
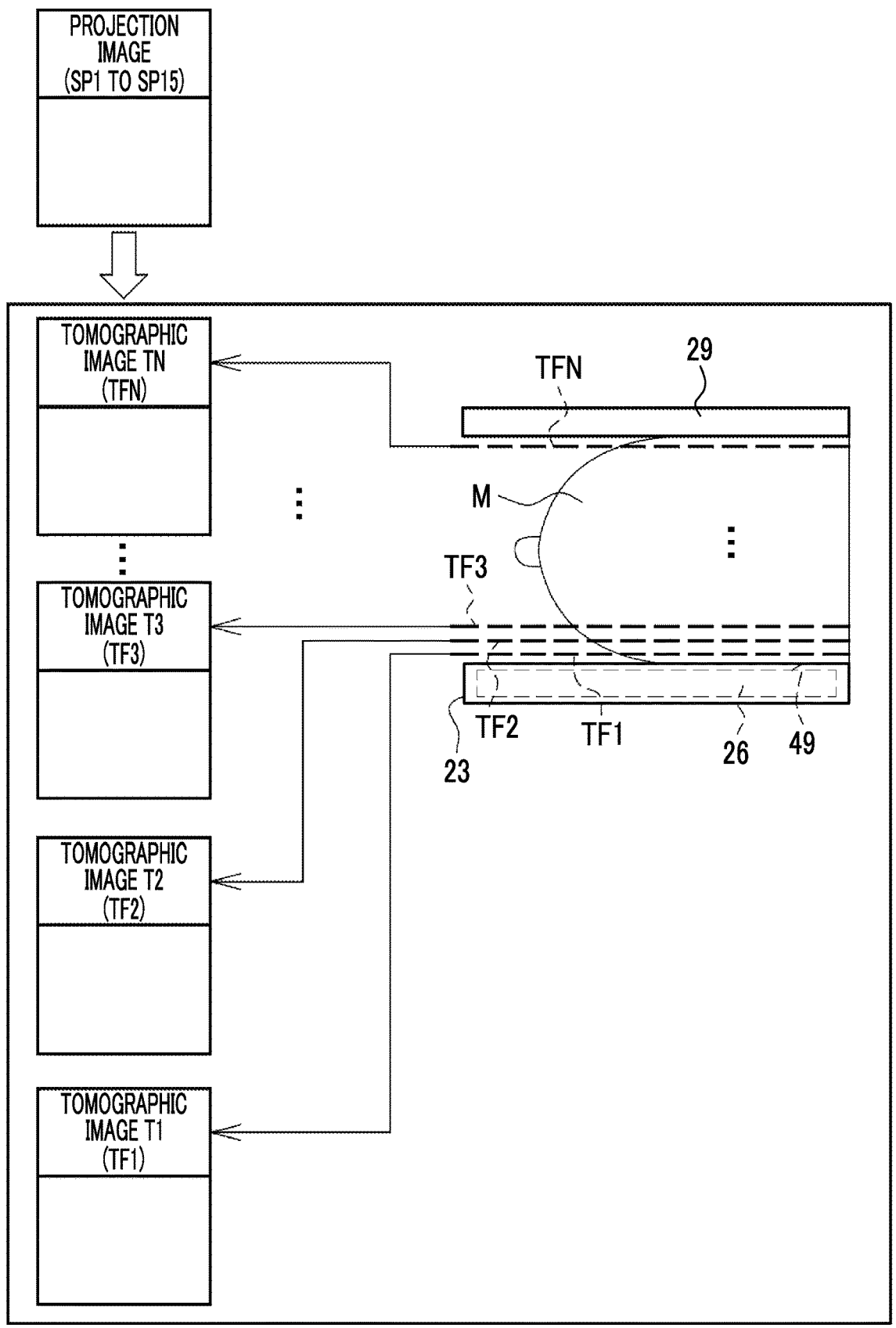
FIG. 9 is a diagram illustrating an aspect in which tomographic images are generated from a plurality of projection images obtained by the tomosynthesis imaging.

As illustrated in FIG. 9, in general, the mammography apparatus 10 generates tomographic images T1 to TN corresponding to any tomographic planes TF1 to TFN of the breast M from a plurality of projection images at the plurality of positions SP1 to SP15 obtained by the tomosynthesis imaging illustrated in FIG. 8. The mammography apparatus 10 generates the tomographic images T1 to TN using a known method such as a filtered back projection method. The tomographic images T1 to TN are images in which structures in the tomographic planes TF1 to TFN have been highlighted.

Figure 10:
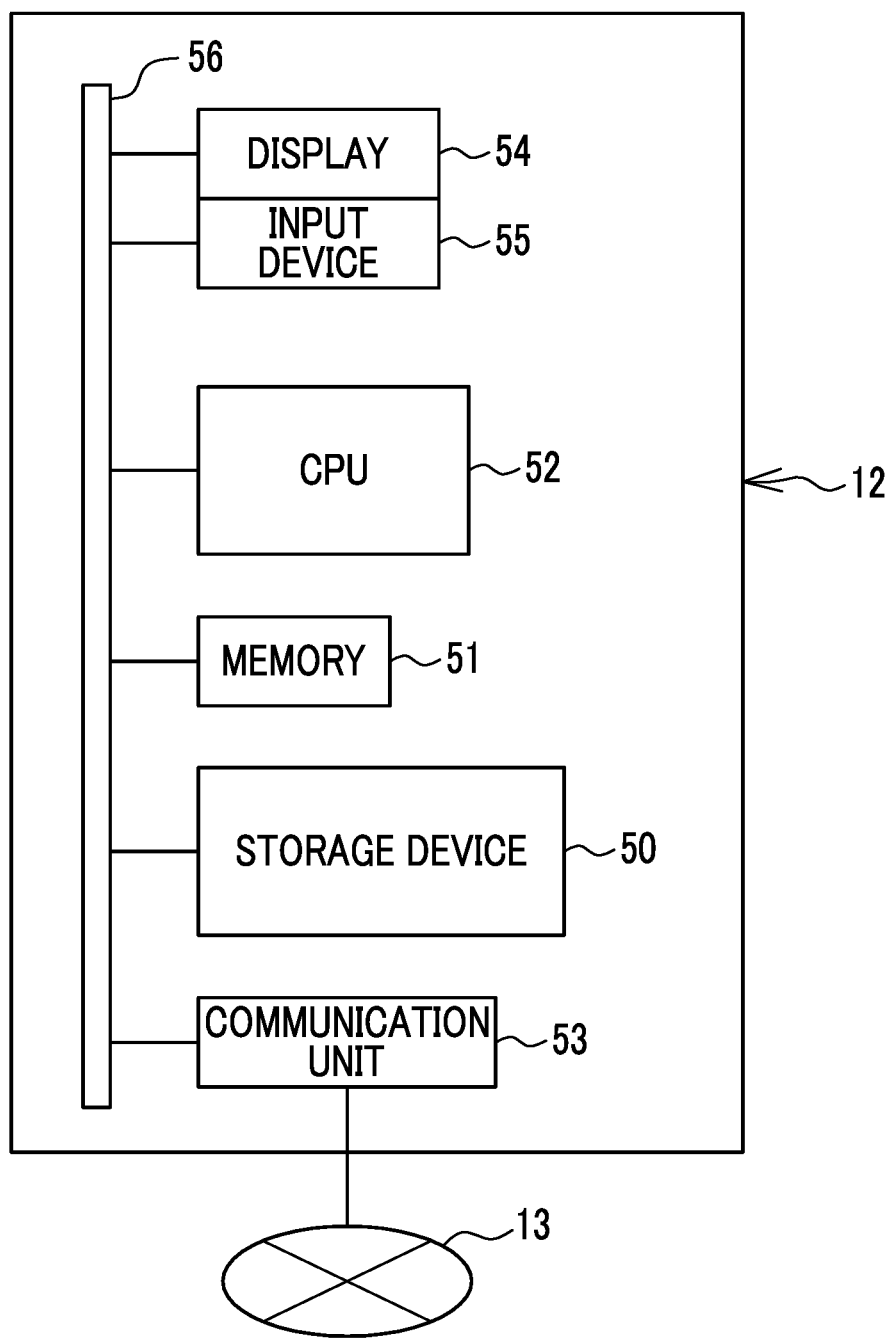
FIG. 10 is a block diagram illustrating a computer forming a control device.

In FIG. 10, the computer forming the control device 12 comprises a storage device 50, a memory 51, a central processing unit (CPU) 52, a communication unit 53, a display 54, and an input device 55. These units are connected to each other through a bus line 56.

The storage device 50 is a hard disk drive that is provided in the computer forming the control device 12 or is connected to the computer through a cable or a network. Alternatively, the storage device 50 is a disk array in which a plurality of hard disk drives are connected. The storage device 50 stores a control program, such as an operating system, various application programs, and various kinds of data associated with these programs. In addition, a solid state drive may be used instead of the hard disk drive.

The memory 51 is a work memory used by the CPU 52 to perform processes. The CPU 52 loads the program stored in the storage device 50 to the memory 51 and performs a process corresponding to the program to control the overall operation of each unit of the computer.

The communication unit 53 is a network interface that controls the transmission of various kinds of information through the network 13. The display 54 displays various screens. The various screens have operation functions by a graphical user interface (GUI). The computer forming the control device 12 receives the input of operation commands from the input device 55 through various screens. The input device 55 is, for example, a keyboard, a mouse, or a touch panel.

Figure 11:
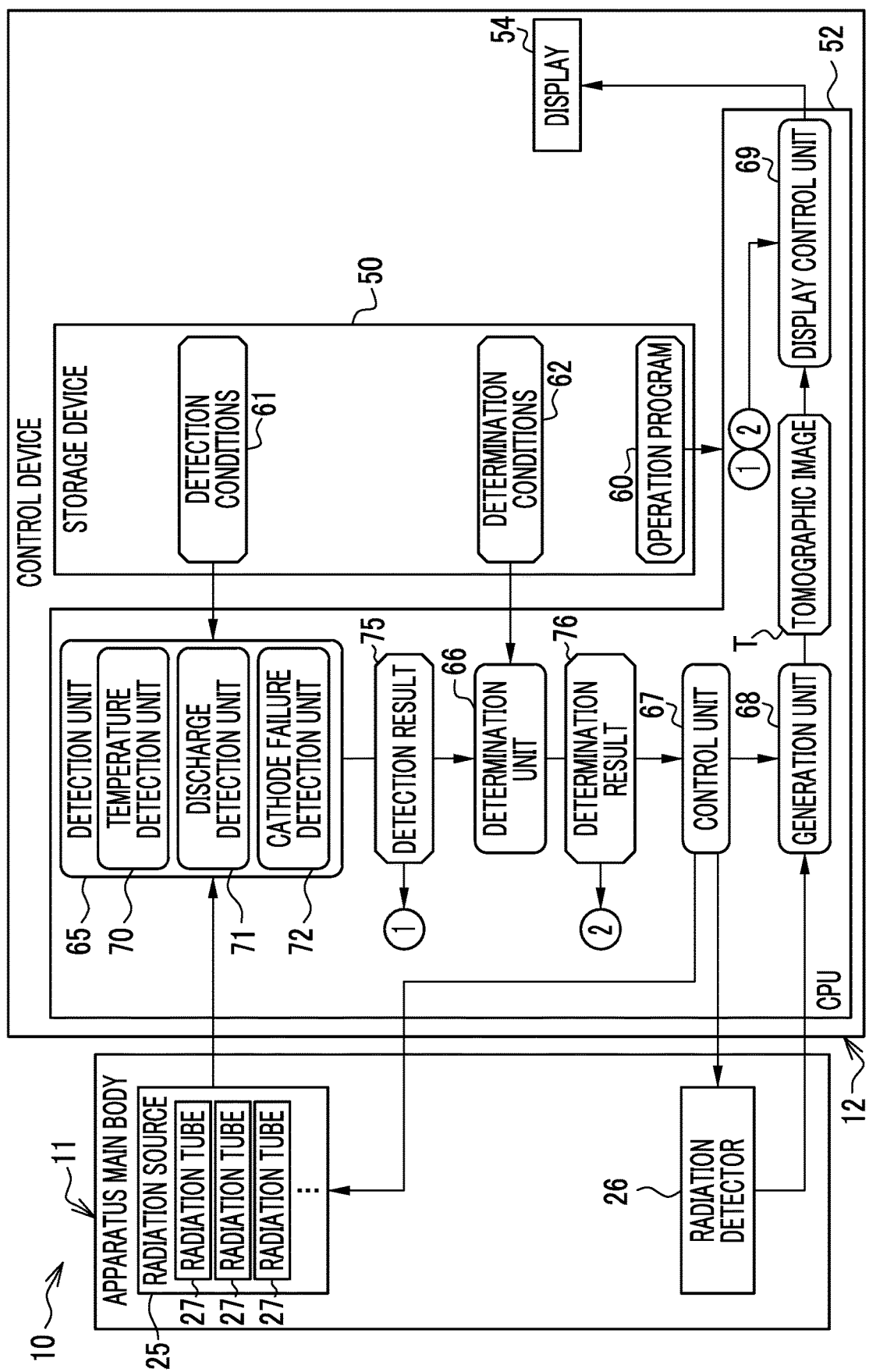
FIG. 11 is a block diagram mainly illustrating a processing unit of a CPU of the control device.

In FIG. 11, an operation program 60 is stored in the storage device 50 of the control device 12. The operation program 60 is an application program for causing the computer to function as the control device 12. That is, the operation program 60 is an example of a "program for operating a tomosynthesis imaging control device" according to the technology of the present disclosure. The storage device 50 stores detection conditions 61 and determination conditions 62 in addition to the operation program 60.

In a case in which the operation program 60 is started, the CPU 52 of the control device 12 functions as a detection unit 65, a determination unit 66, the control unit 67, a generation unit 68, and a display control unit 69 in cooperation with, for example, the memory 51. The detection unit 65 includes a temperature detection unit 70, a discharge detection unit 71, and a cathode failure detection unit 72. The "detection unit 65" described below is a concept including the temperature detection unit 70, the discharge detection unit 71, and the cathode failure detection unit 72.

The detection unit 65 detects the state of each of the plurality of radiation tubes 27 with reference to the detection conditions 61. Specifically, the detection unit 65 determines whether the state of each of the radiation tubes 27 is a normal state in which a proper amount of radiation 37 satisfying the set irradiation conditions can be emitted or an abnormal state that the proper amount of radiation 37 is not capable of being emitted. The detection unit 65 outputs a detection result 75 to the determination unit 66 and the display control unit 69. The irradiation conditions include a tube voltage applied to the radiation tube 27 and a tube current-time product.

The determination unit 66 receives the detection result 75 from the detection unit 65. The determination unit 66 determines whether or not to permit the generation of the tomographic image T on the basis of the detection result 75 with reference to the determination conditions 62. The determination unit 66 outputs a determination result 76 to the control unit 67 and the display control unit 69.

The control unit 67 controls the operation of the radiation source 25 and the radiation detector 26. Further, the control unit 67 receives the determination result 76 from the determination unit 66. The control unit 67 controls the operation of the generation unit 68 according to the determination result 76. That is, the control unit 67 is an example of a "first control unit" according to the technology of the present disclosure.

The control unit 67 operates each of the radiation tubes 27 in the radiation source 25 to perform the tomosynthesis imaging illustrated in FIG. 8. Then, the control unit 67 outputs a plurality of projection images detected by the radiation detector 26 from the radiation detector 26 to the generation unit 68.

In a case in which the determination result 76 indicates that the generation of the tomographic image T is permitted, the generation unit 68 generates the tomographic image T on the basis of the plurality of projection images from the radiation detector 26 under the control of the control unit 67, as illustrated in FIG. 9. The generation unit 68 outputs the tomographic image T to the display control unit 69. On the other hand, in a case in which the determination result 76 indicates that the generation of the tomographic image T is not permitted, the generation unit 68 does not generate the tomographic image T.

The display control unit 69 receives the detection result 75 from the detection unit 65, receives the determination result 76 from the determination unit 66, and receives the tomographic image T from the generation unit 68. The display control unit 69 performs control to generate various screens corresponding to the received various kinds of data and to display the generated various screens on the display 54.

The temperature detection unit 70 detects an abnormality in each radiation tube 27 caused by temperature. The temperature detection unit 70 converts, for example, the irradiation conditions set for each radiation tube 27 into the amount of heat generated by the emission of the radiation 37. Then, whenever the radiation 37 is emitted, the calculated amount of heat is accumulated and added to calculate the amount of heat of each radiation tube 27 and the calculated amount of heat is converted into temperature. The temperature detection unit 70 subtracts the amount of heat dissipated by natural cooling during the emission of the radiation 37 from each radiation tube 27 in order to improve accuracy. A temperature sensor may be provided in the vicinity of each radiation tube 27 in the housing 28 filled with insulating oil and the temperature of the insulating oil measured by the temperature sensor or temperature converted from the temperature of the insulating oil measured by the temperature sensor may be detected as the temperature of each radiation tube 27. Alternatively, the anode 36 may be grounded, a thermistor may be connected to the anode 36, and the output of the thermistor may be detected as the temperature of each radiation tube 27.

The discharge detection unit 71 detects an abnormality in each radiation tube 27 due to discharge. The discharge detection unit 71 detects discharge by detecting, for example, an excessive tube current caused by the discharge or a sharp decrease in the tube voltage caused by the discharge. In addition, the discharge may be detected by detecting an excessive focusing voltage of the focusing electrode 48 caused by the discharge.

The cathode failure detection unit 72 detects an abnormality caused by the failure of the cathode 35 in each radiation tube 27. The cathode failure detection unit 72 detects the failure of the cathode 35 by detecting, for example, an excessively high voltage applied to the gate electrode 47 due to the failure of the cathode 35. In a case in which the cathode 35 is not a cold cathode illustrated in the example and has a filament structure that emits thermoelectrons, the cutting of the filament may be detected to detect the failure of the cathode 35.

The temperature of each radiation tube 27 can be detected before the operation of each radiation tube 27. On the other hand, the discharge of each radiation tube 27 and the failure of the cathode 35 in each radiation tube 27 can be detected only after each radiation tube 27 is operated in terms of its nature. Therefore, the temperature detection unit 70, the discharge detection unit 71, and the cathode failure detection unit 72 perform detection at different timings. Specifically, the detection timings are as illustrated in a table 80 of FIG. 12. That is, the temperature detection unit 70 detects an abnormality in each radiation tube 27 caused by temperature before each radiation tube 27 is operated in the tomosynthesis imaging and the discharge detection unit 71 and the cathode failure detection unit 72 detect an abnormality caused by discharge and an abnormality caused by the failure of the cathode 35, respectively, after each radiation tube 27 is operated in the tomosynthesis imaging.

As illustrated in FIG. 13, a state corresponding to the detection content of each of detection targets, such as the temperature and discharge of each radiation tube 27 and the failure of the cathode 35, is registered in the detection conditions 61. For the temperature as the detection target, a normal state is registered in a case in which the temperature is less than a temperature threshold value and an abnormal state is registered in a case in which the temperature is greater than the temperature threshold value. Therefore, the temperature detection unit 70 detects that the radiation tube 27 is in the normal state in a case in which the detected temperature is less than the temperature threshold value. On the other hand, the temperature detection unit 70 detects that the radiation tube 27 is in the abnormal state in a case in which the detected temperature is greater than the temperature threshold value. In addition, in this example, as described in the remarks, the temperature that reaches the service temperature of the radiation tube 27 in a case in which the radiation 37 is consecutively emitted five times is set as the temperature threshold value. The service temperature is, for example, 60° C. and the temperature threshold value is, for example, 55° C.

For the discharge as the detection target, a normal state is registered in a case in which the number of occurrences of discharge is less than a number-of-times threshold value and an abnormal state is registered in a case in which the number of occurrences of discharge is equal to or greater than the number-of-times threshold value. Therefore, the discharge detection unit 71 detects that the radiation tube 27 is in the normal state in a case in which the detected number of occurrences of discharge is less than the number-of-times threshold value. On the other hand, the discharge detection unit 71 detects that the radiation tube 27 is in the abnormal state in a case in which the detected number of occurrences of discharge is equal or greater than the number-of-times threshold value. In this example, the number-of-times threshold value is set to 1 as described in the remarks. That is, in this example, the discharge detection unit 71 detects that the radiation tube 27 is in the abnormal state in a case in which discharge occurs even once.

For the failure of the cathode 35 as the detection target, a normal state is registered in a case in which a failure has not occurred in the cathode 35 and an abnormal state is registered in a case in which a failure has occurred in the cathode 35. Therefore, the cathode failure detection unit 72 detects that the radiation tube 27 is in the normal state in a case in which the failure of the cathode 35 has not been detected. On the other hand, the cathode failure detection unit 72 detects that the radiation tube 27 is in the abnormal state in a case in which the failure of the cathode 35 has been detected.

As illustrated in FIG. 14, whether or not to generate the tomographic images T corresponding to two patterns of the detection results 75 is registered in the determination conditions 62. That is, data indicating that the generation of the tomographic image T is permitted is registered in a case (hereinafter, referred to as a first pattern) in which the detection result 75 indicates that the irradiation essential radiation tube 27R is in the normal state and the number of radiation tubes 27 in the normal state including the irradiation essential radiation tubes 27R is equal to or greater than a preset minimum required number of radiation tubes. On the other hand, data indicating that the generation of the tomographic image T is not permitted is registered in a case (hereinafter, referred to as a second pattern) in which the detection result 75 indicates that the irradiation essential radiation tube 27R is in the abnormal state or the detection result 75 indicates that the number of radiation tubes 27 in the abnormal state except the irradiation essential radiation tube 27R is greater than a preset maximum allowable number of radiation tubes. In this example, as described in the remarks, 10 radiation tubes are registered as the minimum required number of radiation tubes and 5 radiation tubes are registered as the maximum allowable number of radiation tubes.

Figure 15:
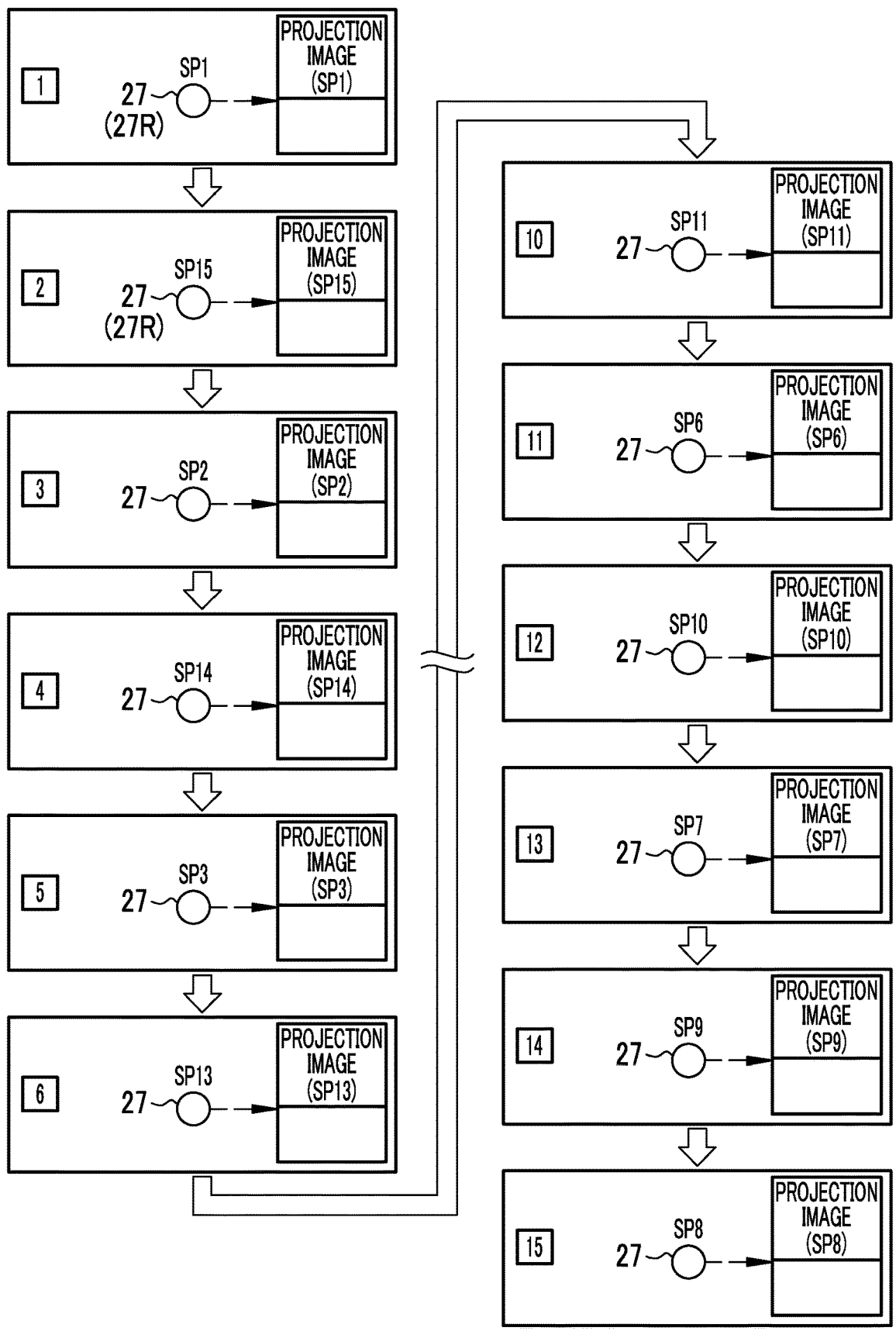
FIG. 15 is a diagram illustrating an operation order of each radiation tube in the tomosynthesis imaging.

As illustrated in FIG. 15, the control unit 67 alternately operates the plurality of radiation tubes 27 in the left and right directions from both ends such that the radiation tube 27 at the position SP1 is operated first, the radiation tube 27 at the position SP15 is operated second, the radiation tube 27 at the position SP2 is operated third, the radiation tube 27 at the position SP14 is operated fourth, . . . , the radiation tube 27 at the position SP7 is operated thirteenth, the radiation tube 27 at the position SP9 is operated fourteenth, and the radiation tube 27 at the position SP8 is operated fifteenth. The radiation tube 27 at the position SP1 which is operated first and the radiation tube 27 at the position SP15 which is operated second are the irradiation essential radiation tubes 27R as described above. Therefore, the discharge detection unit 71 can detect whether or not the number of occurrences of discharge has reached the number-of-times threshold value in the irradiation essential radiation tube 27R earlier than other radiation tubes 27. Similarly, the cathode failure detection unit 72 can detect whether or not a failure has been recognized in the cathode 35 of the irradiation essential radiation tube 27R earlier than other radiation tubes 27. That is, the control unit 67 is an example of a "second control unit" according to the technology of the present disclosure. In FIG. 15, an operation order is indicated by numbers enclosed in squares. For example, this holds for FIG. 30.

As illustrated in FIG. 16, the states related to the temperature, discharge, and cathode failure of each radiation tube 27 are registered in the detection result 75. In addition, No. 1 to No. 15 which are numbers corresponding to the positions SP1 to SP15 are given to the radiation tubes 27. The radiation tube 27 at the position SP1 and the radiation tube 27 at the position SP15, which are the irradiation essential radiation tubes 27R, are hatched so as to be distinguished from the other radiation tubes. This holds for the subsequent diagrams.

FIG. 16 illustrates a case in which a total of three radiation tubes 27, that is, the radiation tube 27 at the position SP2, the radiation tube 27 at the position SP7, and the radiation tube 27 at the position SP12 are detected to be in the abnormal state. FIG. 16 illustrates a case in which the radiation tube 27 at the position SP2 is detected to be abnormal due to discharge and the radiation tube 27 at the position SP7 and the radiation tube 27 at the position SP12 are detected to be abnormal due to temperature. For the radiation tube 27 at the position SP7 and the radiation tube 27 at the position SP12 whose temperature has been detected to be abnormal, the state thereof due to discharge and a cathode failure is not detected (does not need to detected). Therefore, "–" meaning indefiniteness is registered in the temperature and cathode fields. In the case of the detection result 75 illustrated in FIG. 16, the irradiation essential radiation tube 27R is in the normal state and the number of radiation tubes 27 in the normal state including the irradiation essential radiation tube 27R and the radiation tubes other than the irradiation essential radiation tube 27R is 12 and is greater than 10 that is the minimum required number of radiation tubes. Therefore, the determination unit 66 determines to permit the generation of the tomographic image T.

Figure 17:
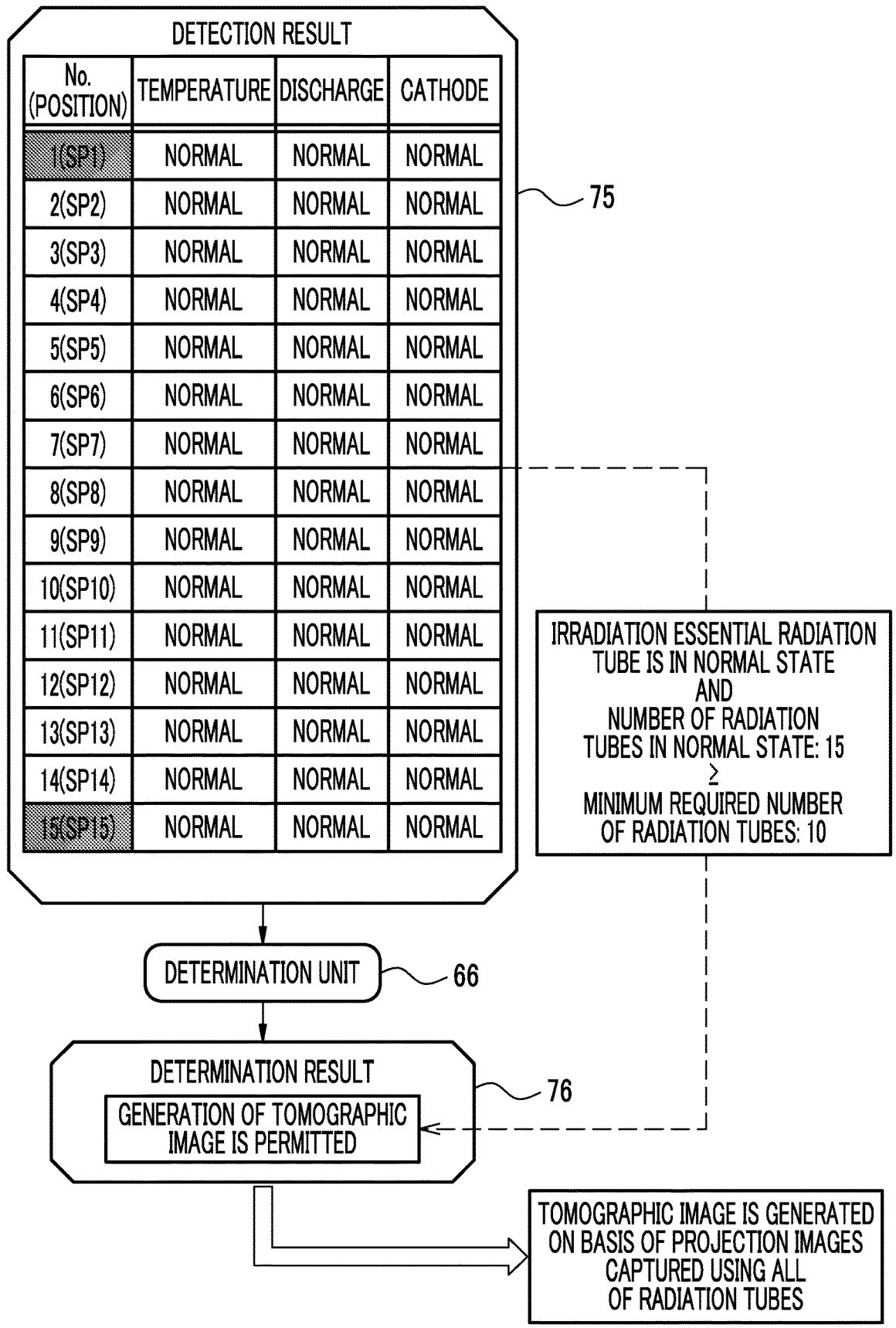
FIG. 17 is a diagram illustrating an example of a detection result and a determination result.
Figure 18:
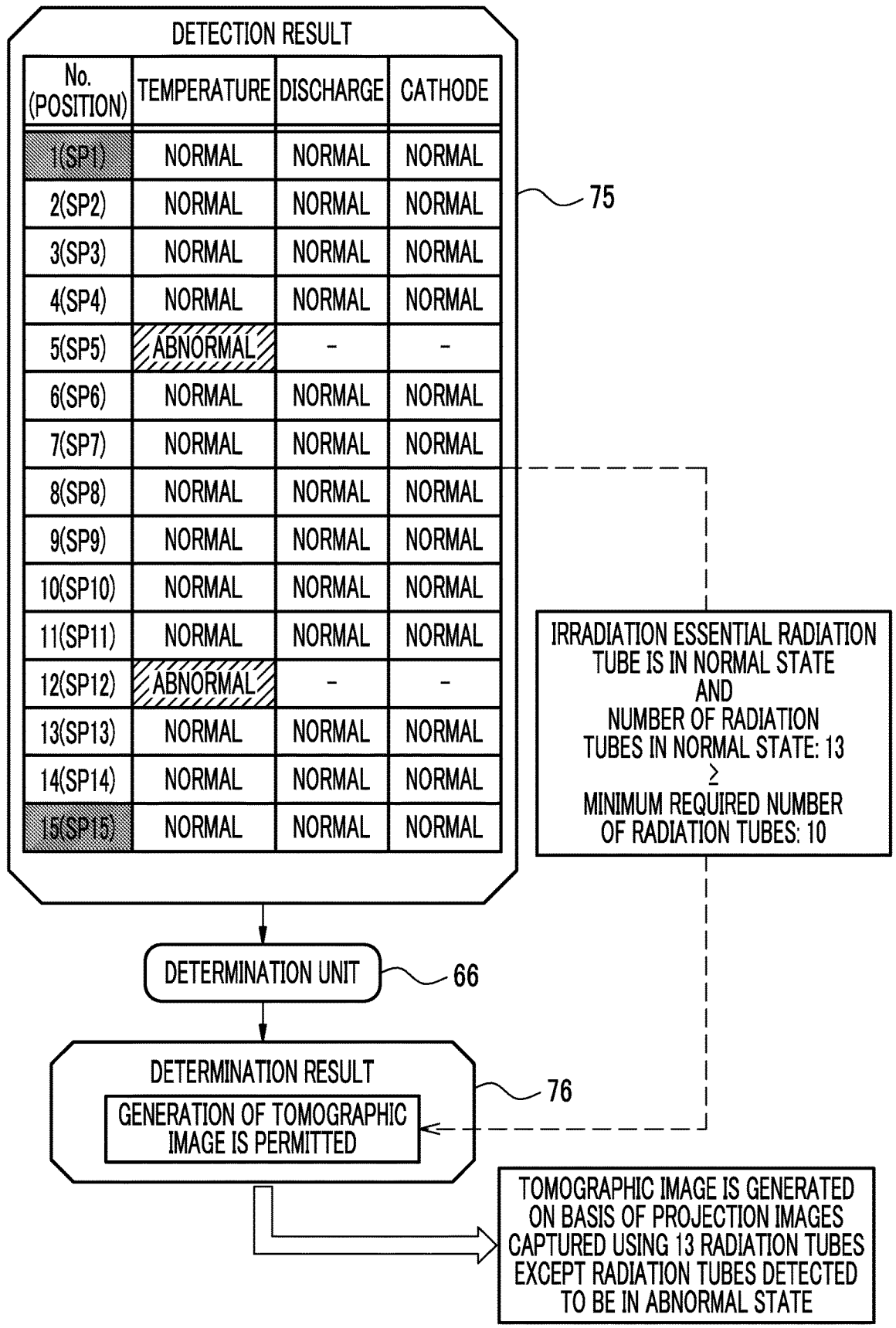
FIG. 18 is a diagram illustrating an example of a detection result and a determination result.
Figure 19:
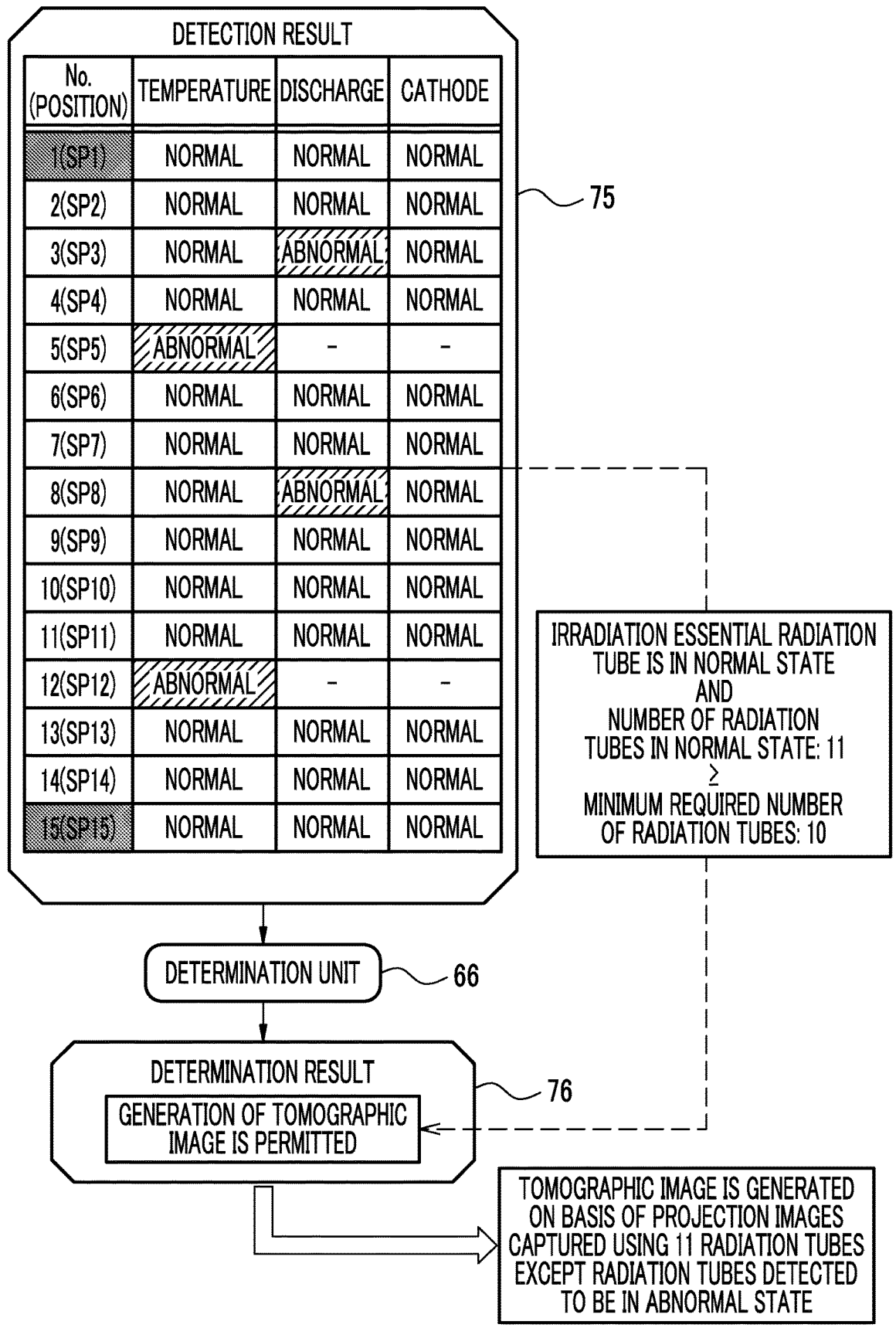
FIG. 19 is a diagram illustrating an example of a detection result and a determination result.

FIGS. 17 to 23 illustrate various variations in the detection result 75 and the determination result 76. FIGS. 17 to 19 illustrate a case in which the detection result 75 is the first pattern and the determination result 76 indicates that the generation of the tomographic image T is permitted. FIGS. 20 to 23 illustrate a case in which the detection result 75 is the second pattern and the determination result 76 indicates that the generation of the tomographic image T is not permitted.

The detection result 75 illustrated in FIG. 17 shows a case in which the detection unit 65 has not detected any radiation tube 27 in the abnormal state. That is, the irradiation essential radiation tube 27R is in the normal state and the number of radiation tubes 27 in the normal state including the irradiation essential radiation tube 27R and the radiation tubes other than the irradiation essential radiation tube 27R is 15 and is greater than 10 that is the minimum required number of radiation tubes. Therefore, this corresponds to the first pattern. Therefore, in this case, the determination unit 66 outputs the determination result 76 indicating that the generation of the tomographic image T is permitted. The generation unit 68 generates the tomographic image T on the basis of the projection images captured using all of the 15 radiation tubes 27.

The detection result 75 illustrated in FIG. 18 shows a case in which a total of two radiation tubes 27, that is, the radiation tube 27 at the position SP5 and the radiation tube 27 at the position SP12 have been detected to be abnormal due to the temperature and the other radiation tubes 27 have been detected to be normal. That is, the irradiation essential radiation tube 27R is in the normal state and the number of radiation tubes 27 in the normal state including the irradiation essential radiation tube 27R and the radiation tubes other than the irradiation essential radiation tube 27R is 13 and is greater 10 that is the minimum required number of radiation tubes. Therefore, this corresponds to the first pattern. Therefore, in this case, the determination unit 66 outputs the determination result 76 indicating that the generation of the tomographic image T is permitted, as in the case of FIG. 17. The generation unit 68 generates the tomographic image T on the basis of the projection images captured using 13 radiation tubes 27 other than the radiation tube 27 at the position SP5 and the radiation tube 27 at the position SP12.

The detection result 75 illustrated in FIG. 19 shows a case in which a total of two radiation tubes 27, that is, the radiation tube 27 at the position SP5 and the radiation tube 27 at the position SP12 have been detected to be abnormal state due to the temperature. Further, the detection result 75 shows a case in which a total of two radiation tubes 27, that is, the radiation tube 27 at the position SP3 and the radiation tube 27 at the position SP8 are detected to be abnormal due to the discharge. That is, the irradiation essential radiation tube 27R is in the normal state and the number of radiation tubes 27 in the normal state including the irradiation essential radiation tube 27R and the radiation tubes other than the irradiation essential radiation tube 27R is 11 and is greater than 10 that is the minimum required number of radiation tubes. Therefore, this corresponds to the first pattern. Therefore, in this case, the determination unit 66 outputs the determination result 76 indicating that the generation of the tomographic image T is permitted, as in the case of FIGS. 17 and 18. The generation unit 68 generates the tomographic image T on the basis of the projection images captured using 11 radiation tubes 27 other than the radiation tube 27 at the position SP3, the radiation tube 27 at the position SP5, the radiation tube 27 at the position SP8, and the radiation tube 27 at the position SP12.

Since the radiation tube 27 at the position SP5 and the radiation tube 27 at the position SP12 are not operated, the projection images corresponding thereto are not output. In contrast, since the radiation tube 27 at the position SP3 and the radiation tube 27 at the position SP8 are operated and then detected to be abnormal due to the discharge, the projection images corresponding thereto are output from the radiation detector 26 once. However, the projection images are not obtained by the emission of the appropriate radiation 37. Therefore, the generation unit 68 generates the tomographic image T without using the projection images captured using the radiation tube 27 at the position SP3 and the radiation tube 27 at the position SP8.

Figure 20:
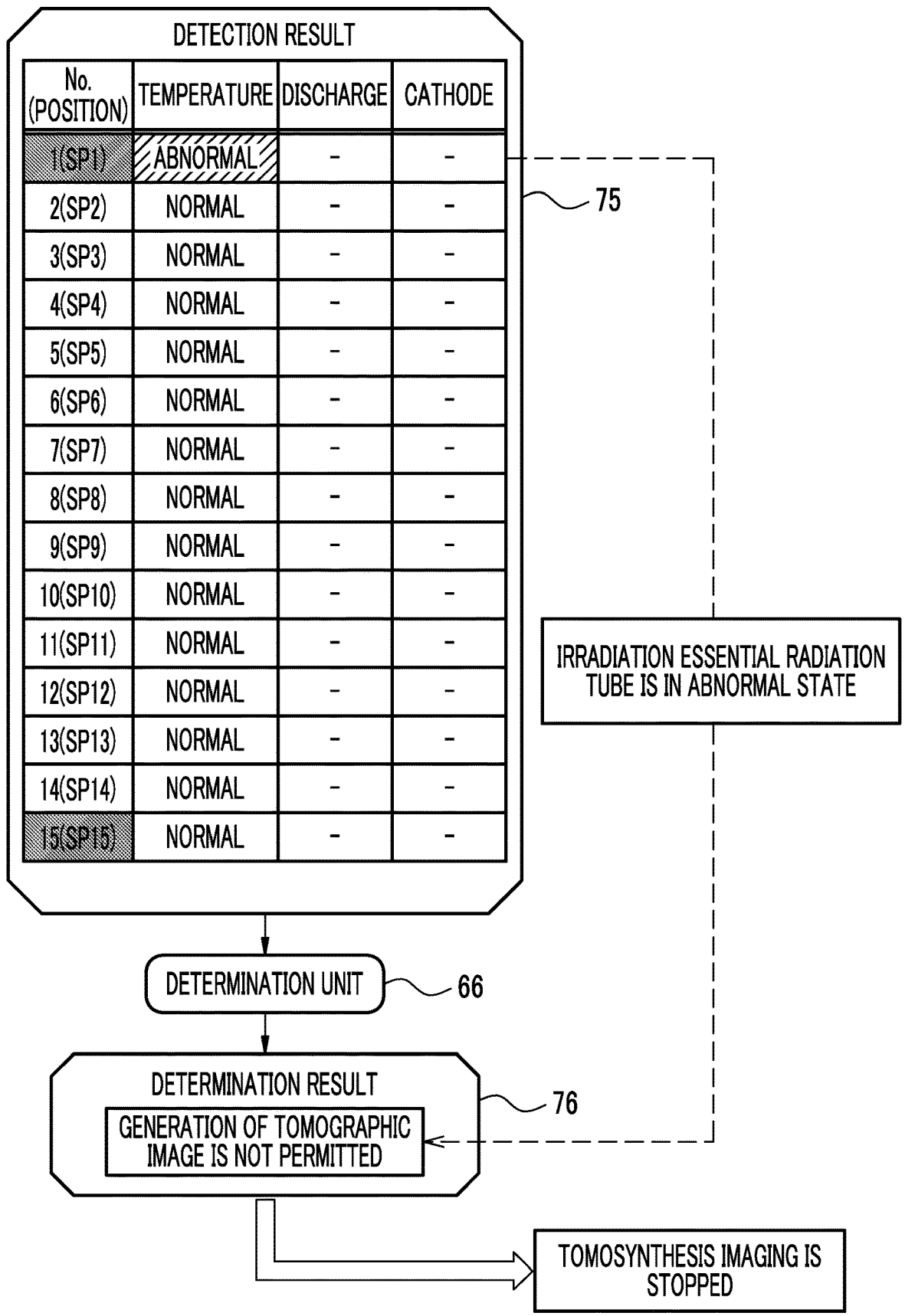
FIG. 20 is a diagram illustrating an example of a detection result and a determination result.

The detection result 75 illustrated in FIG. 20 shows a case in which the radiation tube 27 at the position SP1 which is the irradiation essential radiation tube 27R has been detected to be abnormal due to the temperature. That is, the irradiation essential radiation tube 27R is in the abnormal state. Therefore, this corresponds to the second pattern. Therefore, in this case, the determination unit 66 outputs the determination result 76 indicating that the generation of the tomographic image T is not permitted.

As illustrated in FIG. 12, the temperature detection unit 70 detects that the radiation tube 27 is abnormal due to the temperature before each radiation tube 27 is operated in the tomosynthesis imaging. Therefore, in the example illustrated in FIG. 20, the determination unit 66 outputs the determination result 76 before the tomosynthesis imaging is started. Therefore, in the example illustrated in FIG. 20, the control unit 67 stops the tomosynthesis imaging not to permit the generation of the tomographic image T.

Figure 21:
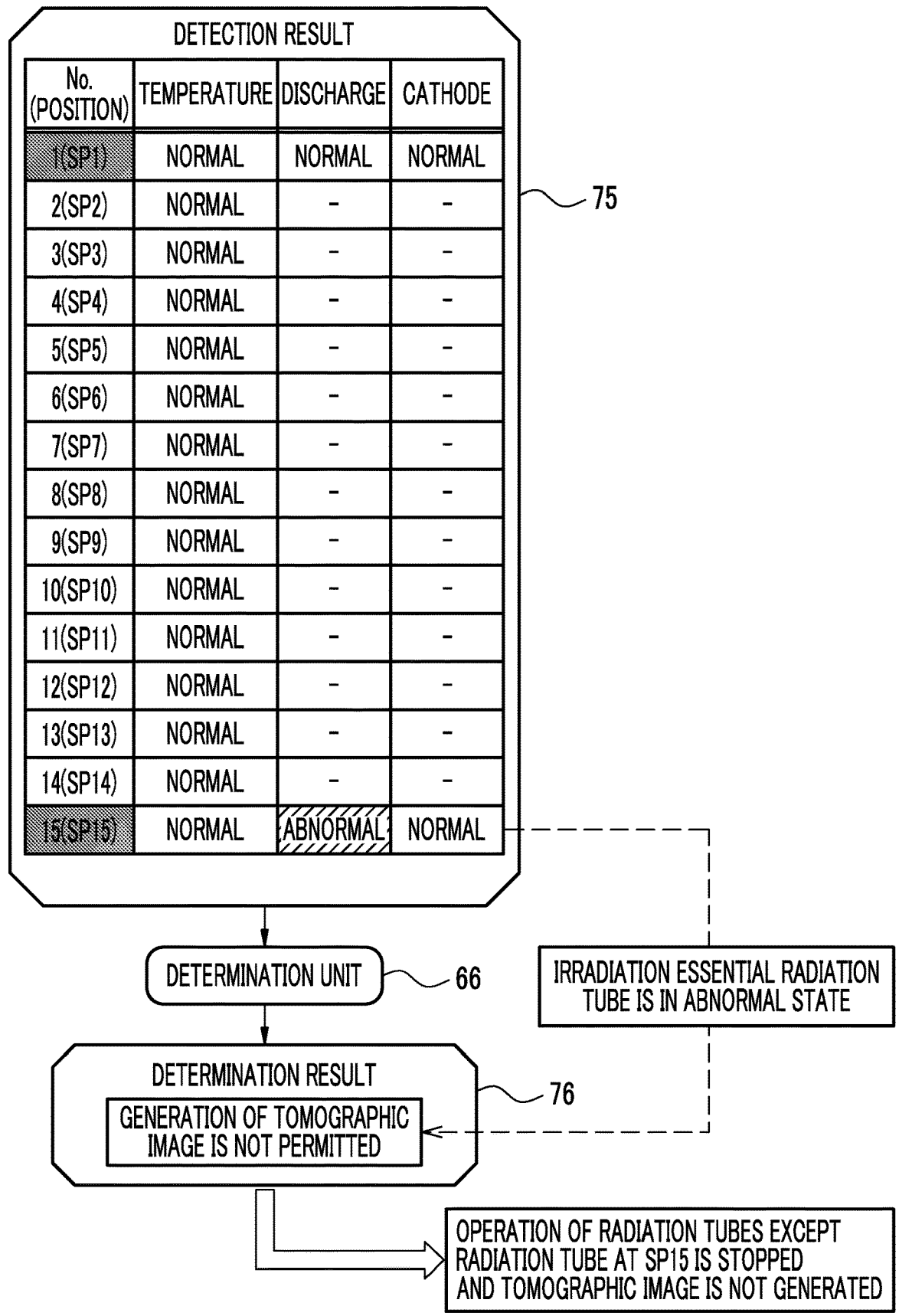
FIG. 21 is a diagram illustrating an example of a detection result and a determination result.

The detection result 75 illustrated in FIG. 21 shows a case in which the radiation tube 27 at the position SP15 which is the irradiation essential radiation tube 27R has been detected to be abnormal due to discharge. That is, the irradiation essential radiation tube 27R is in the abnormal state. Therefore, this corresponds to the second pattern. Therefore, in this case, as in the case of FIG. 20, the determination unit 66 outputs the determination result 76 indicating that the generation of the tomographic image T is not permitted.

As illustrated in FIG. 12, the discharge detection unit 71 detects that the radiation tube 27 is in the abnormal state due to discharge after each radiation tube 27 is operated in the tomosynthesis imaging. Therefore, in the example illustrated in FIG. 21, the determination unit 66 outputs the determination result 76 after the radiation tube 27 at the position SP1 and the radiation tube 27 at the position SP15 are sequentially operated. Therefore, in the example illustrated in FIG. 21, the control unit 67 stops the operation of the radiation tubes 27 after the radiation tube 27 at the position SP15 and does not direct the generation unit 68 to generate the tomographic image T.

Figure 22:
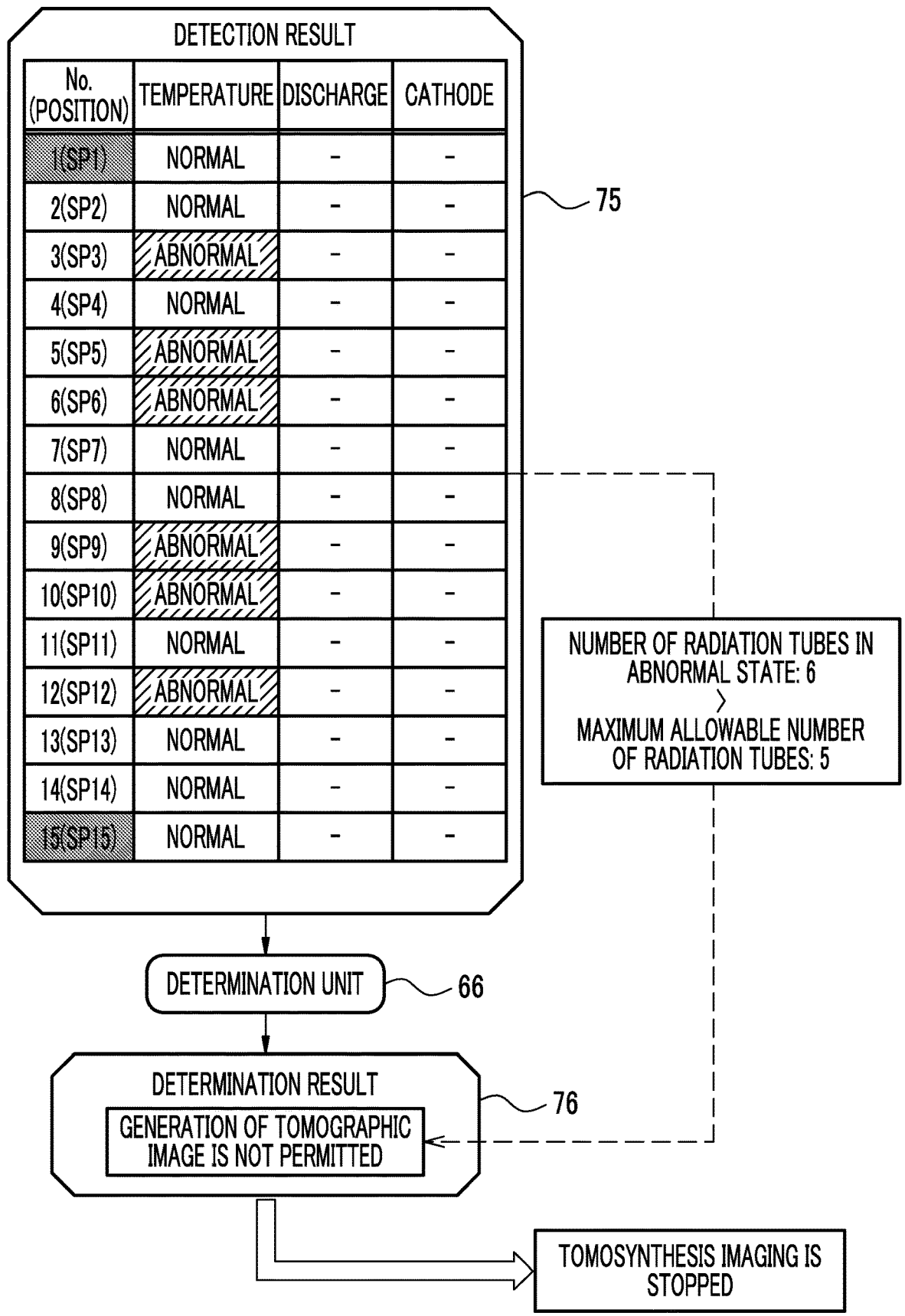
FIG. 22 is a diagram illustrating an example of a detection result and a determination result.

The detection result 75 illustrated in FIG. 22 shows a case in which a total of six radiation tubes 27, that is, the radiation tube 27 at the position SP3, the radiation tube 27 at the position SP5, the radiation tube 27 at the position SP6, the radiation tube 27 at the position SP9, the radiation tube 27 at the position SP10, and the radiation tube 27 at the position SP12 have been detected to be abnormal due to temperature. That is, the number of radiation tubes 27 in the abnormal state except the irradiation essential radiation tube 27R is 6 and is greater than 5 which is the maximum allowable number of radiation tubes. Therefore, this corresponds to the second pattern. Therefore, in this case, the determination unit 66 outputs the determination result 76 indicating that the generation of the tomographic image T is not permitted, as in the cases of FIGS. 20 and 21.

In the example illustrated in FIG. 22, the determination unit 66 outputs the determination result 76 before the tomosynthesis imaging is started, as in the example illustrated in FIG. 20. In addition, as in the example illustrated in FIG. 20, the control unit 67 stops the tomosynthesis imaging not to permit the generation of the tomographic image T.

Figure 23:
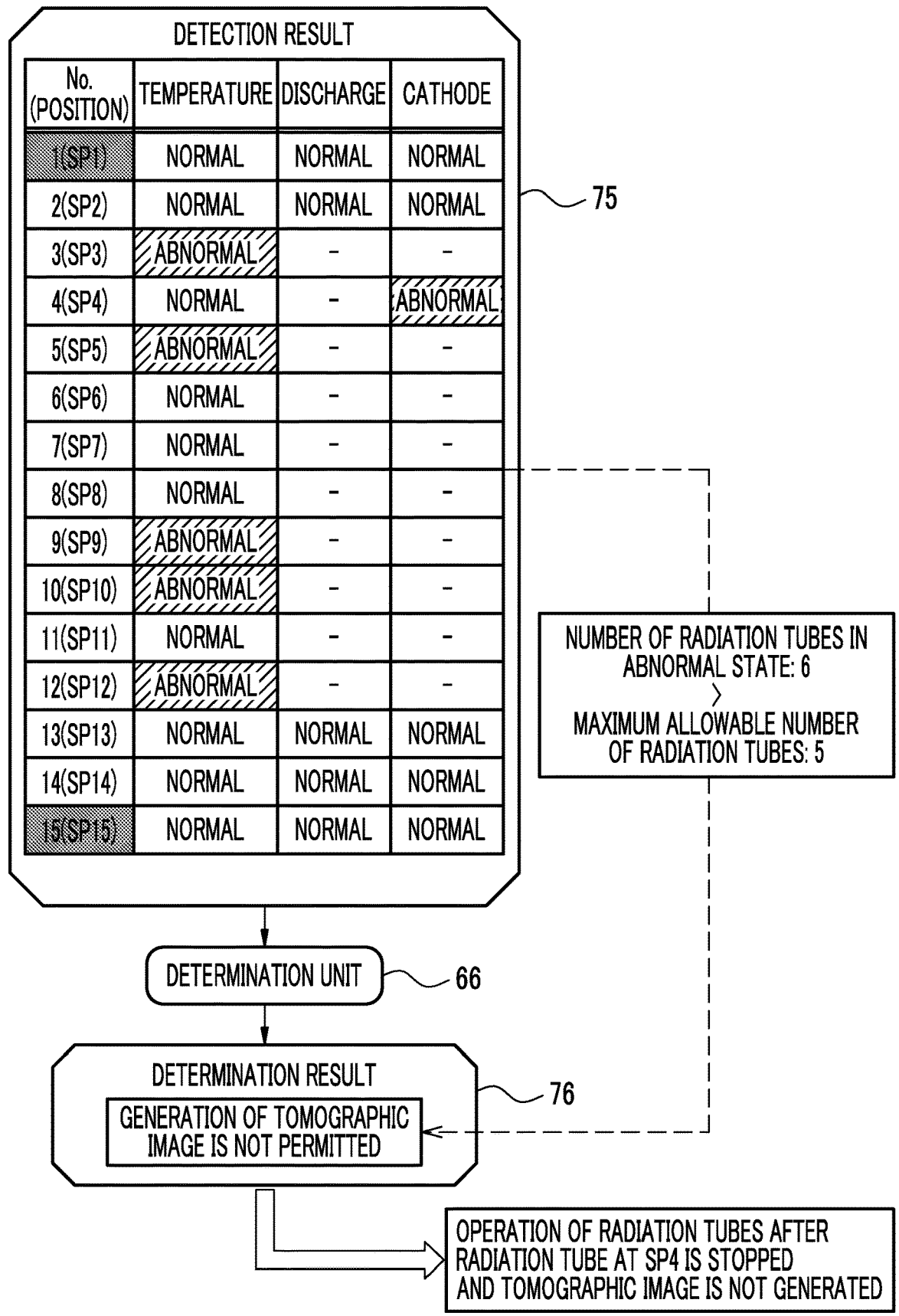
FIG. 23 is a diagram illustrating an example of a detection result and a determination result.

The detection result 75 illustrated in FIG. 23 shows a case in which a total of five radiation tubes 27, that is, the radiation tube 27 at the position SP3, the radiation tube 27 at the position SP5, the radiation tube 27 at the position SP9, the radiation tube 27 at the position SP10, and the radiation tube 27 at the position SP12 have been detected to be abnormal due to temperature. Further, the detection result 75 shows a case in which the radiation tube 27 at the position SP4 has been detected to be abnormal due to the failure of the cathode 35. That is, as in the example illustrated in FIG.

22, the number of radiation tubes 27 in the abnormal state except the irradiation essential radiation tube 27R is 6 and is greater than 5 which is the maximum allowable number of radiation tubes. Therefore, this corresponds to the second pattern. Therefore, in this case, the determination unit 66 outputs the determination result 76 indicating that the generation of the tomographic image T is not permitted, as in the cases of FIGS. 20 to 22.

As illustrated in FIG. 12, the cathode failure detection unit 72 detects that the radiation tube 27 is in the abnormal state due to the failure of the cathode 35 after each radiation tube 27 is operated in the tomosynthesis imaging. Therefore, in the example illustrated in FIG. 23, the determination unit 66 outputs the determination result 76 after the radiation tube 27 at the position SP4 is operated. Therefore, in the example illustrated in FIG. 23, the control unit 67 stops the operation of the radiation tubes 27 after the radiation tube 27 at the position SP4 and does not direct the generation unit 68 to generate the tomographic image T.

As described above, in some cases, the determination unit 66 outputs the determination result 76 before the tomosynthesis imaging is started or outputs the determination result 76 during the tomosynthesis imaging. In a case in which the determination result 76 is output before the tomosynthesis imaging is started and the determination result 76 indicates that the generation of the tomographic image T is not permitted, the control unit 67 stops the tomosynthesis imaging as illustrated in FIGS. 20 and 22. In contrast, in a case in which the determination result 76 is output during the tomosynthesis imaging and the determination result 76 indicates that generation of the tomographic image T is not permitted, the control unit 67 stops the operation of the radiation tubes 27 after the radiation tubes 27 operated when the determination result 76 is output such that the tomographic image T is not generated, as illustrated in FIGS. 21 and 23.

FIG. 24 illustrates a notification screen 85 displayed on the display by the display control unit 69 in response to a display operation command from the operator. A list 86 of the temperature (unit: ° C.) and the amount of heat/heat capacity (unit: %) of each radiation tube 27 is displayed on the notification screen 85. That is, the display control unit 69 is an example of a "third notification unit" according to the technology of the present disclosure.

The temperature detected by the temperature detection unit 70 is used as the temperature of each radiation tube 27 displayed in the list 86. The amount of heat/heat capacity is the ratio of the amount of heat applied to the heat capacity of each radiation tube 27. The heat capacity is determined in advance by the radiation tube 27 and is registered in advance. The amount of heat applied is the amount of heat converted by the temperature detection unit 70. The notification screen 85 is removed by the selection of a confirmation button 87.

Figure 25:
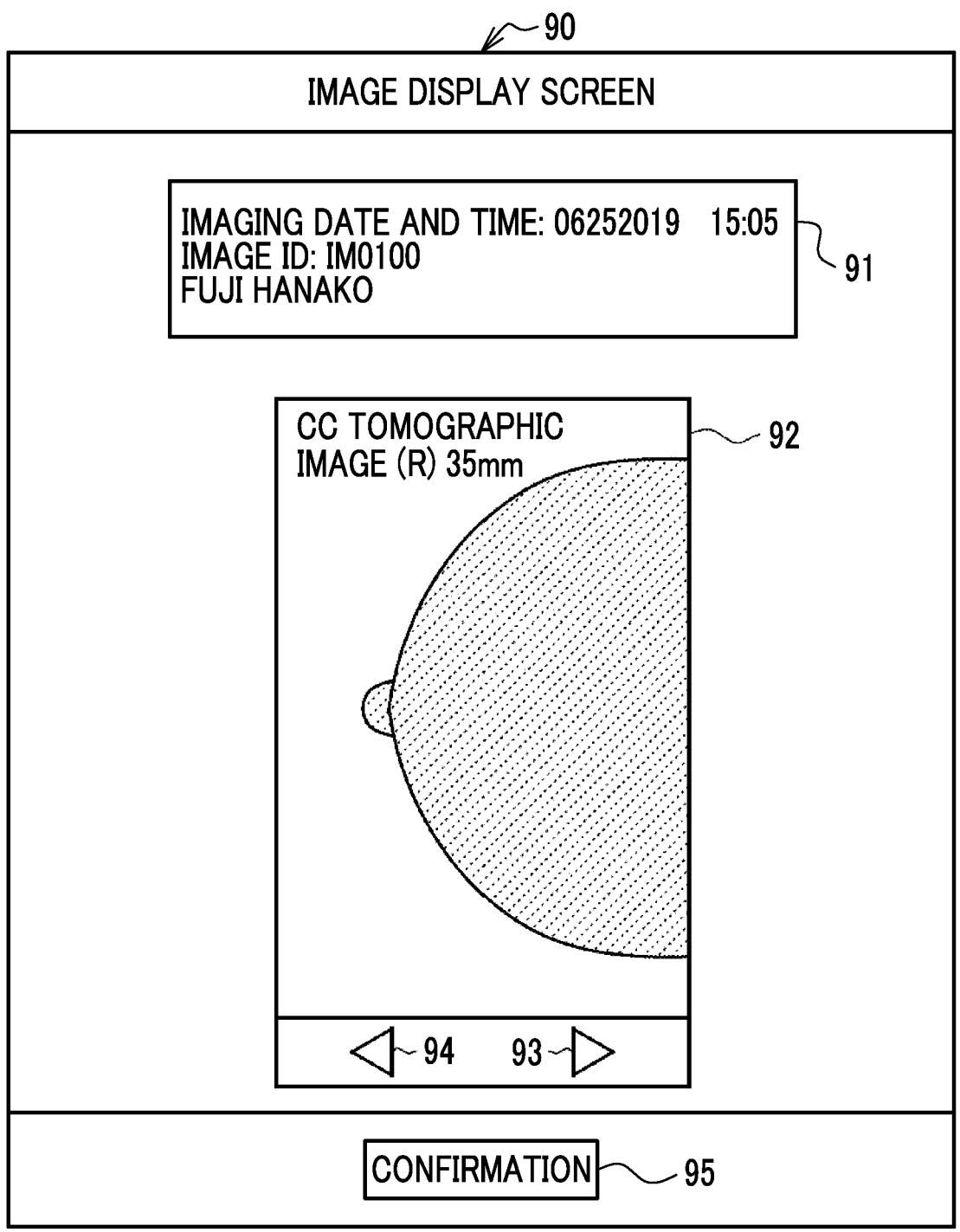
FIG. 25 is a diagram illustrating an image display screen.

As illustrated in FIG. 25, an image display screen 90 is displayed on the display 54 by the display control unit 69 in a case in which the generation unit 68 has generated the tomographic image T. The image display screen 90 includes an imaging information display region 91 and a tomographic image display region 92. Imaging information including an imaging date and time, image identification data (ID) for identifying the tomographic image T, and the name of the subject H is displayed in the imaging information display region 91. The tomographic image T is displayed in the tomographic image display region 92. FIG. 25 illustrates the tomographic image T obtained by the CC imaging. In the tomographic image T displayed in the tomographic image display region 92, a forward button 93 and a back button 94 provided in a lower part can be operated to switch the tomographic planes TF. The image display screen 90 is removed by the selection of a confirmation button 95.

Figure 26:
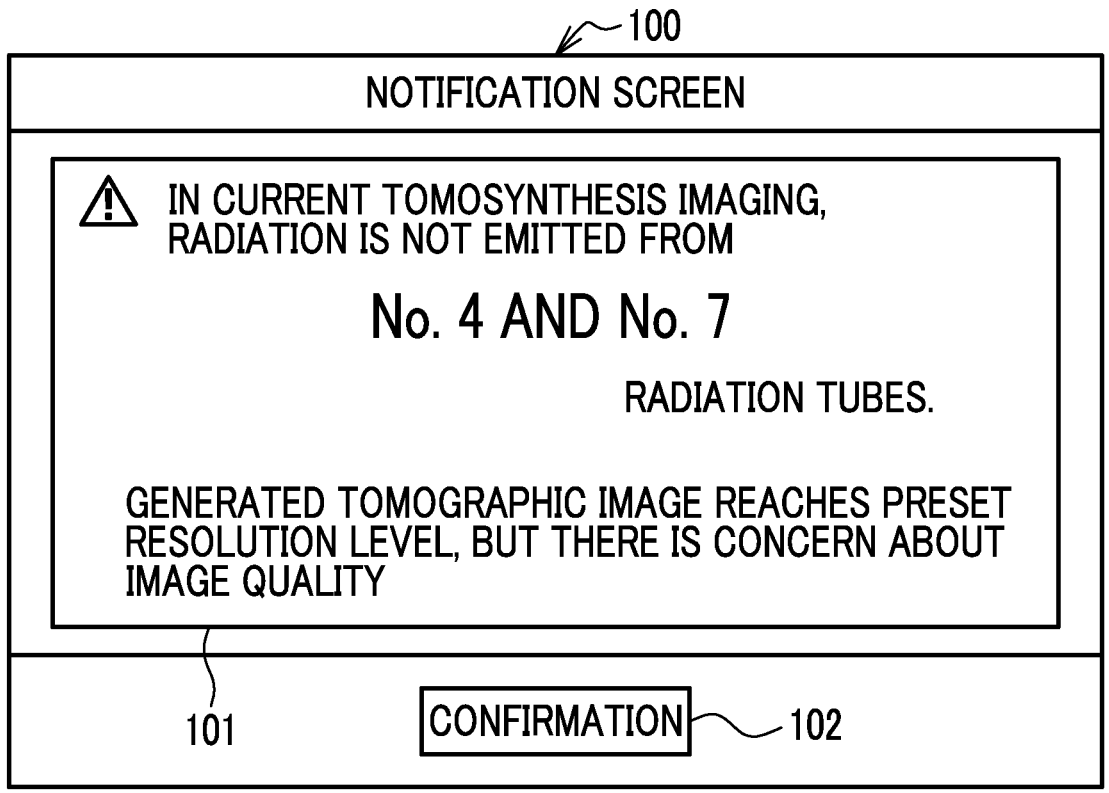
FIG. 26 is a diagram illustrating a notification screen for notifying that there is a radiation tube which has not emitted radiation.

FIG. 26 illustrates a notification screen 100 displayed on the display 54 by the display control unit 69 in a case in which the detection result 75 indicates that the radiation tube 27 in the abnormal state is present and the determination unit 66 determines to permit the generation of the tomographic image T. The notification screen 100 is displayed so as to pop up on the image display screen 90. A message 101 indicating that there is a radiation tube 27 which has not emitted the radiation 37 is displayed on the notification screen 100. That is, the display control unit 69 is an example of a "fourth notification unit" according to the technology of the present disclosure.

The message 101 includes data indicating that the resolution of the tomographic image T has reached a preset level but there is some concern about the quality of the image. The notification screen 100 is removed by the selection of a confirmation button 102. FIG. 26 illustrates a case in which the No. 4 radiation tube 27 at the position SP4 and the No. 7 radiation tube 27 at the position SP7 have not emit the radiation 37.

Figure 27:
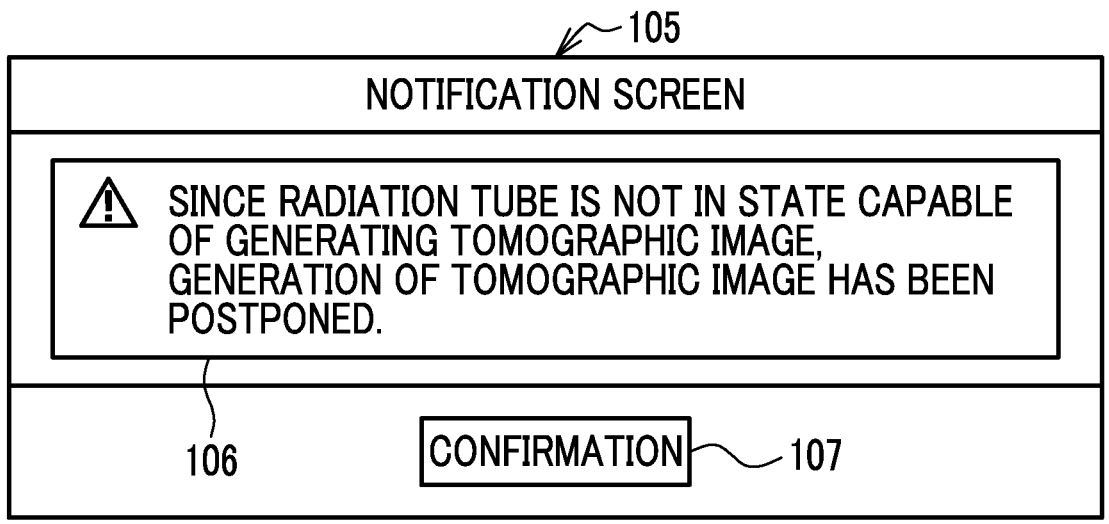
FIG. 27 is a diagram illustrating a notification screen for notifying that the generation of a tomographic image has been postponed.

FIG. 27 illustrates a notification screen 105 displayed on the display 54 by the display control unit 69 in a case in which the determination unit 66 determines not to generate the tomographic image T and the generation unit 68 does not generate the tomographic image T. The notification screen 105 is displayed instead of the image display screen 90. A message 106 indicating that the generation of the tomographic image T has been postponed since the radiation tube 27 is not in a state in which the tomographic image T can be generated is displayed on the notification screen 105. The notification screen 105 is removed by the selection of a confirmation button 107.

The display control unit 69 displays, on the display 54, a notification screen for notifying the radiation tube 27 detected to be abnormal and the cause thereof, in addition to the notification screen 105, which is not illustrated in the drawings. Further, in a case in which the cathode failure detection unit 72 has detected the failure of the cathode 35, the display control unit 69 displays, on the display 54, a notification screen for prompting the replacement of the radiation tube 27 in which the failure of the cathode 35 has been detected.

Next, the operation of the above-mentioned configuration will be described with reference to flowcharts illustrated in FIGS. 28 and 29. In a case in which the operation program 60 is started, the CPU 52 of the control device 12 functions as the detection unit 65 (the temperature detection unit 70, the discharge detection unit 71, and the cathode failure detection unit 72), the determination unit 66, the control unit 67, the generation unit 68, and the display control unit 69 as illustrated in FIG. 11.

Figure 28:
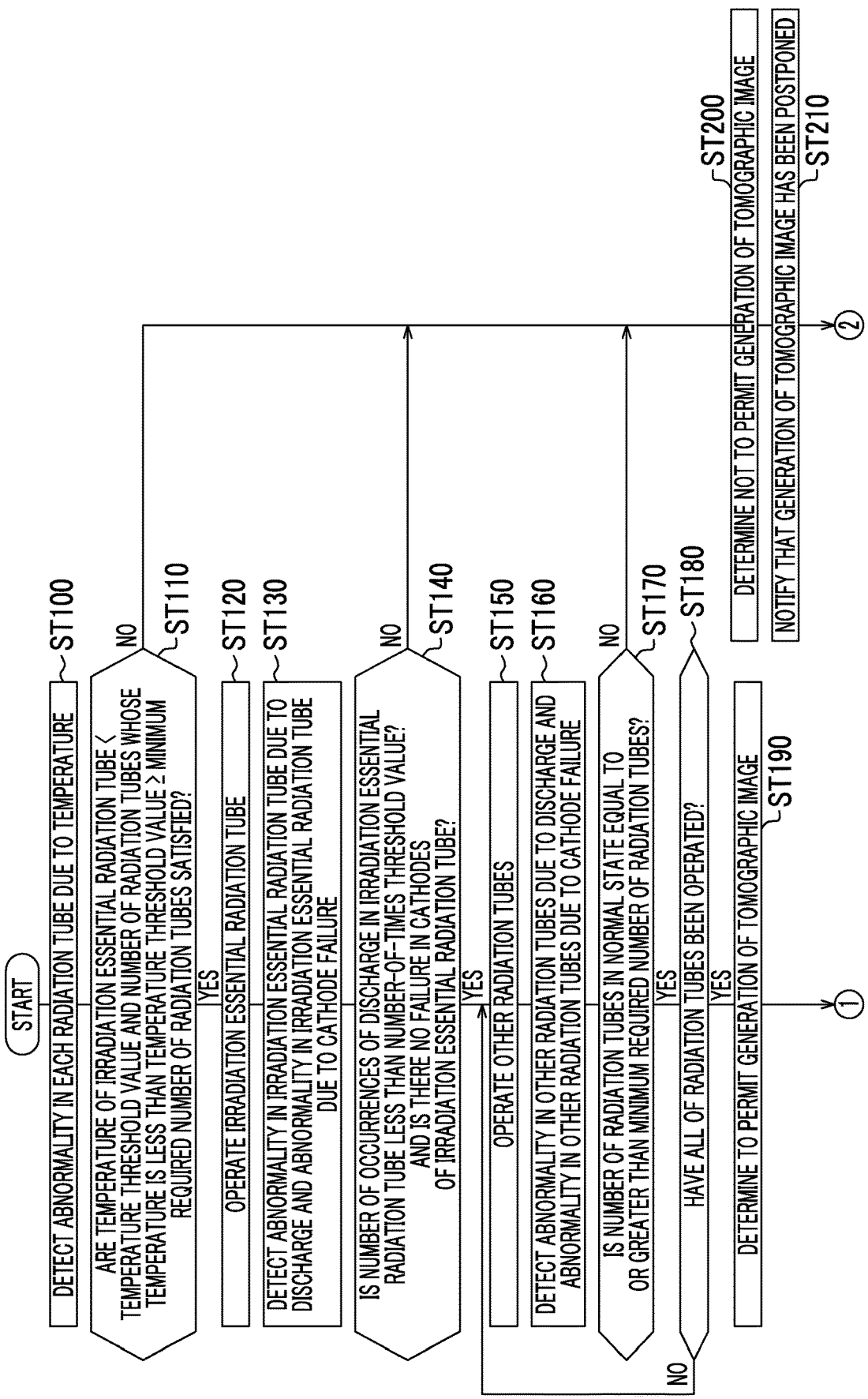
FIG. 28 is a flowchart illustrating a process procedure of the control device.

First, as illustrated in Step ST100 of FIG. 28, the temperature detection unit 70 detects an abnormality in each radiation tube 27 due to temperature. Then, in a case in which the temperature of the irradiation essential radiation tube 27R is lower than the temperature threshold value and the number of radiation tubes 27 including the irradiation essential radiation tube 27R and the radiation tubes other than the irradiation essential radiation tube 27R, whose temperature is less than the temperature threshold value, is equal to or greater than the minimum required number of radiation tubes (YES in Step ST110), the control unit 67 operates the irradiation essential radiation tube 27R first, as illustrated in FIG. 15 (Step ST120). Then, the discharge detection unit 71 detects whether or not the number of occurrences of discharge in the irradiation essential radiation tube 27R has reached the number-of-times threshold value. Further, the cathode failure detection unit 72 detects whether or not a failure has been recognized in the cathode 35 of the irradiation essential radiation tube 27R (Step ST130).

In a case in which the number of occurrences of discharge in the irradiation essential radiation tube 27R is less than the number-of-times threshold value and a failure has not been recognized in the cathode 35 of the irradiation essential radiation tube 27R (YES in Step ST140), the control unit 67 operates the radiation tubes 27 other than the irradiation essential radiation tube 27R in the order described in FIG. 15 (Step ST150). Thus, the discharge detection unit 71 detects whether or not the number of occurrences of discharge in the other radiation tubes 27 has reached the number-of-times threshold value. Further, the cathode failure detection unit 72 detects whether or not a failure has been recognized in the cathodes 35 of the other radiation tubes 27 (Step ST160). Step ST100, Step ST130, and Step ST160 are examples of a "detection step" according to the technology of the present disclosure.

In a case in which the number of radiation tubes 27 in the normal state is equal to or more than the minimum required number of radiation tubes on the basis of the detection result 75 in Step ST160 (YES in Step ST170) and all of the radiation tubes 27 are not operated by the control unit 67 (NO in Step ST180), the process in Steps ST150 and ST160 is repeated.

On the other hand, in a case in which the number of radiation tubes 27 in the normal state is equal to or greater than the minimum required number of radiation tubes on the basis of the detection result 75 in Step ST160 (YES in Step ST170) and all of the radiation tubes 27 are operated by the control unit 67 (YES in Step ST180), the determination unit 66 determines to permit the generation of the tomographic image T as illustrated in FIGS. 17 to 19 (Step ST190). Step ST190 is an example of a "determination step" according to the technology of the present disclosure.

In a case in which the temperature of the irradiation essential radiation tube 27R is equal to or greater than the temperature threshold value or in a case in which the number of radiation tubes 27 whose temperature is equal to or greater than the temperature threshold value except the irradiation essential radiation tube 27R is greater than the maximum allowable number of radiation tubes (NO in Step ST110), the determination unit 66 determines not to permit the generation of the tomographic image T as illustrated in FIGS. 20 and 22 (Step ST200).

In addition, in a case in which the number of occurrences of discharge in the irradiation essential radiation tube 27R is equal to or greater than the number-of-times threshold value or in a case in which a failure has been recognized in the cathode 35 of the irradiation essential radiation tube 27R (NO in Step ST140), the determination unit 66 determines not to permit the generation of the tomographic image T as illustrated in FIG. 21 (Step ST200).

Further, in a case in which the number of radiation tubes 27 in the abnormal state is greater than the maximum allowable number of radiation tubes on the basis of the detection result 75 in Step ST160 (NO in Step ST170), the determination unit 66 determines not to permit the generation of the tomographic image T as illustrated in FIG. 23 (Step ST200). Step ST200 is an example of the "determination step" according to the technology of the present disclosure.

In a case in which the determination unit 66 determines not to permit the generation of the tomographic image T, the display control unit 69 displays the notification screen 105 illustrated in FIG. 27 on the display 54 to notify the operator that the generation of the tomographic image T has been postponed (Step ST210).

Figure 29:
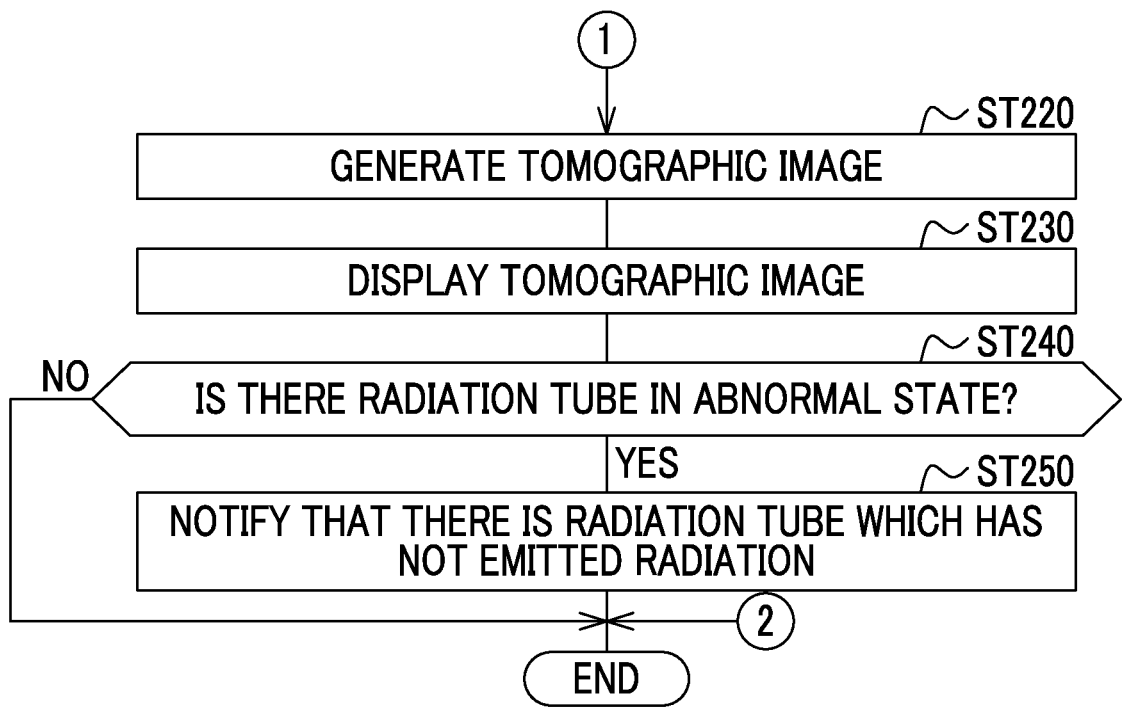
FIG. 29 is a flowchart illustrating a process procedure of the control device.

In a case in which the determination unit 66 determines to permit the generation of the tomographic image T, the generation unit 68 generates the tomographic image T as illustrated in FIG. 29 (Step ST220). Then, the display control unit 69 displays the image display screen 90 illustrated in FIG. 25 on the display 54 (Step ST230). In a case in which there is a radiation tube 27 in the abnormal state on the basis of the detection result 75 (YES in Step ST240), the display control unit 69 displays the notification screen 100 illustrated in FIG. 26 on the display 54 to notify the operator that there is a radiation tube 27 that has not emitted the radiation 37 (Step ST250).

As described above, the control device 12 comprises the detection unit 65 that detects the state of each of a plurality of radiation tubes 27 and the determination unit 66 that determines whether to permit the generation of the tomographic image T on the basis of the detection result 75 of the detection unit 65 and outputs the determination result 76. In a case in which there is no problem in the generation of the tomographic image T in the tomosynthesis imaging using the radiation tubes 27 other than the radiation tube 27 in the abnormal state, the determination unit 66 determines to permit the generation of the tomographic image T. Therefore, it is possible to utilize the advantages in a case in which the tomosynthesis imaging is performed using the radiation source 25 including a plurality of radiation tubes 27. It is possible to shorten the time for which the mammography apparatus 10 and to improve the efficiency of imaging.

On the other hand, in a case in which the detection result 75 of the irradiation essential radiation tube 27R indicates an abnormal state and the tomographic image T with a preset resolution level is not obtained, the determination unit 66 determines not to perform the generation of the tomographic image T. Further, in a case in which the number of radiation tubes 27 whose detection result 75 indicates an abnormal state is greater than the maximum allowable number of radiation tubes and the tomographic image T is expected to have unacceptable image quality deterioration, the determination unit 66 determines not to permit the generation of the tomographic image T. Therefore, it is possible to prevent the generation of the tomographic image T that does not reach a preset resolution level or has unacceptable image quality. It is possible to avoid the waste of time and effort to generate a meaningless tomographic image T. Further, in some cases, since the tomosynthesis imaging is stopped or suspended, it is possible to prevent unnecessary exposure to the subject H.

In addition, the control device 12 comprises the generation unit 68 that generates the tomographic image T and the control unit 67 that controls the operation of the generation unit 68 on the basis of the determination result 76 of the determination unit 66. Therefore, it is possible to cover the detection of the state of the radiation tube 27, the determination of whether to permit the generation of the tomographic image T on the basis of the detection result 75, the control of the generation of the tomographic image T on the basis of the determination result 76, and the generation of the tomographic image T with one device.

In a case in which there is a radiation tube 27 in the abnormal state, but the determination unit 66 determines to permit the generation of the tomographic image T, the generation unit 68 generates the tomographic image T on the basis of the projection images captured using at least two or more radiation tubes other than the radiation tube 27 detected to be abnormal by the detection unit 65. In addition, the generation unit 68 generates the tomographic image T without using the projection image captured using the radiation tube 27 detected to be abnormal by the detection unit 65. Further, in a case in which there is no radiation tube 27 detected to be abnormal by the detection unit 65, the generation unit 68 generates the tomographic image T on the basis of the projection images captured using all of at least three or more radiation tubes 27. As described above, it is possible to generate the tomographic image T adapted to various situations.

In a case in which the detection result 75 indicates that the irradiation essential radiation tube 27R is in the normal state and the number of radiation tubes 27 in the normal state including the irradiation essential radiation tube 27R and the radiation tubes other than the irradiation essential radiation tube 27R is equal to or greater than the minimum required number of radiation tubes, the determination unit 66 determines to permit the generation of the tomographic image T. In contrast, in a case in which the detection result 75 indicates that the irradiation essential radiation tube 27R is in the abnormal state or in a case in which the detection result 75 indicates that the number of radiation tubes 27 in the abnormal state except the irradiation essential radiation tube 27R is greater than the maximum allowable number of radiation tubes, the determination unit 66 determines not to perform the generation of the tomographic image T.

The irradiation essential radiation tube 27R is a radiation tube 27 that needs to emit the radiation 37 in order to generate the tomographic image T with a preset resolution level. In addition, the irradiation essential radiation tube 27R is the outermost radiation tube 27 in the minimum irradiation angle range required to generate the tomographic image T with a preset resolution level. Further, the irradiation essential radiation tubes 27R are the radiation tubes 27 disposed at both ends among a plurality of radiation tubes 27. As described above, since the criteria for determination are clearly defined and simple, the determination result 76 has no room for doubt.

The detection unit 65 determines that the radiation tube 27 is in the abnormal state in at least one of a case in which the temperature of the radiation tube 27 is equal to or greater than the temperature threshold value, a case in which the number of occurrences of discharge in the radiation tube 27 has reached the number-of-times threshold value, or a case in which a failure has been recognized in the cathode 35 of the radiation tube 27. Therefore, a state in which it is considered that the appropriate amount of radiation 37 satisfying the set irradiation conditions is not capable of being emitted can be detected as the abnormal state without omission.

The control unit 67 operates the irradiation essential radiation tube 27R first and directs the detection unit 65 to detect first whether or not the number of occurrences of discharge in the irradiation essential radiation tube 27R has reached the number-of-times threshold value and whether or not a failure has been recognized in the cathode 35 of the irradiation essential radiation tube 27R. In a case in which it is detected that the irradiation essential radiation tube 27R is in the abnormal state, the operation of the subsequent radiation tubes 27 is stopped. Therefore, it is possible to minimize unnecessary exposure to the subject H.

The display control unit 69 displays the notification screen 85 of the temperature and the amount of heat/heat capacity of the radiation tube 27 on the display 54. Therefore, the operator can see the temperature and the amount of heat/heat capacity of each radiation tube 27 at a glance. The operator can easily check the radiation tube 27 that is likely to be in the abnormal state due to the temperature equal to or greater than the temperature threshold value.

In addition, the display control unit 69 displays the notification screen 100 notifying that there is a radiation tube 27 which has not emitted the radiation 37 on the display 54. Therefore, the operator can know that the tomographic image T has been generated without the projection images based on some of the radiation tubes 27 and there is some concern about the quality of the tomographic image T.

The list 86 of both the temperature and the amount of heat/heat capacity of each radiation tube 27 on the notification screen 85 illustrated in FIG. 24. However, the invention is not limited thereto. At least one of the temperature or the amount of heat/heat capacity of each radiation tube 27 may be displayed.

Further, the temperature and the amount of heat/heat capacity of all of the radiation tubes 27 are displayed on the notification screen 85 illustrated in FIG. 24. However, the invention is not limited thereto. The temperature and the amount of heat/heat capacity may be selectively displayed. For example, the radiation tubes 27 that are the top five in the temperature and the amount of heat/heat capacity are displayed.

Figure 30:
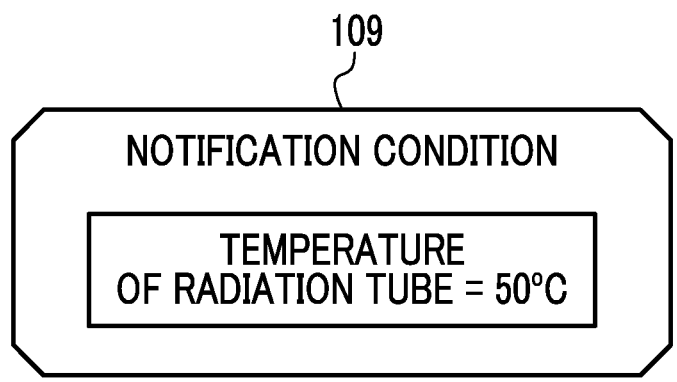
FIG. 30 is a diagram illustrating a notification condition.

Further, the notification screen 85 illustrated in FIG. 24 is displayed in response to a display operation command from the operator. However, the invention is not limited thereto. As illustrated in FIG. 30, a notification condition 109 may be set and the notification screen 85 may be displayed so as to pop up, regardless of the display operation command the operator in a case in which the notification condition 109 is satisfied. A temperature lower than at least the service temperature of the radiation tube 27 is set in the notification condition 109. In a case in which the service temperature is 60° C. as an example, the notification condition 109 is, for example, 50° C. (about 83% in terms of the amount of heat/heat capacity) as illustrated in FIG. 30. In this way, the operator can more reliably check the radiation tube 27 that is likely to be abnormal due to the temperature equal to or greater than the temperature threshold value.

In addition, for the radiation tube 27 detected to be abnormal due to the temperature equal to or greater than the temperature threshold value, in a case in which the temperature of the radiation tube 27 is reduced to be less than the temperature threshold value and the radiation tube 27 is detected to be normal and is immediately operated, the temperature of the radiation tube 27 increases to the temperature threshold value or more again and the radiation tube 27 is detected to be abnormal. Therefore, for the radiation tube 27 whose temperature is equal to or greater than the temperature threshold value once, it is preferable that the radiation tube 27 is detected to be normal in a case in which the temperature is several steps lower than the temperature threshold value, for example, in a case in which the radiation 37 is emitted ten times consecutively and the temperature reaches the service temperature of the radiation tube 27. In this case, it is possible to prevent the situation in which the temperature becomes equal to or greater than the temperature threshold value and the radiation tube is detected to be abnormal immediately after the radiation tube returns to the normal state.

Second Embodiment

Discharge occurs due to a decrease in the degree of vacuum in the radiation tube 27. For this reason, there is a case in which the degree of vacuum in the radiation tube 27 is restored by the occurrence of discharge and the radiation 37 is emitted without generating discharge in the next operation. Therefore, in a second embodiment illustrated in FIGS. 31 to 39, the radiation tube 27 in which discharge has occurred performs an irradiation retrying operation for emitting the radiation 37 again.

As illustrated in FIG. 31, the detection conditions 110 according to the second embodiment are different from the detection conditions 61 according to the first embodiment illustrated in FIG. 13 in the number-of-times threshold value for the number of occurrences of discharge. Specifically, while the number-of-times threshold value is set to 1 in the detection conditions 61, the number-of-times threshold value is set to 2 in the detection conditions 110. That is, the detection conditions 110 are an example in which the number-of-times threshold value is equal to or greater than 2.

Figure 32:
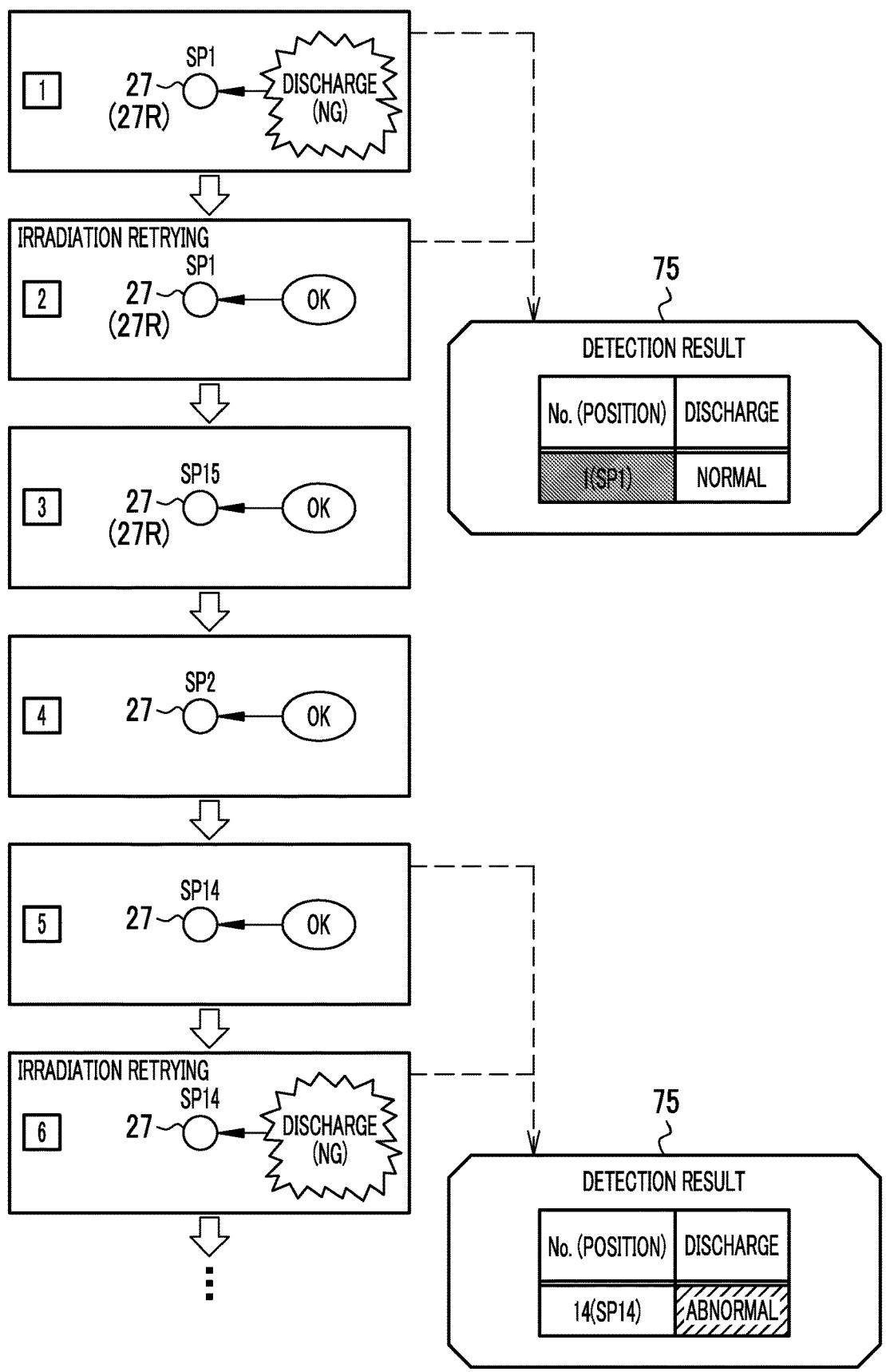
FIG. 32 is a diagram illustrating an aspect in which a radiation tube in which the number of occurrences of discharge is equal to or greater than 1 and is less than a number-of-times threshold value performs an irradiation retrying operation for emitting radiation again.

As illustrated in FIG. 32, the control unit 67 directs the radiation tube 27, in which the number of occurrences of discharge is equal to or greater than 1 and is less than the number-of-times threshold value, to perform the irradiation retrying operation for emitting the radiation 37 again. In this example, since the number-of-times threshold value is 2, the control unit 67 directs the radiation tube 27 in which discharge has occurred once to perform the irradiation retrying operation. That is, the control unit 67 is an example of a "third control unit" according to the technology of the present disclosure.

FIG. 32 illustrates an example in which discharge has occurred in the radiation tube 27 at the position SP1 and the radiation tube 27 at the position SP14. The control unit 67 directs the radiation tubes to perform the irradiation retrying operation immediately after discharge occurs. The radiation 37 is emitted from the radiation tube 27 at the position SP1 by the irradiation retrying operation and a projection image is obtained without any trouble. In this case, the discharge detection unit 71 detects that the radiation tube 27 at the position SP1 is in the normal state. In contrast, discharge still occurs in the radiation tube 27 at the position SP14 even in a case in which the irradiation retrying operation is performed. In this case, the discharge detection unit 71 detects that the radiation tube 27 at the position SP14 is in the abnormal state.

Figure 33:
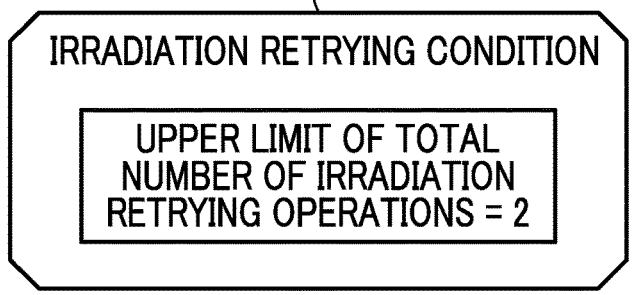
FIG. 33 is a diagram illustrating irradiation retrying conditions.

As illustrated in FIG. 33, in the second embodiment, an irradiation retrying condition 112 is stored in the storage device 50. The upper limit of the total number of irradiation retrying operations is registered in the irradiation retrying condition 112. In FIG. 33, 2 is registered as the upper limit of the total number of irradiation retrying operations.

Figure 34:
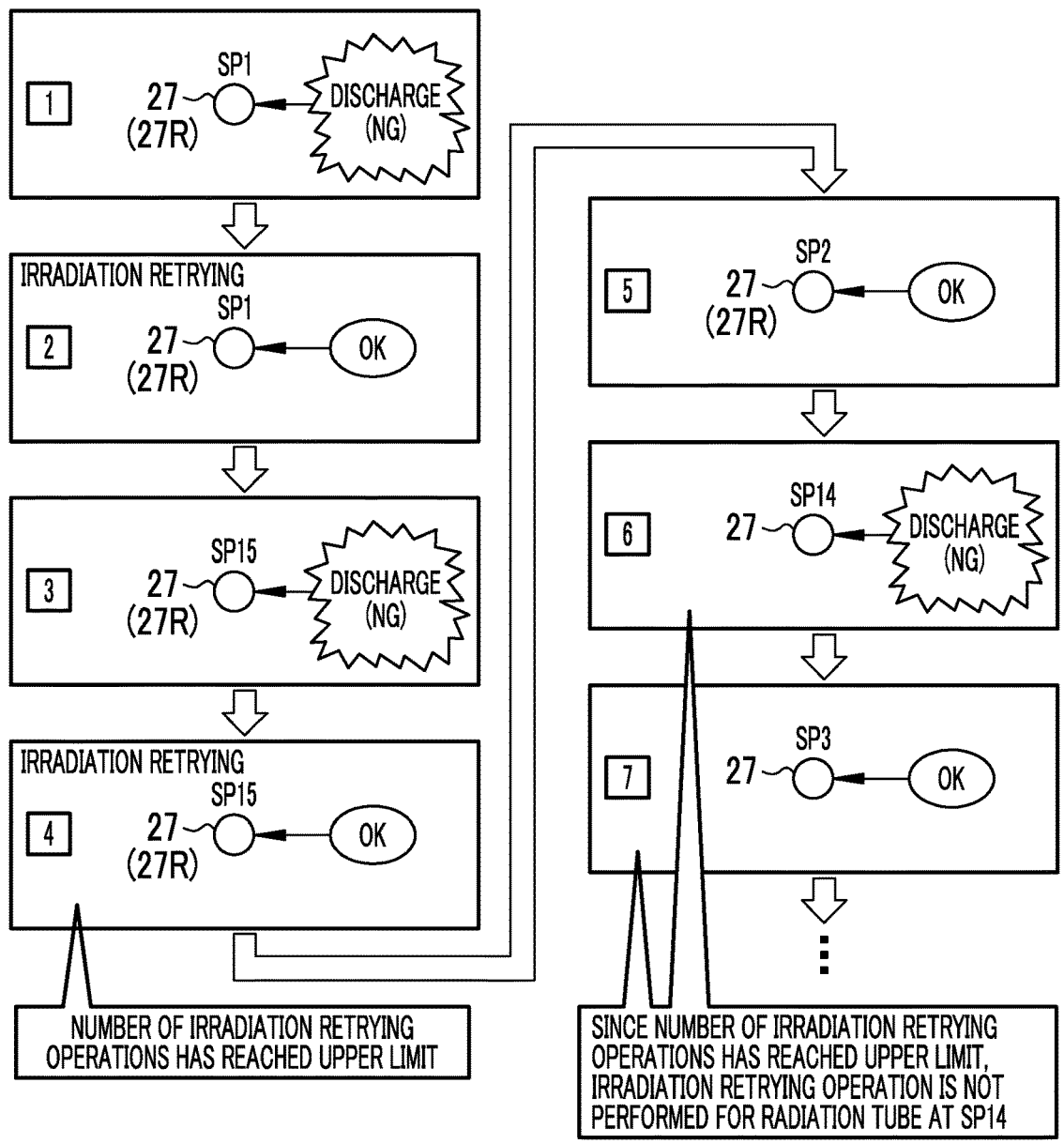
FIG. 34 is a diagram illustrating an aspect in which, in a case in which the total number of irradiation retrying operations has reached an upper limit, the subsequent irradiation retrying operations are not performed.

As illustrated in FIG. 34, in a case in which the total number of irradiation retrying operations reaches the upper limit registered in irradiation retrying condition 112, the control unit 67 does not perform the subsequent irradiation retrying operation. FIG. 34 illustrates an example in which discharge has occurred in the radiation tube 27 at the position SP1, the radiation tube 27 at the position SP15, and the radiation tube 27 at the position SP14. In this case, the control unit 67 directs the radiation tube 27 at the position SP1 and the radiation tube 27 at the position SP15 to perform the irradiation retrying operation. However, since the total number of irradiation retrying operations is 2 and reaches the upper limit due to the irradiation retrying operation of the radiation tube 27 the position SP15, the control unit 67 does not direct the radiation tube 27 at the position SP14 to perform the irradiation retrying operation.

Figure 35:
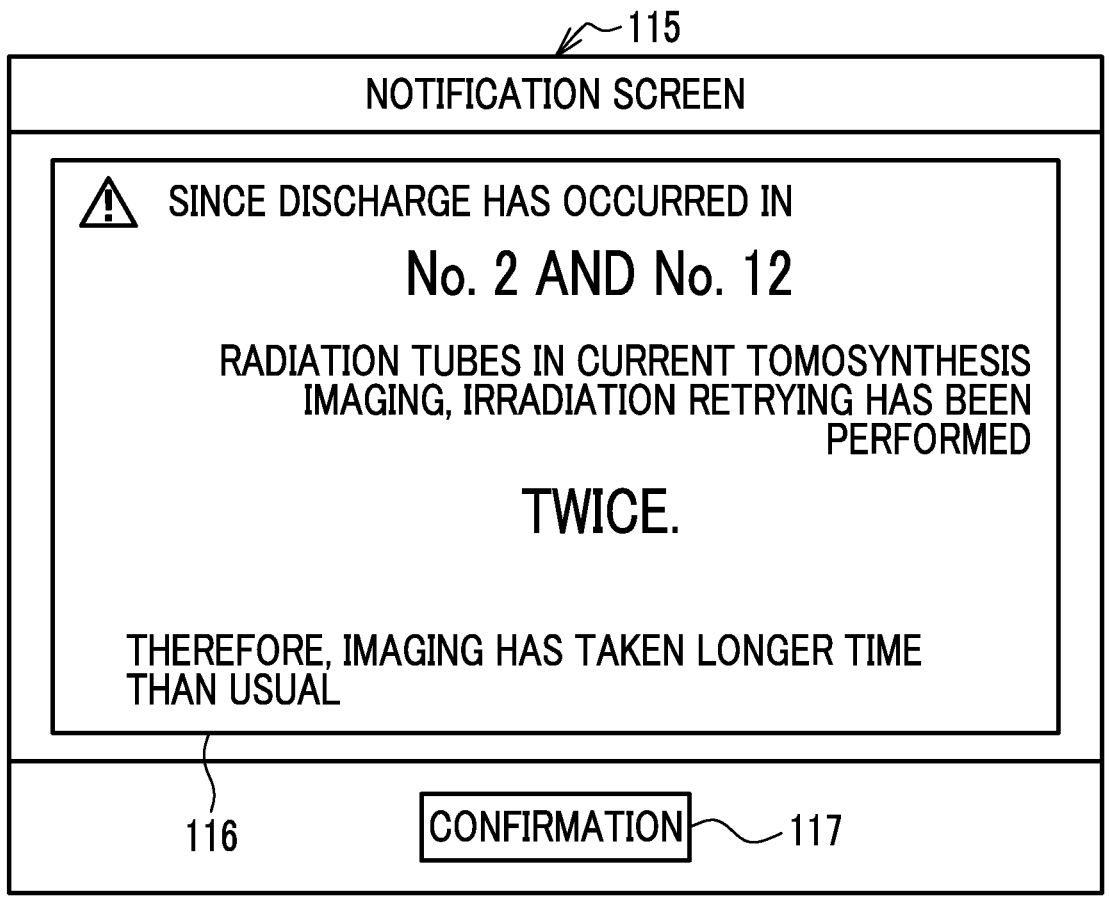
FIG. 35 is a diagram illustrating a notification screen for notifying that the irradiation retrying operation has been performed.

In a case in which the irradiation retrying operation is performed, the display control unit 69 displays a notification screen 115 illustrated in FIG. 35 on the display 54. A message 116 indicating that the irradiation retrying operation has been performed is displayed on the notification screen 115. That is, the display control unit 69 is an example of a "first notification unit" according to the technology of the present disclosure.

The message 116 includes the number of the radiation tube 27 in which discharge has occurred, the number of irradiation retrying operations, and information indicating that the tomosynthesis imaging has taken longer than usual. The notification screen 115 is removed by the selection of a confirmation button 117. FIG. 35 illustrates a case in which discharge has occurred in the No. 2 radiation tube 27 at the position SP2 and the No. 12 radiation tube 27 at the position SP12 and the irradiation retrying operation has performed twice.

As described above, in the second embodiment, the number-of-times threshold value is set to two or more and the control unit 67 directs the radiation tube 27, in which the number of occurrences of discharge is equal to or greater than 1 and is less than the number-of-times threshold value, to perform the irradiation retrying operation. Therefore, it is possible to reduce the number of radiation tubes 27 detected to be abnormal and to increase the probability that the determination unit 66 will determine to permit the generation of the tomographic image T, as compared to a case in which the number-of-times threshold value is set to 1. Therefore, it is possible to further utilize the advantage in a case in which the tomosynthesis imaging is performed using the radiation source 25 including a plurality of radiation tubes 27 and to further improve the efficiency of imaging.

The upper limit is set for the total number of irradiation retrying operations. Therefore, the irradiation retrying operation is not performed many times and the time required for the tomosynthesis imaging does not increase. In a case in which the time required for the tomosynthesis imaging is long, the breast M is moved by the body movement of the subject H and there is a concern that the quality of the projection image and the tomographic image T will deteriorate significantly. However, it is possible to remove the concern.

The display control unit 69 displays the notification screen 115 indicating that the irradiation retrying operation has been performed on the display 54. Therefore, the operator can easily know that discharge has occurred in the radiation tube 27 and the irradiation retrying operation has been performed.

Discharge may occur in a case in which the tube voltage rises before the emission of the radiation 37 or may occur after the emission of the radiation 37 is started. In the latter case, since the radiation 37 is additionally emitted, the amount of radiation is larger than that assumed under the irradiation conditions. In this case, in addition to the information indicating that the tomosynthesis imaging has taken longer than usual, information indicating that the amount of radiation 37 is more than usual may be notified through the notification screen 115.

Figure 36:
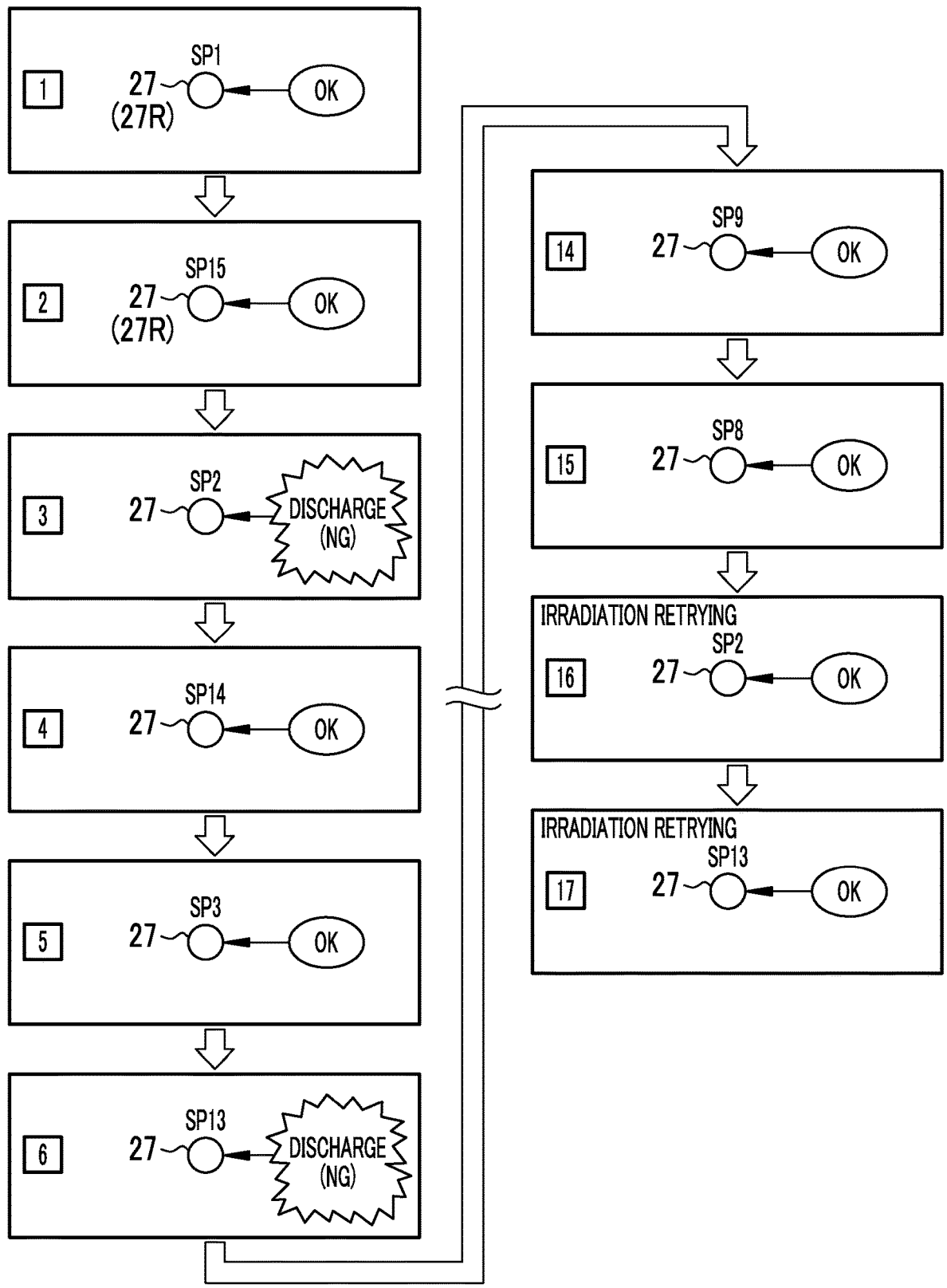
FIG. 36 is a diagram illustrating an aspect in which the irradiation retrying operations are collectively performed after all of the radiation tubes are operated once.
Figure 37:
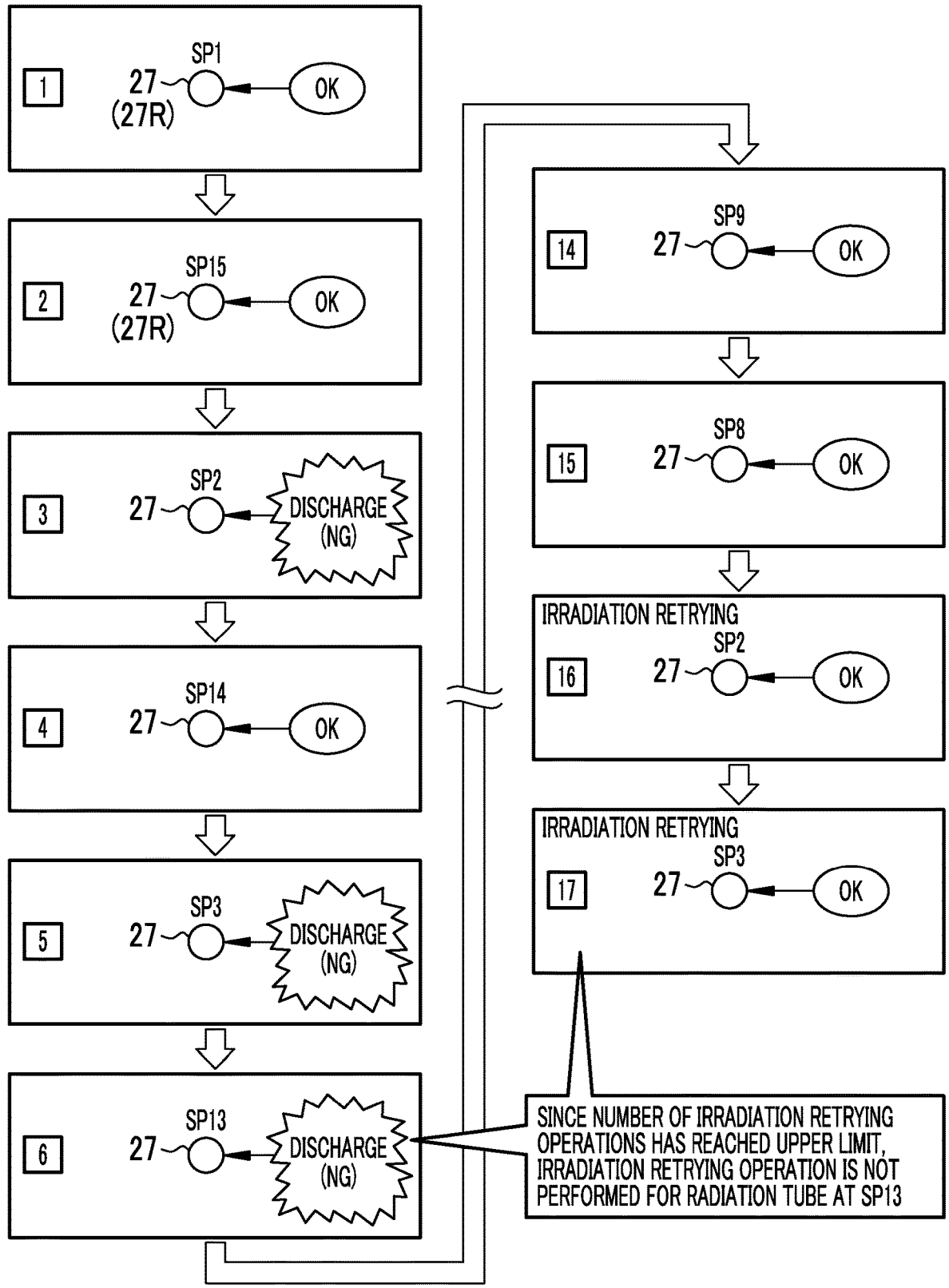
FIG. 37 is a diagram illustrating a case in which the total number of irradiation retrying operations has reached the upper limit in the aspect in which the irradiation retrying operations are collectively performed after all of the radiation tubes are operated once.

In the examples illustrated in FIGS. 32 and 34, the control unit 67 performs the irradiation retrying operation immediately after discharge occurs. However, the invention is not limited thereto. As illustrated in FIGS. 36 and 37, the irradiation retrying operation may be collectively performed after 15 radiation tubes 27 are operated once.

FIG. 36 illustrates a case in which discharge has occurred in the radiation tube 27 at the position SP2 and the radiation tube 27 at the position SP13 while 15 radiation tubes 27 are sequentially and alternately operated one by one on the left and right sides from both ends once as illustrated in FIG. 15. In this case, the control unit 67 directs the radiation tubes 27 at the position SP2 and the radiation tube 27 at the position SP13 to perform the irradiation retrying operation after operating the 15 radiation tubes 27 once.

FIG. 37 illustrates a case in which discharge has occurred in the radiation tube 27 at the position SP2, the radiation tube 27 at the position SP3, and the radiation tube 27 at the position SP13. In addition, FIG. 37 illustrates a case in which the upper limit of the total number of irradiation retrying operations is set to 2 as in the case of FIG. 33. In this case, after operating the 15 radiation tubes 27 once, the control unit 67 directs the radiation tube 27 at the position SP2 and the radiation tube 27 at the position SP3 to perform the irradiation retrying operation. However, since the total number of irradiation retrying operations is 2 and reaches the upper limit due to the irradiation retrying operation of the radiation tube 27 at the position SP3, the control unit 67 does not direct the radiation tube 27 at the position SP13 to perform the irradiation retrying operation.

As described above, the irradiation retrying operation is performed immediately after discharge occurs and after all of the radiation tubes 27 are operated once. Immediately after discharge occurs, the irradiation retrying operation can be performed in several tens of milliseconds and the discharge detection unit 71 can immediately detect the state. However, the operation control of the radiation tubes 27 is more complicated than that in a case in which the irradiation retrying operation is performed after all of the radiation tubes 27 are operated once. On the other hand, in a case in which all of the radiation tubes 27 are operated once, the operation control of the radiation tubes 27 is simple, but the determination result 76 is not known until the irradiation retrying operation ends. Therefore, in a case in which the determination result 76 indicates that the generation of the tomographic image T is not permitted, the subject H is forced to be unnecessarily exposed to radiation.

The irradiation essential radiation tube 27R may perform the irradiation retrying operation immediately after discharge occurs and the other radiation tubes 27 may perform the irradiation retrying operation after all of the radiation tubes 27 are operated once.

As illustrated in FIG. 37, in a case in which the number of radiation tubes 27 in which discharge has occurred exceeds the upper limit of the total number of irradiation retrying operations, some radiation tubes 27 perform the irradiation retrying operation and some radiation tubes 27 do not perform the irradiation retrying operation. Therefore, among the radiation tubes 27 in which discharge has occurred, the radiation tube 27 having a high probability of emitting the radiation 37 without generating discharge in a case in which the irradiation retrying operation is performed may be selected as the radiation tube 27 that performs the irradiation retrying operation.

Specifically, as illustrated in FIG. 38, irradiation retrying operation success and failure information 120 is stored in the storage device 50. The success rate of the irradiation retrying operation of each radiation tube 27 is registered in the irradiation retrying operation success and failure information 120. The success rate of the irradiation retrying operation is the ratio of the number of successes of the irradiation retrying operation to the total number of irradiation retrying operations. The control unit 67 selects a radiation tube 27 that performs the irradiation retrying operation from the radiation tubes 27 in which discharge has occurred on the basis of the irradiation retrying operation success and failure information 120.

For example, a case is considered in which discharge has occurred in the No. 4 radiation tube 27 at the position SP4, the No. 11 radiation tube 27 at the position SP11, and the No. 13 radiation tube 27 at the position SP13 as illustrated in FIG. 39. According to the irradiation retrying operation success and failure information 120 illustrated in FIG. 38, the success rate of the No. 4 radiation tube 27 at the position SP4 is 100%, the success rate of the No. 11 radiation tube 27 at the position SP11 is 60%, and the success rate of the No. 13 radiation tube 27 at the position SP13 is 50%. Therefore, in this case, the control unit 67 selects the No. 4 radiation tube 27 at the position SP4 and the No. 11 radiation tube 27 at the position SP11 as the radiation tubes 27 that perform the irradiation retrying operation. As described above, in a case in which the radiation tube 27 that performs the irradiation retrying operation is selected on the basis of the irradiation retrying operation success and failure information 120, it is possible to increase the probability that the radiation 37 will be emitted without generating discharge in the irradiation retrying operations whose number is limited to the upper limit.

The irradiation essential radiation tube 27R may be treated as a seed, regardless of the success rate, and may certainly perform the irradiation retrying operation in a case in which discharge occurs. In this case, it is not necessary to register the success rate of the irradiation essential radiation tube 27R in the irradiation retrying operation success and failure information 120.

Third Embodiment

It is necessary to perform maintenance, such as replacement, for the radiation tube 27 in which discharge frequently occurs. Therefore, in a third embodiment illustrated in FIGS. 40 to 42, information for prompting the maintenance of the radiation tube 27 in which the frequency of discharge is equal to or greater than a preset frequency threshold value is notified. Here, the frequency of discharge is not the frequency of discharge in the irradiation retrying operation, but is the frequency of discharge in a case in which the radiation tube 27 is operated first.

As illustrated in FIG. 40, in the third embodiment, discharge occurrence history information 125 is stored in the storage device 50. Whether or not discharge has occurred in one to nine previous tomosynthesis imaging operations including the current tomosynthesis imaging operation, that is, the last 10 tomosynthesis imaging operations is registered for each radiation tube 27 in the discharge occurrence history information 125. The discharge occurrence history information 125 is updated whenever the tomosynthesis imaging operation is performed. Specifically, whether or not discharge has occurred in the current tomosynthesis imaging operation is rewritten as whether or not discharge has occurred in the previous tomosynthesis imaging operation and whether or not discharge has occurred in the previous tomosynthesis imaging operation is rewritten as whether or not discharge has occurred in the tomosynthesis imaging operation before the previous tomosynthesis imaging operations. FIG. 40 illustrates a case in which discharge has occurred five times in the No. 1 radiation tube 27 at the position SP1 among the last 10 imaging operations, has occurred once in the No. 2 radiation tube 27 at the position SP2, . . . , has occurred four times in the No. 15 radiation tube 27 at the position SP15.

Figure 41:
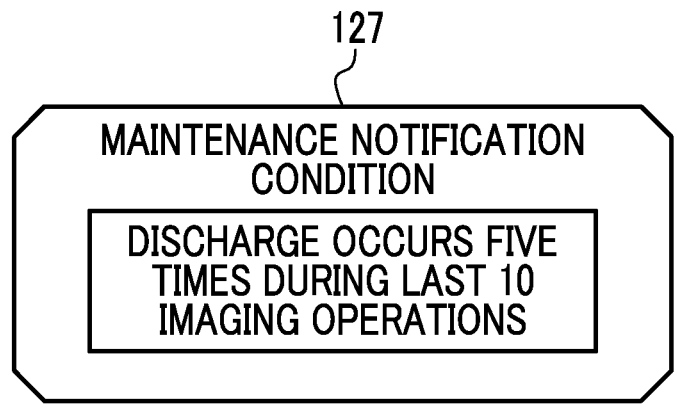
FIG. 41 is a diagram illustrating a maintenance notification condition.

In addition, as illustrated in FIG. 41, in the third embodiment, a maintenance notification condition 127 is stored in the storage device 50. The number of occurrences of discharge in the last 10 imaging operations is registered as the frequency threshold value for the frequency of discharge in the maintenance notification condition 127.

FIG. 41 illustrates an example in which 5 is registered as the number of occurrences of discharge in the last 10 imaging operations. In this example, among the radiation tubes 27 illustrated in FIG. 40, the radiation tube 27 in which discharge has occurred five times in the last 10 imaging has reached 5 times is the No. 1 radiation tube 27 at the position SP1. Therefore, the maintenance of the No. 1 radiation tube 27 at the position SP1 is notified.

Figure 42:
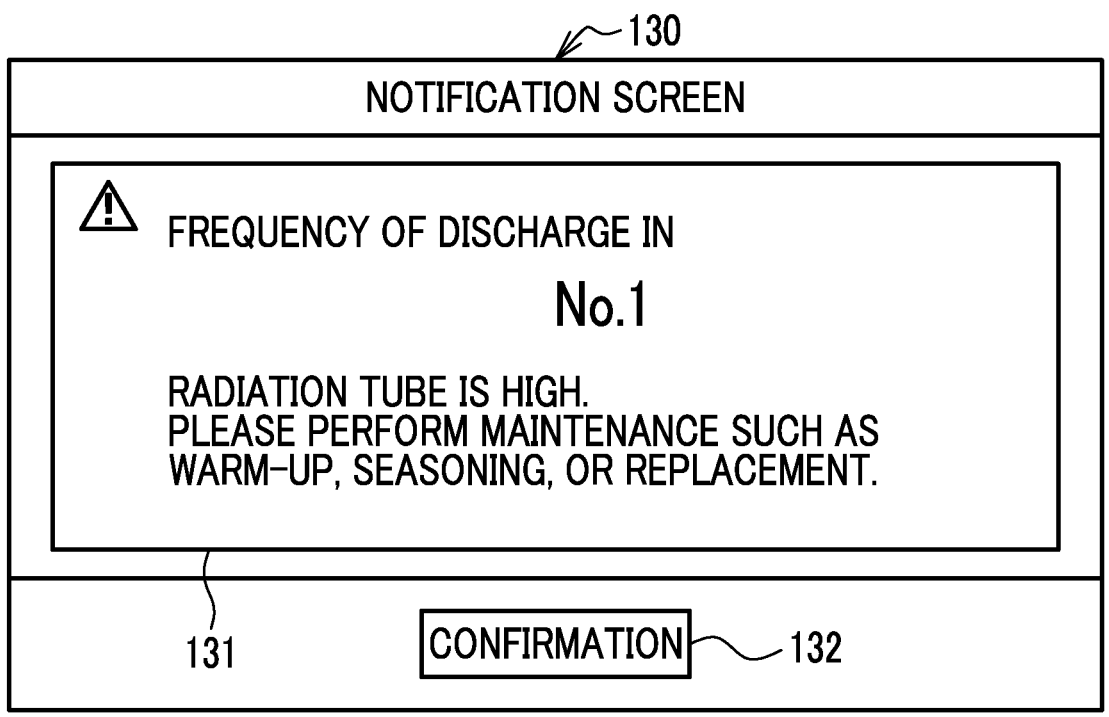
FIG. 42 is a diagram illustrating a notification screen for notifying information prompting the maintenance of a radiation tube in which the frequency of discharge has reached a preset frequency threshold value.

As illustrated in FIG. 42, the display control unit 69 displays, on the display 54, a notification screen 130 for prompting the maintenance of the radiation tube 27 in which the frequency of discharge has reached the frequency threshold value. A message 131 indicating that the frequency of discharge of the radiation tube 27 satisfying the maintenance notification condition 127 is high and prompting the operator to perform maintenance, such as warm-up, seasoning, or replacement, for the radiation tube 27 is displayed on the notification screen 130. That is, the display control unit 69 is an example of a "second notification unit" according to the technology of the present disclosure. The notification screen 130 is removed by the selection of a confirmation button 132. FIG. 42 illustrates an example which prompts the maintenance of the No. 1 radiation tube 27 at the position SP1.

As described above, in the third embodiment, information prompting the maintenance of the radiation tube 27 in which the frequency of discharge has reached the preset frequency threshold value is notified. Therefore, the operator can perform appropriate maintenance for the radiation tube 27 in which discharge frequently occurs.

In addition, information prompting maintenance, such as replacement, for the radiation tube 27 in which temperature frequently becomes equal to or greater than the temperature threshold value may be notified.

Fourth Embodiment

In a fourth embodiment illustrated in FIG. 43, a radiation tube 27 disposed at a position that is symmetric to the radiation tube 27 in the abnormal state in the detection result 75 is not operated.

FIG. 43 illustrates a case in which the radiation tube 27 at the position SP3 and the radiation tube 27 at the position SP10 are detected to be abnormal due to temperature. In this case, the control unit 67 does not operate the radiation tube 27 at the position SP13 that is symmetric to the radiation tube 27 at the position SP3 with respect to a line. Further, the control unit 67 does not operate the radiation tube 27 at the position SP6 that is symmetric to the radiation tube 27 at the position SP10 with respect to a line. That is, the control unit 67 is an example of a "fourth control unit" according to the technology of the present disclosure.

As described above, in the fourth embodiment, the radiation tube 27 disposed at a position that is symmetric to the radiation tube 27 in the abnormal state in the detection result 75 with respect to a line is not operated. Therefore, the obtained projection images are also symmetric with respect to a line. Therefore, the process related to the generation of the tomographic image T based on the projected images can be simpler than that in a case in which the projection images are not symmetric with respect to a line.

In addition, this is not applied to a case in which the radiation tube 27 disposed at a position that is symmetric to the radiation tube 27 in the abnormal state in the detection result 75 with respect to a line is not operated and the number of radiation tubes 27 that are not operated is greater than the maximum allowable number of radiation tubes. The control unit 67 operates the radiation tube 27 disposed at a position that is symmetric to the radiation tube 27 in the abnormal state in the detection result 75 with respect to a line.

Fifth Embodiment

In a case in which the temperature of the irradiation essential radiation tube 27R frequently becomes equal to or greater than the temperature threshold value and the frequency of the temperature detection unit 70 detecting the abnormal state increases, the frequency of the determination unit 66 determining not to permit the generation of the tomographic image T increases. Then, the tomosynthesis imaging is not performed and usability is reduced. Therefore, in the fifth embodiment illustrated in FIGS. 44 and 45, the heat dissipation performance of the irradiation essential radiation tube 27R is higher than that of the other radiation tubes 27 and/or the heat capacity of the irradiation essential radiation tube 27R is higher than that of the other radiation tubes 27.

Figure 44:
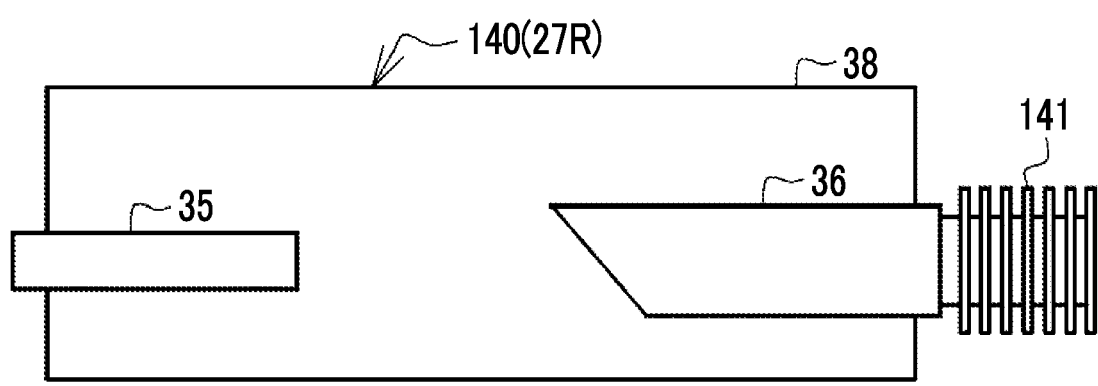
FIG. 44 is a diagram illustrating a radiation tube with improved heat dissipation performance.

In a radiation tube 140 illustrated in FIG. 44, cooling fins 141 are provided at the rear end of the anode 36. The radiation tube 140 is used as the irradiation essential radiation tube 27R and the radiation tubes 27 without the cooling fins 141 are used as the other radiation tubes 27. In this way, the heat dissipation performance of the irradiation essential radiation tube 27R can be higher than that of the other radiation tubes 27.

Figure 45:
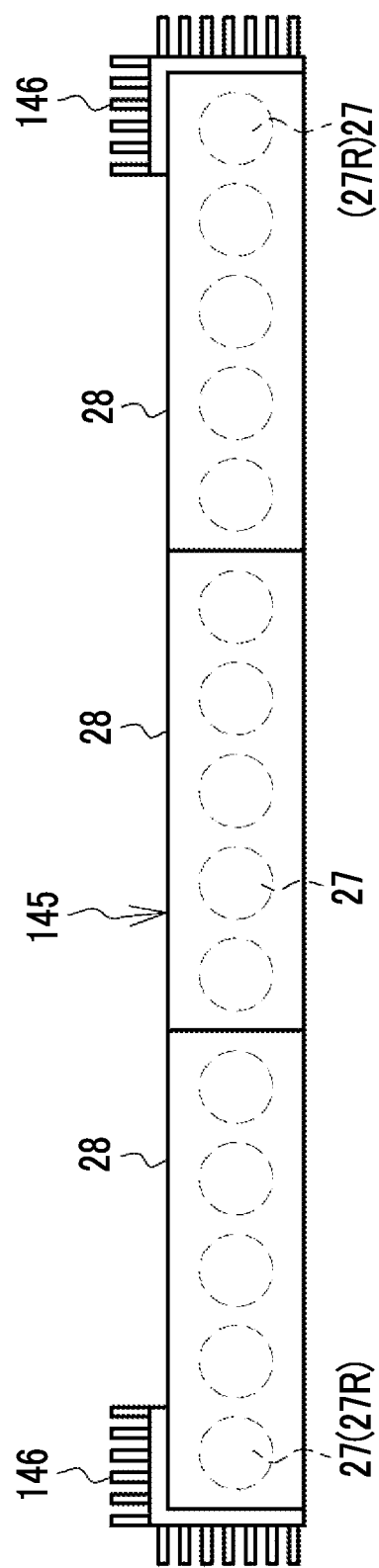
FIG. 45 is a diagram illustrating a radiation source in which the heat dissipation performance of an irradiation essential radiation tube has been improved.

In a radiation source 145 illustrated in FIG. 45, cooling fins 146 are provided around the irradiation essential radiation tube 27R in the housing 28. In this way, the heat dissipation performance of the irradiation essential radiation tube 27R can be higher than that of the other radiation tubes 27.

As a method of increasing the heat capacity of the irradiation essential radiation tube 27R to be higher than that of the other radiation tubes 27, a method is considered which simply increases the heat capacity of a component of the irradiation essential radiation tube 27R, for example, the glass tube 38.

As such, in the fifth embodiment, the heat dissipation performance of the irradiation essential radiation tube 27R is higher than that of the other radiation tubes 27 and/or the heat capacity of the irradiation essential radiation tube 27R is higher than that of the other radiation tubes 27. Therefore, the chance that the temperature of the irradiation essential radiation tube 27R will be equal to or greater than the temperature threshold value decreases and the frequency of the determination unit 66 determining not to perform the generation of the tomographic image T also decreases. Therefore, it is possible to further utilize the advantage in a case in which the tomosynthesis imaging is performed using the radiation source 25 including a plurality of radiation tubes 27 and to further improve the efficiency of imaging.

Figure 46:
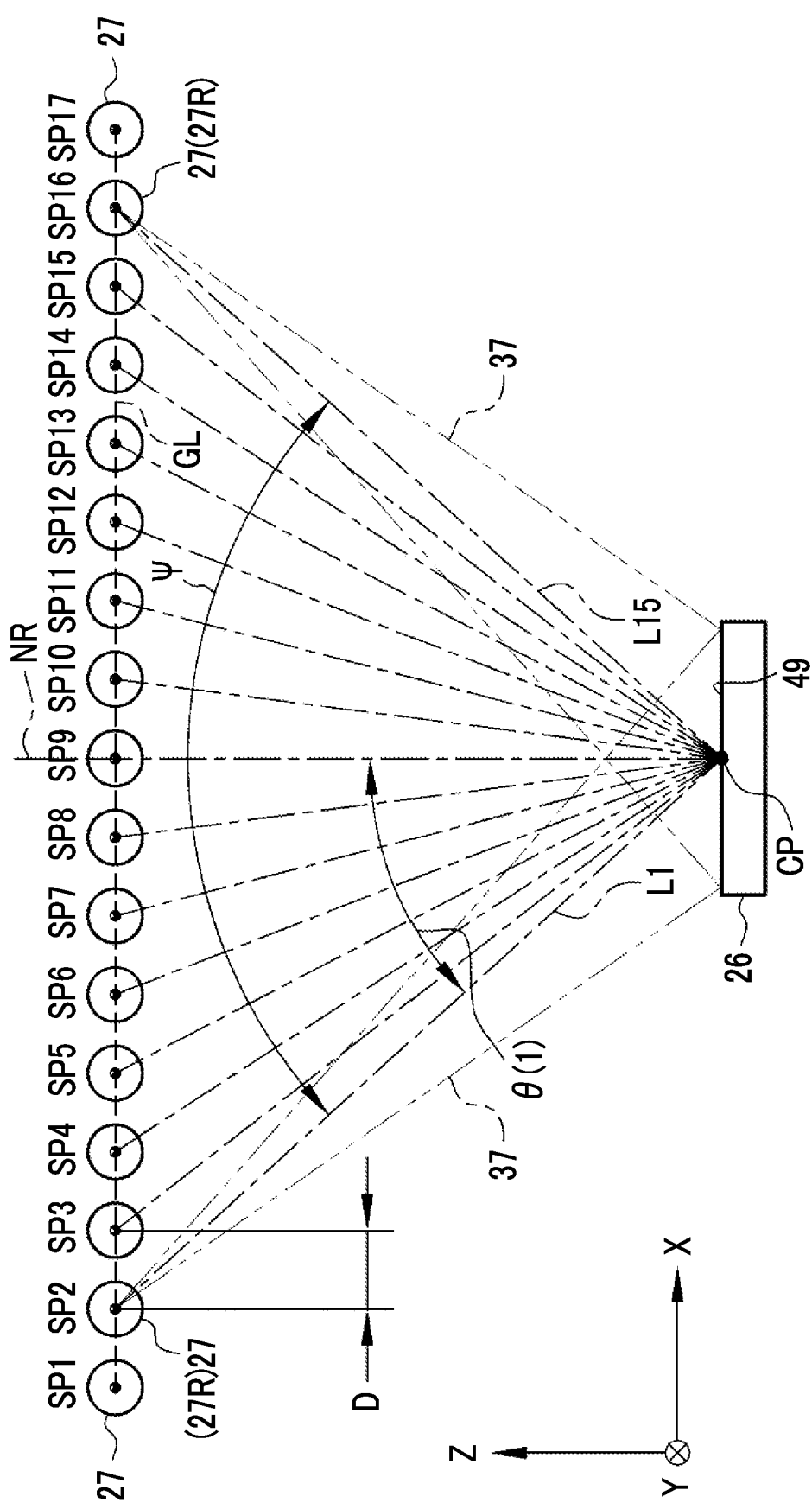
FIG. 46 is a diagram illustrating an example in which spare radiation tubes are disposed outside a maximum scanning angle.

In each of the above-described embodiments, the radiation tubes 27 disposed at both ends among a plurality of radiation tubes 27 are used as the irradiation essential radiation tubes 27R. However, the invention is not limited thereto. For example, a case is considered in which spare radiation tubes 27 (the radiation tube 27 at the position SP1 and the radiation tube 27 at the position SP17) are disposed outside the maximum scanning angle Ψ which is the range of the minimum irradiation angle required to generate the tomographic image T with a preset resolution level as illustrated in FIG. 46. In this case, the radiation tube 27 at the position SP2 and the radiation tube 27 at the position SP16 which are the outermost radiation tubes 27 within the maximum scanning angle Ψ are used as the irradiation essential radiation tubes 27R.

Figure 47:
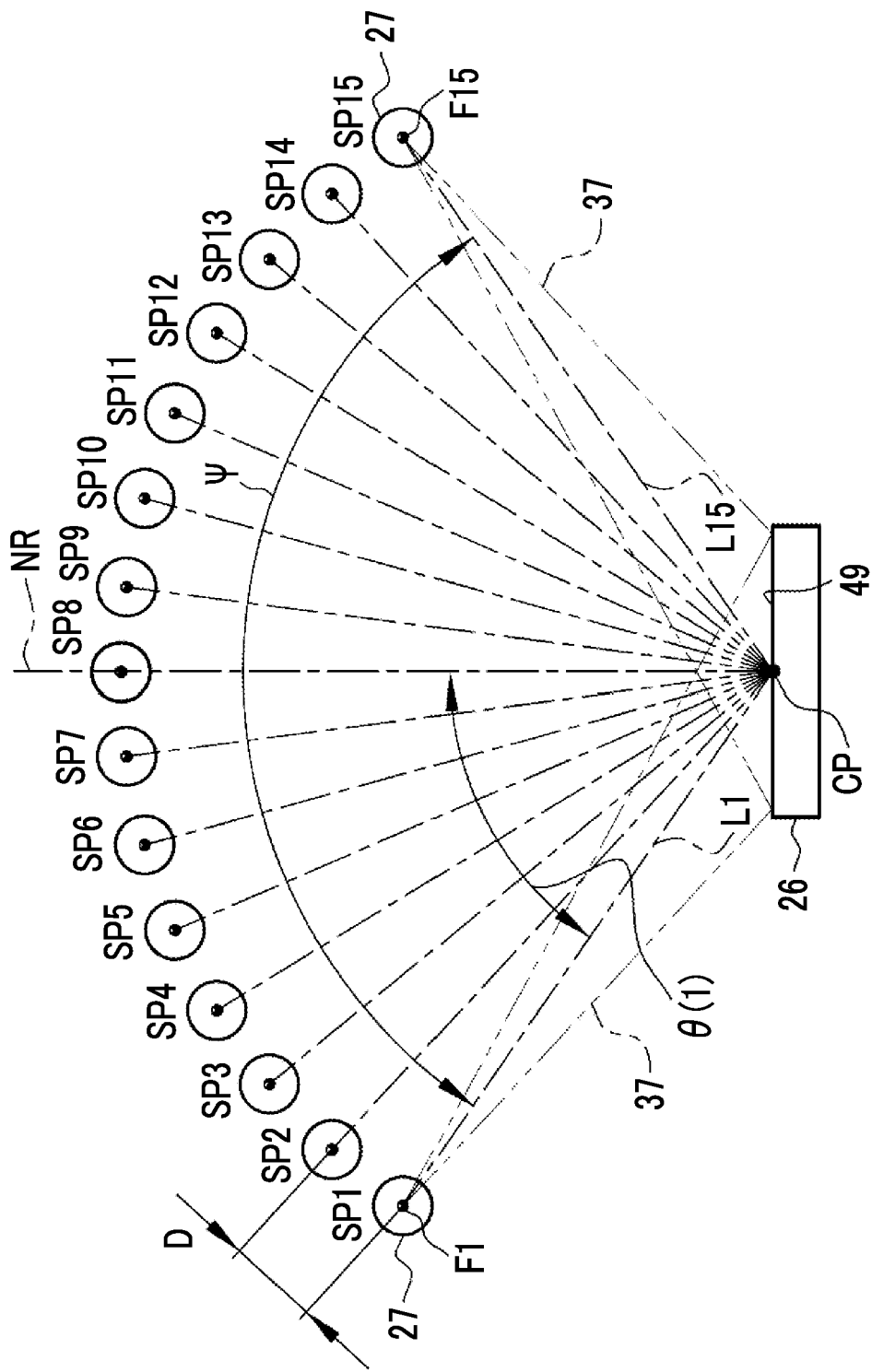
FIG. 47 is a diagram illustrating an example in which radiation tubes are disposed at a plurality of positions where the focuses of radiation are set so as to be arranged in an arc shape at equal intervals.

In each of the above-described embodiments, the positions where the focuses F are disposed are arranged in a straight line. However, the invention is not limited thereto. As illustrated in FIG. 47, the plurality of positions SP1 to SP15 where the focuses F1 to F15 are disposed may be arranged in an arc shape at equal intervals D.

Instead of the simple imaging in which the CC imaging illustrated in FIG. 6 and the MLO imaging illustrated in FIG. 7 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images obtained by the tomosynthesis imaging and a plurality of tomographic images T generated by the generation unit 68.

In each of the above-described embodiments, the control device 12 comprising the detection unit 65, the determination unit 66, the control unit 67, the generation unit 68, and the display control unit 69 has been described as an example. However, the invention is not limited thereto. A control device 150 illustrated in FIG. 48 may be used.

Figure 48:
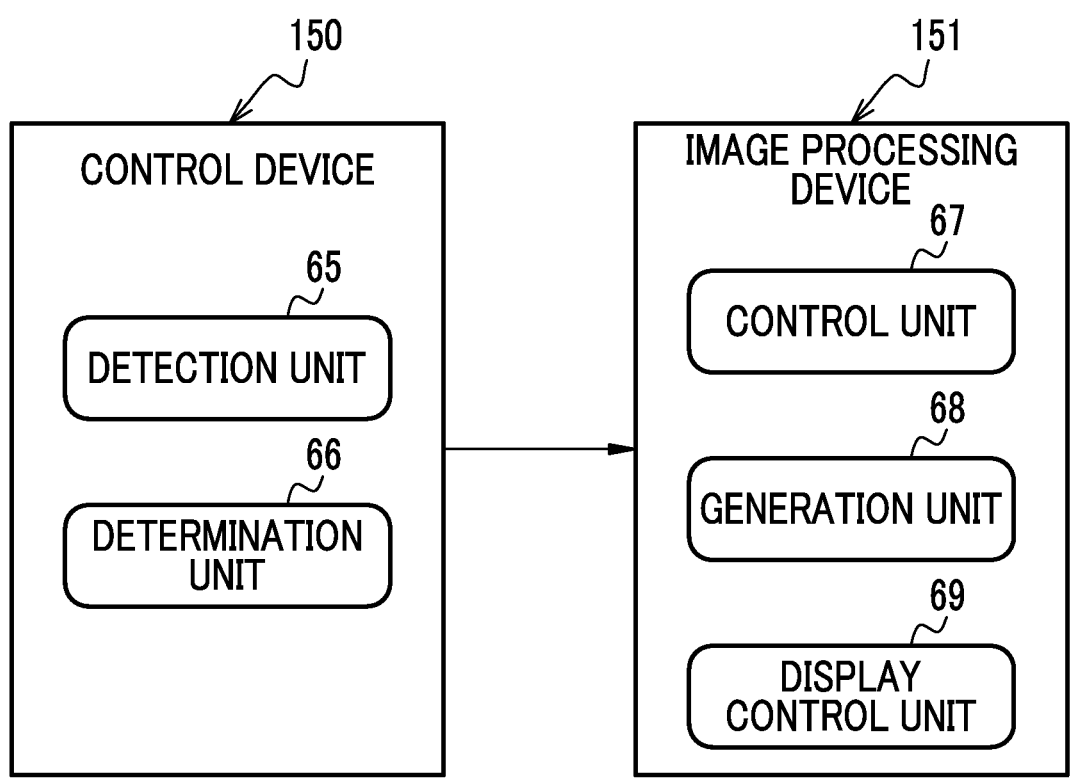
FIG. 48 is a diagram illustrating a control device comprising a detection unit and a determination unit and an image processing device comprising a control unit, a generation unit, and a display control unit.

The control device 150 illustrated in FIG. 48 comprises the detection unit 65 and the determination unit 66 and does not comprises the control unit 67, the generation unit 68, and the display control unit 69. The control unit 67, the generation unit 68, and the display control unit 69 are provided in an image processing device 151 different from the control device 150. The control device 150 transmits the detection result 75 of the detection unit 65 and the determination result 76 of the determination unit 66 to the image processing device 151.

Here, the control unit 67 of the image processing device 151 has the functions of the "first control unit" according to the technology of the present disclosure. Further, the display control unit 69 has a function of displaying the image display screen 90 illustrated in FIG. 25 and the functions of the "fourth notification unit" according to the technology of the present disclosure.

The control device 150 may be provided with a control unit having the functions of the "second control unit", the "third control unit", and the "fourth control unit" according to the technology of the present disclosure. Further, the control device 150 may be provided with a display control unit having the functions of the "first notification unit", the "second notification unit", and the "third notification unit" according to the technology of the present disclosure.

The first to fourth notification units are not limited to the display control unit 69 that displays, for example, the notification screens 85 and 100 on the display 54 exemplified in each of the above-described embodiments. The notification unit may be a notification unit that notifies information with voice or a notification unit that prints out information on a paper medium.

In each of the above-described embodiments, the mammography apparatus 10 has been exemplified. In the related art, performing tomosynthesis imaging in the mammography apparatus 10 has been found to be useful as a method for easily finding lesions such as microcalcifications of the breast M. Therefore, it is preferable to apply the tomosynthesis imaging control device according to the present disclosure to the mammography apparatus 10.

Of course, the tomosynthesis imaging control device according to the present disclosure may be applied to imaging apparatuses other than the mammography apparatus 10. For example, the tomosynthesis imaging control device according to the present disclosure may be applied to an imaging apparatus 160 illustrated in FIG. 49 which captures the image of the subject H during surgery.

The imaging apparatus 160 comprises an apparatus main body 162 having a control device 161 provided therein and an arm 163 having a substantially C-shape in a side view. A carriage 164 is attached to the apparatus main body 162 such that the apparatus main body 162 can be moved. The arm 163 includes a radiation source accommodation portion 165, a detector accommodation portion 166, and a main body portion 167. As in the mammography apparatus 10 illustrated in FIG. 1, the radiation source accommodation portion 165 accommodates a radiation source 168. In addition, the detector accommodation portion 166 accommodates a radiation detector 169. The radiation source accommodation portion 165 and the detector accommodation portion 166 are held by the main body portion 167 at a posture where they face each other.

The radiation source 168 and the radiation detector 169 have the same basic configurations as the radiation source 25 and the radiation detector 26 illustrated in FIG. 1, respectively. However, the imaging apparatus 160 captures an image of an object, such as the entire chest of the subject H, which is larger than the breast M. Therefore, a radiation tube 170 forming the radiation source 168 has a larger diameter than each radiation tube 27 of the mammography apparatus 10. In addition, the radiation detector 169 has an imaging surface 171 whose area is larger than that of the imaging surface 49 of the radiation detector 26. The number of radiation tubes 170 arranged may increase in order to correspond to the capture of the image of a large object.

The detector accommodation portion 166 is inserted below a bed 172 on which the subject H lies supine. The bed 172 is made of a material that transmits the radiation 37. The radiation source accommodation portion 165 is provided above the subject H at a position that faces the detector accommodation portion 166 with the subject H interposed therebetween.

In the imaging apparatus 160, similarly to the mammography apparatus 10, the control device 161 detects the state of each radiation tube 170, determines whether or not to permit generation of the tomographic image T on the basis of the detection result, and outputs the determination result. The imaging apparatus 160 can perform simple imaging using one radiation tube 170, in addition to the tomosynthesis imaging. In addition, instead of the simple imaging, the imaging apparatus may generate a composite radiographic image. Further, the imaging apparatus 160 may capture both still radiographic images and moving radiographic images. Furthermore, reference numeral 173 indicates a housing for the radiation source 168.

The tomosynthesis imaging control device according to the present disclosure may be applied to a general radiography apparatus configured by combining a ceiling-suspended radiation source and an upright imaging table or a decubitus imaging table in which a radiation detector is set, in addition to the imaging apparatus 160 for surgery. Further, the tomosynthesis imaging control device according to the present disclosure may be applied to, for example, a cart-type mobile radiography apparatus which is moved to each hospital room and is used to capture the image of the subject H.

Each numerical value, such as the temperature threshold value, the number-of-times threshold value, the minimum required number of radiation tubes, the maximum allowable number of radiation tubes, the frequency threshold value, or the upper limit of the total number of irradiation retrying operations, can be appropriately changed.

In a case in which the tomographic image T is viewed through the terminal apparatus 15, the notification screen 100 for notifying that there is a radiation tube 27 which has not emitted the radiation 37 as illustrated in FIG. 26 may be displayed.

The hardware configuration of the computer forming the tomosynthesis imaging control device can be modified in various ways. For example, the tomosynthesis imaging control device may be configured by a plurality of computers that are separated as hardware in order to improve processing capability and reliability. For example, the functions of the detection unit 65 and the functions of the determination unit 66 are distributed to two server computers. In this case, the two server computers form the tomosynthesis imaging control device.

As described above, the hardware configuration of the computer can be appropriately changed according to the required performance, such as processing capability, safety, and reliability. Further, not only hardware but also an application program, such as the operation program 60, can be duplicated, or distributed and stored in a plurality of storage devices in order to ensure safety and reliability.

In each of the above-described embodiments, for example, the following various processors can be used as the hardware structure of processing units performing various processes, such as the detection unit 65 (the temperature detection unit 70, the discharge detection unit 71, and the cathode failure detection unit 72), the determination unit 66, the control unit 67, the generation unit 68, and the display control unit 69. The various processors include, for example, the CPU 52 which is a general-purpose processor executing software to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the invention described in the following Supplementary Note 1 from the above description.

Supplementary Note 1

There is provided a tomosynthesis imaging control device comprising: a detection processor that, in a case in which tomosynthesis imaging that continuously irradiates an object with radiation at a plurality of different irradiation angles to generate a tomographic image in any tomographic plane of the object is performed using at least three or more radiation tubes, detects whether or not the radiation tubes are in an abnormal state; and a determination processor that determines whether or not to permit the generation of the tomographic image on the basis of projection images captured using at least two or more radiation tubes other than a radiation tube detected to be in the abnormal state by the detection processor among the at least three or more radiation tubes.

In the technology according to the present disclosure, the above-described various embodiments and/or various modification examples may be combined with each other. In addition, the present disclosure is not limited to the above-described embodiments and various configurations can be used without departing from the scope and spirit of the present disclosure. Further, the technology of the present disclosure is applied to a storage medium that temporarily stores the program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the scope and spirit of the technology of the present disclosure. In addition, the description of, for example, common technical knowledge that does not need to be particularly described to enable the implementation of the technology of the present disclosure are omitted in order to avoid confusion and facilitate the understanding of portions related to the technology of the present disclosure.

In the specification, "A and/or B" is synonymous with "at least one of A and B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A tomosynthesis imaging control device comprising:
   a detection processor that, in a case in which tomosynthesis imaging that continuously irradiates an object with radiation at a plurality of different irradiation angles to generate a tomographic image in any tomographic plane of the object is performed using three or more radiation tubes, detects whether or not the radiation tubes are in an abnormal state; and a determination processor that determines whether or not to permit the generation of the tomographic image on the basis of projection images captured using at least two or more radiation tubes other than a radiation tube detected to be in the abnormal state by the detection processor among the three or more radiation tubes, wherein the plurality of radiation tubes include irradiation essential radiation tubes from which the emission of the radiation is essential, and in a case in which a detection result of the detection processor indicates that the irradiation essential radiation tubes are in a normal state and the number of radiation tubes in the normal state including the irradiation essential radiation tubes is equal to or greater than a preset minimum required number of radiation tubes, the determination processor determines to permit the generation of the tomographic image.

2. The tomosynthesis imaging control device according to claim 1, further comprising:
a generation processor that generates the tomographic image; and
a first control processor that controls an operation of the generation processor on the basis of a determination result of the determination processor.

3. The tomosynthesis imaging control device according to claim 2,
wherein, in a case in which the radiation tube in the abnormal state is present and the determination processor determines to permit the generation of the tomographic image, the generation processor generates the tomographic image on the basis of the projection images captured using two or more radiation tubes other than the radiation tube detected to be in the abnormal state by the detection processor.

4. The tomosynthesis imaging control device according to claim 3,
wherein the generation processor generates the tomographic image without using the projection image captured using the radiation tube detected to be in the abnormal state by the detection processor.

5. The tomosynthesis imaging control device according to claim 2,
wherein, in a case in which the detection processor does not detect the radiation tube in the abnormal state, the generation processor generates the tomographic image on the basis of projection images captured using all of the three or more radiation tubes.

6. The tomosynthesis imaging control device according to claim 1,
wherein, in a case in which the detection result of the detection processor indicates that the irradiation essential radiation tubes are in the abnormal state or in a case in which the detection result indicates that the number of radiation tubes in the abnormal state except the irradiation essential radiation tubes is greater than a preset maximum allowable number of radiation tubes, the determination processor determines not to permit the generation of the tomographic image.

7. The tomosynthesis imaging control device according to claim 1,
wherein the irradiation essential radiation tubes are outermost radiation tubes in a range of a minimum irradiation angle required to generate the tomographic image with the preset resolution level.

8. The tomosynthesis imaging control device according to claim 1,
wherein the irradiation essential radiation tubes are radiation tubes disposed at both ends among the plurality of radiation tubes.

9. The tomosynthesis imaging control device according to claim 1,
wherein the detection processor detects that the radiation tube is in the abnormal state in at least one of a case in which a temperature of the radiation tube is equal to or greater than a preset temperature threshold value, a case in which the number of occurrences of discharge in the radiation tube has reached a preset number-of-times threshold value, or a case in which a failure has been recognized in a cathode of the radiation tube.

10. The tomosynthesis imaging control device according to claim 9, further comprising:
a second control processor that operates the irradiation essential radiation tube among the plurality of radiation tubes first and directs the detection processor to detect first whether or not the number of occurrences of discharge in the irradiation essential radiation tube has reached the number-of-times threshold value and whether or not a failure has been recognized in the cathode of the irradiation essential radiation tube.

11. The tomosynthesis imaging control device according to claim 9,
wherein the number-of-times threshold value is equal to or greater than 2, and
the tomosynthesis imaging control device further comprises a third control processor that directs the radiation tube, in which the number of occurrences of discharge is equal to or greater than 1 and is less than the number-of-times threshold value, to perform an irradiation retrying operation for emitting the radiation again.

12. The tomosynthesis imaging control device according to claim 11,
wherein an upper limit is set for a total number of irradiation retrying operations.

13. The tomosynthesis imaging control device according to claim 11, further comprising:
a first notification processor that notifies that the irradiation retrying operation has been performed.

14. The tomosynthesis imaging control device according to claim 9, further comprising:
a second notification processor that notifies that maintenance is required for the radiation tube in which a frequency of discharge has reached a preset frequency threshold value.

15. The tomosynthesis imaging control device according to claim 1, further comprising:
a third notification processor that notifies at least one of the temperature of each of the plurality of radiation tubes or a ratio of an amount of heat applied to a heat capacity of each of the plurality of radiation tubes.

16. The tomosynthesis imaging control device according to claim 1, further comprising:
a fourth control processor that does not operate a radiation tube disposed at a position that is symmetric to the radiation tube in the abnormal state in the detection result of the detection processor with respect to a line.

17. The tomosynthesis imaging control device according to claim 1, further comprising:

a fourth notification processor that notifies that the radiation tube which has not emitted the radiation is present in a case in which the detection result of the detection processor indicates that the radiation tube in the abnormal state is present, the determination processor determines to permit the generation of the tomographic image, and the tomographic image has been generated.

18. A method for operating a tomosynthesis imaging control device, the method comprising:
a detection step of, in a case in which tomosynthesis imaging that continuously irradiates an object with radiation at a plurality of different irradiation angles to generate a tomographic image in any tomographic plane of the object is performed using three or more radiation tubes, detecting whether or not the radiation tubes are in an abnormal state; and
a determination step of determining whether or not to permit the generation of the tomographic image on the basis of projection images captured using two or more radiation tubes other than a radiation tube detected to be in the abnormal state in the detection step among the three or more radiation tubes,
wherein the plurality of radiation tubes include irradiation essential radiation tubes from which the emission of the radiation is essential, and
in a case in which a detection result of the detection step indicates that the irradiation essential radiation tubes are in a normal state and the number of radiation tubes in the normal state including the irradiation essential radiation tubes is equal to or greater than a preset minimum required number of radiation tubes, the determination step determines to permit the generation of the tomographic image.

19. A radiation source comprising:
a plurality of the radiation tubes whose operation is controlled by a tomosynthesis imaging control device that includes:
a detection processor that, in a case in which tomosynthesis imaging that continuously irradiates an object with radiation at a plurality of different irradiation angles to generate a tomographic image in any tomographic plane of the object is performed using three or more radiation tubes, detects whether or not the radiation tubes are in an abnormal state; and
a determination processor that determines whether or not to permit the generation of the tomographic image on the basis of projection images captured using two or more radiation tubes other than a radiation tube detected to be in the abnormal state by the detection processor among the three or more radiation tubes,
wherein the plurality of radiation tubes include irradiation essential radiation tubes from which the emission of the radiation is essential to generate the tomographic image with a preset resolution level, and
the irradiation essential radiation tube has a higher heat dissipation performance than other radiation tubes and/or has a higher heat capacity than other radiation tubes.

20. A tomosynthesis imaging control device comprising:
a detection processor that, in a case in which tomosynthesis imaging that continuously irradiates an object with radiation at a plurality of different irradiation angles to generate a tomographic image in any tomographic plane of the object is performed using three or more radiation tubes, detects whether or not the radiation tubes are in an abnormal state; and
a determination processor that determines whether or not to permit the generation of the tomographic image on the basis of projection images captured using two or more radiation tubes other than a radiation tube detected to be in the abnormal state by the detection processor among the three or more radiation tubes,
wherein the plurality of radiation tubes include irradiation essential radiation tubes from which the emission of the radiation is essential, and
in a case in which the detection result of the detection processor indicates that the irradiation essential radiation tubes are in the abnormal state or in a case in which the detection result indicates that the number of radiation tubes in the abnormal state except the irradiation essential radiation tubes is greater than a preset maximum allowable number of radiation tubes, the determination processor determines not to permit the generation of the tomographic image.

* * * * *